(12) United States Patent
Ramakrishnan et al.

(10) Patent No.: US 8,309,084 B2
(45) Date of Patent: *Nov. 13, 2012

(54) CHIMERIC AND HUMANIZED ANTIBODIES TO α5β1 INTEGRIN THAT MODULATE ANGIOGENESIS

(75) Inventors: Vanitha Ramakrishnan, Belmont, CA (US); David Powers, Fairfax, CA (US); Dale E. Johnson, Emeryville, CA (US); Ursula Jeffry, Redwood City, CA (US); Vinay Bhaskar, San Francisco, CA (US)

(73) Assignee: Abbott Biotherapeutics Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/009,757

(22) Filed: Jan. 19, 2011

(65) Prior Publication Data

US 2011/0300133 A1 Dec. 8, 2011

Related U.S. Application Data

(63) Continuation of application No. 11/852,147, filed on Sep. 7, 2007, now Pat. No. 7,897,148, which is a continuation of application No. 10/724,274, filed on Nov. 26, 2003, now Pat. No. 7,276,589.

(60) Provisional application No. 60/508,149, filed on Sep. 30, 2003, provisional application No. 60/429,743, filed on Nov. 26, 2002.

(51) Int. Cl.
*A61K 39/395* (2006.01)
*A61P 27/02* (2006.01)
*C07K 16/28* (2006.01)

(52) U.S. Cl. ................... 424/133.1; 530/387.3
(58) Field of Classification Search ............... 424/133.1; 530/387.3
See application file for complete search history.

(56) References Cited

U.S. PATENT DOCUMENTS

| | | | |
|---|---|---|---|
| 4,704,366 A | 11/1987 | Juarex-Salinas et al. | |
| 4,801,687 A | 1/1989 | Ngo | |
| 4,935,496 A | 6/1990 | Kudo | |
| 4,946,778 A | 8/1990 | Ladner | |
| 5,502,167 A | 3/1996 | Waldman | |
| 5,530,101 A | 6/1996 | Queen et al. | |
| 5,536,814 A | 7/1996 | Rousiathi | |
| 5,558,864 A | 9/1996 | Bendig | |
| 5,639,641 A | 6/1997 | Pedersen | |
| 5,677,181 A | 10/1997 | Parish | |
| 5,693,493 A | 12/1997 | Robinson | |
| 5,698,417 A | 12/1997 | Robinson | |
| 5,705,154 A | 1/1998 | Dalie | |
| 5,750,078 A | 5/1998 | Shitara | |
| 5,770,403 A | 6/1998 | Dalie et al. | |
| 5,874,081 A | 2/1999 | Parish | |
| 5,922,676 A | 7/1999 | Pasqualini | |
| 6,123,941 A | 9/2000 | Bissell et al. | |
| 6,852,318 B1 | 2/2005 | Varner | |
| 7,276,589 B2 | 10/2007 | Ramakrishnan et al. | |
| 7,285,268 B2* | 10/2007 | Ramakrishnan et al. | .. 424/133.1 |
| 8,017,116 B2* | 9/2011 | Ramakrishnan et al. | .. 424/133.1 |
| 2002/0172675 A1 | 11/2002 | Varner | |
| 2003/0157641 A1 | 8/2003 | Reff et al. | |
| 2004/0077544 A1 | 4/2004 | Varner | |
| 2004/0259152 A1 | 12/2004 | Murray et al. | |
| 2005/0163769 A1 | 7/2005 | Ramakrishan et al. | |

FOREIGN PATENT DOCUMENTS

| | | |
|---|---|---|
| EP | 0 896 002 | 2/1999 |
| WO | WO 95/14714 | 6/1995 |
| WO | WO 95/14772 | 6/1995 |
| WO | WO 95/22618 | 8/1995 |
| WO | WO 97/33887 | 9/1997 |
| WO | WO 99/55913 | 11/1999 |
| WO | WO 99/58139 | 11/1999 |
| WO | WO 01/11086 | 2/2001 |
| WO | WO 01/53262 | 7/2001 |
| WO | WO 01/53297 | 7/2001 |
| WO | WO 02/079492 | 10/2002 |
| WO | WO 2004/089988 | 10/2004 |

OTHER PUBLICATIONS

Edelman, et al., "Quantitative image analysis of laser-induced chordial neovasculariztion in rat," Exp. Eye Res., vol. 71:523-533 (2000).
Loike, J.D., et al., "Blockade of alpha5beta1 integrins reverses the inhibitory effect of tenacin on chamotacis of human monocytes and polymorphonuclear leukocytes through three-dimensional gels of extracellular matrix proteins", Journal of Immunology, vol. 166(12):7534-7542 (2001).
Wong, et al "Intravetrael VEGF and bFGF produce florid retinal neovascularization and hemorrhage in the rabbit" Current Eye Research, vol. 22(2):140-147 (2001).
Sequence search alignment for SEQ ID Nos. 1 and 7 (pp. 1-2).
Zhao et al., "Integrin activation by regulated dimerization and oligomerization of platelet endothelial cell adhesion molecule (PECAm)-1 from within the cell", J. Cell Biol. 152(9):65-71.
Josic, D., et al., "Analytical and preparative methods for purification of antibodies", Food Technology and Biotechnology, vol. 39(3):215-226 (2001).
Vajdos, et al., "Comprehensive functional maps of the antigen-binding site of an anti-ErbB2 antibody obtained with shotgun scanning mutagenesis", J. Molec. Biol 320:415-428 (2002).
"Eos Biotechnology files investigational new drug from novel targets with anti-angiogenic properties", www.pharmabiz.com/article/detnews.asp?articleid=13491&sectionid=14&z=y?., 2002.
"Protein design labs to acquire Eos Biotechnology", www.pharmabiz.com/article/detnews.asp?articleid=14199&sectionid=14&z=y>, (2002).

(Continued)

Primary Examiner — Lynn Bristol
(74) Attorney, Agent, or Firm — Sughrue Mion, PLLC

(57) ABSTRACT

The present invention provides chimeric and humanized antibodies that specifically recognize α5β1 integrin, and methods for using the antibodies for reducing or inhibiting angiogenesis in a tissue. Also provided are methods of determining therapeutically acceptable doses of the antibodies and pharmaceutical compositions including the same.

6 Claims, 26 Drawing Sheets

OTHER PUBLICATIONS

Wilson, S., et al., "Fibronectin fragments promote human retinal endothelial cell adhesion and proliferation and ERK activation through alpha5beta1 integrin and PI3-kinase", Invest. Ophthalmol. Vis. Sci. vol. 44(4):1704-1715 (2003).

Proulx, et al., "Effect of quiescense on integrin γγ expression in human retinal pigment epithelium", Molecular Vision, vol. 473-481 (2003).

Ramakrishnan, V., et al., "A function-blocking chimeric antibody eos200-4, against alpha5beta1 integrin inhibits angiogenesis in a monkey model", Proceedings of the American Association for Cancer Research Annual Meeting, vol. 44: 605-606 (2003).

Ho Sun, K., et al., "The effect of a chimeric anti0integrin alpha5beta1 antibody (M200) on the migration of HUVECs and human cancer cells", Proceedings of the American Association for Cancer Research Annual Meeting, vol. 45:333 (2004).

Bhaskar, V., et al., "M200(volociximab),a chimeric antibody against integrin alpha5beta1 inhibits tumor growth by multiple mechanisms", Proceedings of the American Association for Cancer Research Annual Meeting, vol. 46:1063, 96th Annual Meeting of the American Association for Cancer Research (2005).

International Search Report dated Jul. 8, 2005.

Ramakrishnan, V., et al., "Preclinical evaluation of an anti [alpha]5[beta]1 integrin antibody as a novel anti-angiogeneic agent", Journal of Experimental Therapeutics and Oncology vol. 5(4):273-286 (2006).

Valera Pharmaceuticals, Press Release: Hydron Implant Technology, pp. 1.

Valera Pharmaceuticals, Technology Release: Hydron Implant Technology, pp. 1.

Kuwada, S.K., Volociximab, an angiogenesis inhibiting chimeric monoclonal antibody, Current Opinion in Molecular Therapeutics, vol. 9(1):92-98 (2007).

Pharmigen data sheet for IIA1 antibody (p. 1-2; Oct. 15, 2009).

Pharmigen data sheet for VC5 antibody (p. 1-2; Oct. 15, 2009).

Cranmer, et al., "Phase II study of volociximab (M200), an a5b1 anti-integrin antibody in metastatic melanoma (MCP)," ASCO 2006, Poster presentation.

Valle, et al., "Phase II study of volociximab (M200), an a5b1 anti-integrin antibody in metastic adenocarcinoma of the pancreas" ASCO 2006, Poster presentation.

Figlin, et al., "Phase II study of volociximab (M200), an a5b1 anti-integrinantibody in refactory metastaticclear cell renal cell cancer (RCC)," ASCO 2006, poster presentation.

Shalaby, et al., "Development of humanized bispecific antibodies reactive with cytotoxic lymphocytes and tumor cells overexpresseion in HER2 protooncogene," J. Exp. Med. 175:217-225 (1992).

Muller, et al., "The first constant domain (CH1 and CL) of antibody used as heterodimerization domain for bispecific miniantibodies," FEBS Letters 422:259-264 (1998).

Jin, et al., "Bicistronic adenovirus-mediated gene transfer of CTLA4Ig gene and CD40Ig gene result in indefinite survival of islet xenograft," Transplantation Proceedings 35:3165-3166 (2003).

MacCallum, et al. J. Mol. Bio. 262:732-745 (1996).

Depascalis, et al., "Grafting of abbreviated complementarily-determining regions containing specificity-determining residues essential for ligand contact to engineer a less immunogenic humanized monoclonal antibody" Journal of Immunology 169:3076-3084 (2002).

Casset, et al.,"A peptide mimetic of an anti-CD4 monoclonal antibody by rational design", BBRC 307:198-205 (2003).

Vajdos, et al., Comprehensive functional maps of the antigen-binding site of an anti-ErbB2 antibody obtained with shotgun scanning mutagenesis J. Mol. Biol. 302:415-428 (2002).

Holm, et al. "Functional mapping and single chain construction of the anti-cytokeratin 8 monoclonal antibody TS1" Mol. Immunol. 44:1075-1084 (2007).

Chen, et al. "Selection and analysis of an optimized anti-vegf antibody; crystal structure of an affinity-matured fab in complex with antigen," J. Mol. Bio 293:865-881 (1999).

Wu et al., "Humanization of a murine monoclonal antibody by dimultaneous optimization of framework and CDR resides" J. Mol. Biol. 294:151-162 (1999).

Brummell, et al. "Probing the combing site of an anti-carbohydrate antibody by saturation-mutagenesis: Role of the heavy-chain Cdr3 residues" Biochemistry 32:1180-1187 (1993).

Kobayashi, et al., "Tryptophan H33 plays an important role in pyrimidine (6-4) pyrimidone photoproduct binding by a high-affinity antibody",(Protein Engineering 12:879-844 (1999)).

Burks, et al. "In virto scanning saturation mutagenesis of an antibody binding pocket," PNAS 94:412-417 (1997).

Jangs, et al. "The structural basis for DNA binding by an anti-DNA autoantibody," Molec. Immunol. 35:1207-1217 (1998).

Brorson, et al. "Mutational analysis of avidity and fine specificity of anti-levan antibodies", The Journal of Immunology 163(12):6694-7001 (1999).

Dufner et al.,"Harnessing phage and ribosome display for antibody optimization" Trends Biotecnol. 24(11):523-529 (2006) Epub Sep. 26, 2006.

Colman, P.M., "Effects of amino acid sequence changes on antibody-antigen interactions", Res. Immunol. 145(1):33-36 (1994).

Ryan, S.J., "Development of an experimental model of subretinal neovascularzation in disciform macular degeneration", Transactions of the American Ophthalmological Society, vol. 77 (1979), pp. 707-745.

Ryan, S.J., "Subretinal neovascularization: natural history of an experimental model", Archives of Ophthalmology, vol. 100 (1982), pp. 1804-1809.

Rudikoff et al., P.N.A.S. USA, vol. 79 (1982), pp. 1979-1983.

Pytela, et al.,"Identification and isolation of a 140 kd cell surface glycoprotein with properties expected of a fibronectin receptor" Cell 40:191-198 (1985).

Thorpe, et al., "Monoclonal antibodies in biological clinical applications", (1985), pp. 475-506.

Argraves, et al.,"cDNA sequence from the alpha sun unit of the fibronectin receptor predict a transmembrane domain and a short cytoplasmic peptide," J. Biol. Chem. 261(28): 12922-12924 (1986).

Amit, et al., "Three dimensional structure of an antigen-antibody complex at 2.8 A resolution," Science 233:747-753 (1986).

Conforti, et al., "Human endothelial cells express integrin receptors on the luminal aspect of their membrane", Blood, vol. 80(2)(1992), pp. 437-446.

Grossniklaus, H., et al., "Immunohistochemical and histochemical properties of surgically excised subretinal neovascular membranes in age-related macular degeneration", American Journal of Ophthalmology, vol. 114(4) (1992):464-472.

Hackett, R., et al., (1996) Dermatotoxicology. 5th ed. (Ed. by F.B. Marzulli and H.I. Maibach) Hemisphere Publishing Corp., Washington, D.C.

Varner, et al., "Integrins and cancer", Current Opinion in Cell Biology, vol. 8(5) (1996), pp. 724-730.

Varner, et al., "Tumor angiogenesis and the role of vascular cell integrin alphavbeta3," Important Advances in Oncology (1996), pp. 69-87.

Varner, et al., "Antagonists of vascular cell integrin alpha5beta1 inhibit angiogenesis" Circulation, vol. 98(17):4166 (1998).

Van Der Loo Johannes C.M. et al., "VLA-5 is expressed by mouse and human long-term repopulating hematopoietic cells and mediates adhesion to extracellular matrix protein fibronectin", Journal of Clinical Investigation, vol. 102(5):1051-1061 (1998).

Storgard, C.M., et al., "Decreased angiogenesis and arthritic diseases in rabbits treated with an alpha5beta3 antagonist", The Journal of clinical investigation, vol. 103:47-54 (1999).

Wu, et al., J. Mol. Biol., vol. 294:151-162 (1999).

Zhao, M., et al., "A distinct integrin-mediated phagocytic pathway for extracellular matrix remodeling by RPE cells", Invest. Ophthalmol. Vis. SCi., Bol. 40(11):2173-2723 (1999).

Tolentino, M.J., et al., Angiography of fluoresceinated anti-vascular endothelial growth factor antibody and dextrans in experimental choroidal neovascularization, Archives of Ophthalmology, vol. 118:78-84 (2000).

Kim, S., et al., "Regulation of angiogeneis in vivo by ligation of integrin alpha5beta1 with the central cell-binding domain of fibronectin", American Journal of Pathology, vol. 156(4):2000-2004(2000).

Kim, S., et al., "Regulation of integrin alpha5beta3-mediated endothelial cell migration and angiogenesis by integrin alpha5beta1 and portein kinase", A Journal of Biological Chemistry vol. 275(43):33920-33928 (2000).

Wu, H., et al.,"The expression of integrin alpha5beta1 and transforming growth factor-beta in pulmonary fibrosis of rat", Chinese Journal of Pathology 28(6): abstract (1999).

* cited by examiner

IIA1 V_H (SEQ ID NO: 1):
QVQLKESGPGLVAPSQSLSITCTISGFSLTDYGVHWVRQPPGKGLEWLVVIWSDGSSTYNSALKSRMTIRK
DNSKSQVFLIMNSLQTDDSAMYYCARHGTYYGMTTTGDALDYWGQGTSVTVSS

V_H 1.0 (SEQ ID NO: 2):
QVQLVESGPGLVQPGGSLRISCAISGFSLTDYGVHWVRQAPGKGLEWLVVIWSDGSSTYNSALKSRMTISK
DNSKSTVYLQMNSLRAEDTAMYYCARHGTYYGMTTTGDALDYWGQGTLVTVSS

V_H 2.0 (SEQ ID NO: 3):
EVQLVESGGGLVQPGGSLRISCAISGFSLTDYGVHWVRQAPGKGLEWLVVIWSDGSSTYNSALKSRMTISK
DNSKNTVYLQMNSLRAEDTAVYYCARHGTYYGMTTTGDALDYWGQGTLVTVSS

V_H 3.0 (SEQ ID NO: 4):
EVQLVESGGGLVQPGGSLRLSCAASGFSLTDYGVHWVRQAPGKGLEWVSVIWSDGSSTYNSALKSRFTISR
DNSKNTLYLQMNSLRAEDTAVYYCARHGTYYGMTTTGDALDYWGQGTLVTVSS

V_H 4.0 (SEQ ID NO: 5):
EVQLVESGGGLVQPGGSLRLSCAISGFSLTDYGVHWVRQAPGKGLEWLVVIWSDGSSTYNSALKSRMTIS
KDNSKSTVYLQMNSLRAEDTAVYYCARHGTYYGMTTTGDALDYWGQGTLVTVSS

V_H 5.0 (SEQ ID NO: 6):
QVQLVESGGGLVQPGGSLRISCAISGFSLTDYGVHWVRQAPGKGLEWLVVIWSDGSSTYNSALKSRMTISK
DNSKSTVYLQMNSLRAEDTAMYYCARHGTYYGMTTTGDALDYWGQGTLVTVSS

IIA1 V_L (SEQ ID NO: 7):
QIVLTQSPAIMSASLGERVTMTCTASSSVSSNYLHWYQQKPGSAPNLWIYSTSNLASGVPARFSGSGSGTSY
SLTISSMEAEDAATYYCHQYLRSPPTFGGGTKLEIKR

V_L 1.0 (SEQ ID NO: 8):
DIQLTQSPSSMSASLGDRVTMTCTASSSVSSNYLHWYQQKPGKAPNLWIYSTSNLASGVPSRFSGSGSGTD
YTLTISSMQPEDFATYYCHQYLRSPPTFGQGTKLEIKR

V_L 2.0 (SEQ ID NO: 9):
DIQLTQSPSSLSASVGDRVTMTCTASSSVSSNYLHWYQQKPGKAPKLWIYSTSNLASGVPSRFSGSGSGTDY
TLTISSMQPEDFATYYCHQYLRSPPTFGQGTKLEIKR

V_L 3.0 (SEQ ID NO: 10):
DIQMTQSPSSLSASVGDRVTITCTASSSVSSNYLHWYQQKPGKAPKLLIYSTSNLASGVPSRFSGSGSGTDFT
LTISSLQPEDFATYYCHQYLRSPPTFGQGTKVEIKR

V_L 4.0 (SEQ ID NO: 11):
DIQLTQSPSSLSASVGDRVTITCTASSSVSSNYLHWYQQKPGKAPKLWIYSTSNLASGVPSRFSGSGSGTDY
TLTISSLQPEDFATYYCHQYLRSPPTFGQGTKVEIKR

V_L 5.0 (SEQ ID NO: 12):
DIQLTQSPSSLSASVGDRVTMTCTASSSVSSNYLHWYQQKPGKAPKLWIYSTSNLASGVPSRFSGSGSGTDY
TLTISSLQPEDFATYYCHQYLRSPPTFGQGTKVEIKR

FIGURE 1

|  | FR1 | CDR1 | FR2 | CDR2 | FR3 | CDR3 | FR4 |
|---|---|---|---|---|---|---|---|
| IIA1 V_H | QVQLKESGPGLVAPSQSLSITCTIS | GFSLTDYGVH | WVRQPPGKGLEWLV | VIWSDGSSTYNSALKS | RMTIRKDNSKSQVFLKMNSLQTDDSAMYYCAR | HGTYYGMTTTGDALDY | WGQGTSVTVSS |
| V_H 1.0 | QVQLVESGPGLVQPGGSLRLSCAIS | GFSLTDYGVH | WVRQAPGKGLEWLV | VIWSDGSSTYNSALKS | RMTISKDNSKSTVYLQMNSLRAEDTAMYYCAR | HGTYYGMTTTGDALDY | WGQGTLVTVSS |
| V_H 2.0 | EVQLVESGGGLVQPGGSLRLSCAIS | GFSLTDYGVH | WVRQAPGKGLEWLV | VIWSDGSSTYNSALKS | RMTISKDNSKFVYLQMNSLRAEDTAYYCAR | HGTYYGMTTTGDALDY | WGQGTLVTVSS |
| V_H 3.0 | EVQLVESGGGLVQPGGSLRLSCAAS | GFSLTDYGVH | WVRQAPGKGLEWVS | VIWSDGSSTYNSALKS | RFTISRDNSKNTLYLQMNSLRAEDTAVYYCAR | HGTYYGMTTTGDALDY | WGQGTLVTVSS |
| V_H 4.0 | EVQLVESGGGLVQPGGSLRLSCAIS | GFSLTDYGVH | WVRQAPGKGLEWLV | VIWSDGSSTYNSALKS | RMTISKDNSKSTVYLQMNSLRAEDTAVYYCAR | HGTYYGMTTTGDALDY | WGQGTLVTVSS |
| V_H 5.0 | QVQLVESGGGLVQPGGSLRLSCAIS | GFSLTDYGVH | WVRQAPGKGLEWLV | VIWSDGSSTYNSALKS | RMTISKDNSKSTVYLQMNSLRAEDTAMYYCAR | HGTYYGMTTTGDALDY | WGQGTLVTVSS |

|  | FR1 | CDR1 | FR2 | CDR2 | FR3 | CDR3 | FR4 |
|---|---|---|---|---|---|---|---|
| IIA1 V_L | QIVLTQSPAIMSASLGERVTMTC | TASSSVSSNYLH | WYQQKPGSAPNLMIY | STSNLAS | GVPARFSGSGSGTSYSLTITSSMEAEDAATYYC | HQYLRSPPT | FGGGTKLEIKR |
| V_L 1.0 | DIQLTQSPSSLSMSASLGDRVTMTC | TASSSVSSNYLH | WYQQKPGKAPNLMIY | STSNLAS | GVPSRFSGSGSGTDYTLTITSSMQPEDFATYYC | HQYLRSPPT | FGQGTKLEIKR |
| V_L 2.0 | DIQLTQSPSSLSASVGDRVTITC | TASSSVSSNYLH | WYQQKPGKAPKLLIY | STSNLAS | GVPSRFSGSGSGTDYTLTITSSMQPEDFATYYC | HQYLRSPPT | FGQGTKLEIKR |
| V_L 3.0 | DIQMTQSPSSLSASVGDRVTITC | TASSSVSSNYLH | WYQQKPGKAPKLLIY | STSNLAS | GVPSRFSGSGSGTDFTLTISSLQPEDFATYYC | HQYLRSPPT | FGQGTKVEIKR |
| V_L 4.0 | DIQLTQSPSSLSASVGDRVTITC | TASSSVSSNYLH | WYQQKPGKAPKLMIY | STSNLAS | GVPSRFSGSGSGTDYTLTISSLQPEDFATYYC | HQYLRSPPT | FGQGTKVEIKR |
| V_L 5.0 | DIQLTQSPSSLSASVGDRVTMTC | TASSSVSSNYLH | WYQQKPGKAPKLMIY | STSNLAS | GVPSRFSGSGSGTDYTLTISSLQPEDFATYYC | HQYLRSPPT | FGQGTKVEIKR |

FIGURE 2

A. IIA1 V$_H$ sequences
[NA, SEQ ID NO: 13; AA, SEQ ID NO: 46]

```
  1  ATGGCTGTCCTGGGGCTGCTTCTCTGCCTGGTGACTTTCCCAAGCTGTGTCCTGTCCCAG
     M   A   V   L   G   L   L   L   C   L   V   T   F   P   S   C   V   L   S   Q
 61  GTGCAGCTGAAGGAGTCAGGACCTGGCCTGGTGGCGCCCTCACAGAGCCTGTCCATCACA
     V   Q   L   K   E   S   G   P   G   L   V   A   P   S   Q   S   L   S   I   T
121  TGCACCATCTCAGGGTTCTCATTAACCGACTATGGTGTTCACTGGGTTCGCCAGCCTCCA
     C   T   I   S   G   F   S   L   T   D   Y   G   V   H   W   V   R   Q   P   P
181  GGAAAGGGTCTGGAGTGGCTGGTAGTGATTTGGAGTGATGGAAGCTCAACCTATAATTCA
     G   K   G   L   E   W   L   V   V   I   W   S   D   G   S   S   T   Y   N   S
241  GCTCTCAAATCCAGAATGACCATCAGGAAGGACAACTCCAAGAGCCAAGTTTTCTTAATA
     A   L   K   S   R   M   T   I   R   K   D   N   S   K   S   Q   V   F   L   I
301  ATGAACAGTCTCCAAACTGATGACTCAGCCATGTACTACTGTGCCAGACATGGAACTTAC
     M   N   S   L   Q   T   D   D   S   A   M   Y   Y   C   A   R   H   G   T   Y
361  TACGGTATGACTACGACGGGGGATGCTTTGGACTACTGGGGTCAAGGAACCTCAGTCACC
     Y   G   M   T   T   T   G   D   A   L   D   Y   W   G   Q   G   T   S   V   T
421  GTCTCCTCA
     V   S   S
```

B. IIA1 V$_L$ sequences
[NA, SEQ ID NO: 14; AA, SEQ ID NO: 47]

```
  1  ATGGATTTTCAGGTGCAGATTTTCAGCTTCCTGCTAATCAGTGCCTCAGTCATAATGTCC
     M   D   F   Q   V   Q   I   F   S   F   L   L   I   S   A   S   V   I   M   S
 61  AGAGGACAAATTGTTCTCACCCAGTCTCCAGCAATCATGTCTGCATCTCTAGGGGAACGG
     R   G   Q   I   V   L   T   Q   S   P   A   I   M   S   A   S   L   G   E   R
121  GTCACCATGACCTGCACTGCCAGTTCAAGTGTAAGTTCCAATTACTTGCACTGGTACCAG
     V   T   M   T   C   T   A   S   S   S   V   S   S   N   Y   L   H   W   Y   Q
181  CAGAAGCCAGGATCCGCCCCCAATCTCTGGATTTATAGCACATCCAACCTGGCTTCTGGA
     Q   K   P   G   S   A   P   N   L   W   I   Y   S   T   S   N   L   A   S   G
241  GTCCCAGCTCGTTTCAGTGGCAGTGGGTCTGGGACCTCTTACTCTCTCACAATCAGCAGC
     V   P   A   R   F   S   G   S   G   S   G   T   S   Y   S   L   T   I   S   S
301  ATGGAGGCTGAAGATGCTGCCACTTATTACTGCCACCAGTATCTTCGTTCCCCACCGACG
     M   E   A   E   D   A   A   T   Y   Y   C   H   Q   Y   L   R   S   P   P   T
361  TTCGGTGGAGGCACCAAGCTGGAAATCAAA
     F   G   G   G   T   K   L   E   I   K
```

FIGURE 3

A. Antibody 200-4 V$_H$ sequences
[NA, SEQ ID NO: 15; AA, SEQ ID NO: 16]

```
  1  ATGGCTGTCCTGGGGCTGCTTCTCTGCCTGGTGACTTTCCCAAGCTGTGTCCTGTCCCAG
     M   A   V   L   G   L   L   L   C   L   V   T   F   P   S   C   V   L   S   Q
 61  GTGCAGCTGAAGGAGTCAGGACCTGGCCTGGTGGCGCCCTCACAGAGCCTGTCCATCACA
     V   Q   L   K   E   S   G   P   G   L   V   A   P   S   Q   S   L   S   I   T
121  TGCACCATCTCAGGGTTCTCATTAACCGACTATGGTGTTCACTGGGTTCGCCAGCCTCCA
     C   T   I   S   G   F   S   L   T   D   Y   G   V   H   W   V   R   Q   P   P
181  GGAAAGGGTCTGGAGTGGCTGGTAGTGATTTGGAGTGATGGAAGCTCAACCTATAATTCA
     G   K   G   L   E   W   L   V   V   I   W   S   D   G   S   S   T   Y   N   S
241  GCTCTCAAATCCAGAATGACCATCAGGAAGGACAACTCCAAGAGCCAAGTTTTCTTAATA
     A   L   K   S   R   M   T   I   R   K   D   N   S   K   S   Q   V   F   L   I
301  ATGAACAGTCTCCAAACTGATGACTCAGCCATGTACTACTGTGCCAGACATGGAACTTAC
     M   N   S   L   Q   T   D   D   S   A   M   Y   Y   C   A   R   H   G   T   Y
361  TACGGTATGACTACGACGGGGGATGCTTTGGACTACTGGGGTCAAGGAACCTCAGTCACC
     Y   G   M   T   T   T   G   D   A   L   D   Y   W   G   Q   G   T   S   V   T
421  GTCTCGAGC
     V   S   S
```

B. Antibody 200-4 V$_L$ sequences
[NA, SEQ ID NO: 17; AA, SEQ ID NO: 18]

```
  1  ATGGATTTTCAGGTGCAGATTTTCAGCTTCCTGCTAATCAGTGCCTCAGTCATAATGTCC
     M   D   F   Q   V   Q   I   F   S   F   L   L   I   S   A   S   V   I   M   S
 61  AGAGGACAAATTGTTCTCACCCAGTCTCCAGCAATCATGTCTGCATCTCTAGGGGAACGG
     R   G   Q   I   V   L   T   Q   S   P   A   I   M   S   A   S   L   G   E   R
121  GTCACCATGACCTGCACTGCCAGTTCAAGTGTAAGTTCCAATTACTTGCACTGGTACCAG
     V   T   M   T   C   T   A   S   S   S   V   S   S   N   Y   L   H   W   Y   Q
181  CAGAAGCCAGGATCCGCCCCCAATCTCTGGATTTATAGCACATCCAACCTGGCTTCTGGA
     Q   K   P   G   S   A   P   N   L   W   I   Y   S   T   S   N   L   A   S   G
241  GTCCCAGCTCGTTTCAGTGGCAGTGGGTCTGGGACCTCTTACTCTCTCACAATCAGCAGC
     V   P   A   R   F   S   G   S   G   S   G   T   S   Y   S   L   T   I   S   S
301  ATGGAGGCTGAAGATGCTGCCACTTATTACTGCCACCAGTATCTTCGTTCCCCACCGACG
     M   E   A   E   D   A   A   T   Y   Y   C   H   Q   Y   L   R   S   P   P   T
361  TTCGGTGGAGGCACCAAGCTCGAGATCAAA
     F   G   G   G   T   K   L   E   I   K
```

FIGURE 4

A. M200 V$_H$ sequences
[NA, SEQ ID NO: 19; AA, SEQ ID NO: 20]

```
  1  TCTAGACCACCATGGCTGTCCTGGGGCTGCTTCTCTGCCTGGTGACTTTCCCAAGCTGTG
              M  A  V  L  G  L  L  L  C  L  V  T  F  P  S  C
 61  TCCTGTCCCAGGTGCAGCTGAAGGAGTCAGGACCTGGCCTGGTGGCGCCCTCACAGAGCC
      V  L  S  Q  V  Q  L  K  E  S  G  P  G  L  V  A  P  S  Q  S
121  TGTCCATCACATGCACCATCTCAGGGTTCTCATTAACCGACTATGGTGTTCACTGGGTTC
      L  S  I  T  C  T  I  S  G  F  S  L  T  D  Y  G  V  H  W  V
181  GCCAGCCTCCAGGAAAGGGTCTGGAGTGGCTGGTAGTGATTTGGAGTGATGGAAGCTCAA
      R  Q  P  P  G  K  G  L  E  W  L  V  V  I  W  S  D  G  S  S
241  CCTATAATTCAGCTCTCAAATCCAGAATGACCATCAGGAAGGACAACTCCAAGAGCCAAG
      T  Y  N  S  A  L  K  S  R  M  T  I  R  K  D  N  S  K  S  Q
301  TTTTCTTAATAATGAACAGTCTCCAAACTGATGACTCAGCCATGTACTACTGTGCCAGAC
      V  F  L  I  M  N  S  L  Q  T  D  D  S  A  M  Y  Y  C  A  R
361  ATGGAACTTACTACGGAATGACTACGACGGGGGATGCTTTGGACTACTGGGGTCAAGGAA
      H  G  T  Y  Y  G  M  T  T  T  G  D  A  L  D  Y  W  G  Q  G
421  CCTCAGTCACCGTCTCCTCAG^GTAAGAATGGCCTCTAGA
      T  S  V  T  V  S  S
```

B. M200 V$_L$ sequences
[NA, SEQ ID NO: 21; AA, SEQ ID NO: 22]

```
  1  ACGCGTCCACCATGGATTTTCAGGTGCAGATTTTCAGCTTCCTGCTAATCAGTGCCTCAG
              M  D  F  Q  V  Q  I  F  S  F  L  L  I  S  A  S
 61  TCATAATGTCCAGAGGACAAATTGTTCTCACCCAGTCTCCAGCAATCATGTCTGCATCTC
      V  I  M  S  R  G  Q  I  V  L  T  Q  S  P  A  I  M  S  A  S
121  TAGGGGAACGGGTCACCATGACCTGCACTGCCAGTTCAAGTGTCAGTTCCAATTACTTGC
      L  G  E  R  V  T  M  T  C  T  A  S  S  S  V  S  S  N  Y  L
181  ACTGGTACCAGCAGAAGCCAGGATCCGCCCCCAATCTCTGGATTTATAGCACATCCAACC
      H  W  Y  Q  Q  K  P  G  S  A  P  N  L  W  I  Y  S  T  S  N
241  TGGCTTCTGGAGTCCCAGCTCGTTTCAGTGGCAGTGGGTCTGGGACCTCTTACTCTCTCA
      L  A  S  G  V  P  A  R  F  S  G  S  G  S  G  T  S  Y  S  L
301  CAATCAGCAGCATGGAGGCTGAAGATGCTGCCACTTATTACTGCCACCAGTATCTTCGTT
      T  I  S  S  M  E  A  E  D  A  A  T  Y  Y  C  H  Q  Y  L  R
361  CCCCACCGACGTTCGGTGGAGGCACCAAGCTGGAAATCAAAC^GTAAGTAGAATCCAAAGT
      S  P  P  T  F  G  G  G  T  K  L  E  I  K
421  CTAGA
```

FIGURE 5

M200 COMPLETE HEAVY CHAIN DNA SEQUENCE
(SEQ ID NO: 23)

CAGGTGCAGCTGAAGGAGTCAGGACCTGGCCTGGTGGCGCCCTCACAGAGCCTGTCCATC
ACATGCACCATCTCAGGGTTCTCATTAACCGACTATGGTGTTCACTGGGTTCGCCAGCCT
CCAGGAAAGGGTCTGGAGTGGCTGGTAGTGATTTGGAGTGATGGAAGCTCAACCTATAAT
TCAGCTCTCAAATCCAGAATGACCATCAGGAAGGACAACTCCAAGAGCCAAGTTTTCTTA
ATAATGAACAGTCTCCAAACTGATGACTCAGCCATGTACTACTGTGCCAGACATGGAACT
TACTACGGAATGACTACGACGGGGGATGCTTTGGACTACTGGGGTCAAGGAACCTCAGTC
ACCGTCTCCTCAGCTTCCACCAAGGGCCCATCCGTCTTCCCCCTGGCGCCCTGCTCCAGG
AGCACCTCCGAGAGCACAGCCGCCCTGGGCTGCCTGGTCAAGGACTACTTCCCCGAACCG
GTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTG
GGCACGAAGACCTACACCTGCAACGTAGATCACAAGCCCAGCAACACCAAGGTGGACAAG
AGAGTTGAGTCCAAATATGGTCCCCCATGCCCATCATGCCCAGCACCTGAGTTCCTGGGG
GGACCATCAGTCTTCCTGTTCCCCCCAAAACCCAAGGACACTCTCATGATCTCCCGGACC
CCTGAGGTCACGTGCGTGGTGGTGGACGTGAGCCAGGAAGACCCCGAGGTCCAGTTCAAC
TGGTACGTGGATGGCGTGGAGGTGCATAATGCCAAGACAAAGCCGCGGGAGGAGCAGTTC
AACAGCACGTACCGTGTGGTCAGCGTCCTCACCGTCCTGCACCAGGACTGGCTGAACGGC
AAGGAGTACAAGTGCAAGGTCTCCAACAAAGGCCTCCCGTCCTCCATCGAGAAAACCATC
TCCAAAGCCAAAGGGCAGCCCCGAGAGCCACAGGTGTACACCCTGCCCCCATCCCAGGAG
GAGATGACCAAGAACCAGGTCAGCCTGACCTGCCTGGTCAAAGGCTTCTACCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAGGCTAACCGTGGACAAGAGCAGG
TGGCAGGAGGGGAATGTCTTCTCATGCTCCGTGATGCATGAGGCTCTGCACAACCACTAC
ACACAGAAGAGCCTCTCCCTGTCTCTGGGTAAA

M200 COMPLETE LIGHT CHAIN DNA SEQUENCE
(SEQ ID NO: 24)

CAAATTGTTCTCACCCAGTCTCCAGCAATCATGTCTGCATCTCTAGGGGAACGGGTCACC
ATGACCTGCACTGCCAGTTCAAGTGTAAGTTCCAATTACTTGCACTGGTACCAGCAGAAG
CCAGGATCCGCCCCCAATCTCTGGATTTATAGCACATCCAACCTGGCTTCTGGAGTCCCA
GCTCGTTTCAGTGGCAGTGGGTCTGGGACCTCTTACTCTCTCACAATCAGCAGCATGGAG
GCTGAAGATGCTGCCACTTATTACTGCCACCAGTATCTTCGTTCCCCACCGACGTTCGGT
GGAGGCACCAAGCTGGAAATCAAACGAACTGTGGCTGCACCATCTGTCTTCATCTTCCCG
CCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGT

FIGURE 9

M200 COMPLETE HEAVY CHAIN AMINO ACID SEQUENCE
(SEQ ID NO: 25)

QVQLKESGPGLVAPSQSLSITCTISGFSLTDYGVHWVRQPPGKGLEWLVVIWSDGSSTYN
SALKSRMTIRKDNSKSQVFLIMNSLQTDDSAMYYCARHGTYYGMTTTGDALDYWGQGTSV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPSCPAPEFLG
GPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSR
WQEGNVFSCSVMHEALHNHYTQKSLSLSLGK

M200 COMPLETE LIGHT CHAIN AMINO ACID SEQUENCE
(SEQ ID NO: 26)

QIVLTQSPAIMSASLGERVTMTCTASSSVSSNYLHWYQQKPGSAPNLWIYSTSNLASGVPARF
SGSGSGTSYSLTISSMEAEDAATYYCHQYLRSPPTFGGGTKLEIKRTVAAPSVFIFPPSDEQL
KSGTASVVCLLNNFYPREAKVQWKVDNALQSGNSQESVTEQDSKDSTYSLSSTLTLSKADYEK
HKVYACEVTHQGLSSPVTKSFNRGEC

FIGURE 10

F200 COMPLETE HEAVY CHAIN DNA SEQUENCE
(SEQ ID NO: 27)

CAGGTGCAGCTGAAGGAGTCAGGACCTGGCCTGGTGGCGCCCTCACAGAGCCTGTCCATC
ACATGCACCATCTCAGGGTTCTCATTAACCGACTATGGTGTTCACTGGGTTCGCCAGCCT
CCAGGAAAGGGTCTGGAGTGGCTGGTAGTGATTTGGAGTGATGGAAGCTCAACCTATAAT
TCAGCTCTCAAATCCAGAATGACCATCAGGAAGGACAACTCCAAGAGCCAAGTTTTCTTA
ATAATGAACAGTCTCCAAACTGATGACTCAGCCATGTACTACTGTGCCAGACATGGAACT
TACTACGGAATGACTACGACGGGGGATGCTTTGGACTACTGGGGTCAAGGAACCTCAGTC
ACCGTCTCCTCAGCTTCCACCAAGGGCCCATCCGTCTTCCCCCTGGCGCCCTGCTCCAGG
AGCACCTCCGAGAGCACAGCCGCCCTGGGCTGCCTGGTCAAGGACTACTTCCCCGAACCG
GTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTG
GGCACGAAGACCTACACCTGCAACGTAGATCACAAGCCCAGCAACACCAAGGTGGACAAG
AGAGTTGAGTCCAAATATGGTCCCCCATGCCCATCA

F200 COMPLETE HEAVY CHAIN AMINO ACID SEQUENCE
(SEQ ID NO: 28)

QVQLKESGPGLVAPSQSLSITCTISGFSLTDYGVHWVRQPPGKGLEWLVVIWSDGSSTYN
SALKSRMTIRKDNSKSQVFLIMNSLQTDDSAMYYCARHGTYYGMTTTGDALDYWGQGTSV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPS

FIGURE 11 huM200 COMPLETE HEAVY CHAIN DNA SEQUENCE
(SEQ ID NO: 29)

GAGGTGCAGCTGGTGGAGTCAGGAGGAGGCCTGGTGCAGCCCGGAGGAAGCCTGAGACTG
TCATGCGCCGCCTCAGGGTTCTCATTAACCGACTATGGTGTTCACTGGGTTCGCCAGGCC
CCAGGAAAGGGTCTGGAGTGGCTGGTGGTGATTTGGAGTGATGGAAGCTCAACCTATAAT
TCAGCTCTCAAATCCAGAATGACCATCTCAAAGGACAACGCCAAGAACACCGTGTACTTA
CAGATGAACAGTCTCAGAGCTGAGGACACCGCCGTGTACTACTGTGCCAGACATGGAACT
TACTACGGAATGACTACGACGGGGATGCTTTGGACTACTGGGGTCAAGGAACCCTGGTC
ACCGTCTCCTCAGCTTCCACCAAGGGCCCATCCGTCTTCCCCCTGGCGCCCTGCTCCAGG
AGCACCTCCGAGAGCACAGCCGCCCTGGGCTGCCTGGTCAAGGACTACTTCCCCGAACCG
GTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTG
GGCACGAAGACCTACACCTGCAACGTAGATCACAAGCCCAGCAACACCAAGGTGGACAAG
AGAGTTGAGTCCAAATATGGTCCCCCATGCCCATCATGCCCAGCACCTGAGTTCCTGGGG
GGACCATCAGTCTTCCTGTTCCCCCCAAAACCCAAGGACACTCTCATGATCTCCCGGACC
CCTGAGGTCACGTGCGTGGTGGTGGACGTGAGCCAGGAAGACCCCGAGGTCCAGTTCAAC
TGGTACGTGGATGGCGTGGAGGTGCATAATGCCAAGACAAAGCCGCGGGAGGAGCAGTTC
AACAGCACGTACCGTGTGGTCAGCGTCCTCACCGTCCTGCACCAGGACTGGCTGAACGGC
AAGGAGTACAAGTGCAAGGTCTCCAACAAAGGCCTCCCGTCCTCCATCGAGAAAACCATC
TCCAAAGCCAAAGGGCAGCCCCGAGAGCCACAGGTGTACACCCTGCCCCCATCCCAGGAG
GAGATGACCAAGAACCAGGTCAGCCTGACCTGCCTGGTCAAAGGCTTCTACCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAGGCTAACCGTGGACAAGAGCAGG
TGGCAGGAGGGGAATGTCTTCTCATGCTCCGTGATGCATGAGGCTCTGCACAACCACTAC
ACACAGAAGAGCCTCTCCCTGTCTCTGGGTAAA huM200 COMPLETE LIGHT CHAIN DNA SEQUENCE
(SEQ ID NO: 30)

GAAATTGTTCTCACCCAGTCTCCAGCAACCCTCTCTCTCTCCGGGGGAACGGGCTACC
CTCTCCTGCACTGCCAGTTCAAGTGTCAGTTCCAATTACTTGCACTGGTACCAGCAGAAG
CCAGGACAGGCCCCCCGTCTCCTCATTTATAGCACATCCAACCTGGCTTCTGGAGTCCCA
GCTCGTTTCAGTGGCAGTGGGTCTGGGACCTCTTACACCCTCACAATCAGCAGCCTCGAG
CCAGAAGATTTCGCCGTCTATTACTGCCACCAGTATCTTCGTTCCCCACCGACGTTCGGT
GGAGGCACCAAGGTCGAAATCAAACGAACTGTGGCTGCACCATCTGTCTTCATCTTCCCG
CCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGT

FIGURE 12 huM200 COMPLETE HEAVY CHAIN AMINO ACID SEQUENCE
(SEQ ID NO: 31)

EVQLVESGGGLVQPGGSLRLSCAASGFSLTDYGVHWVRQAPGKGLEWLVVIWSDGSSTYN
SALKSRMTISKDNAKNTVYLQMNSLRAEDTAVYYCARHGTYYGMTTTGDALDYWGQGTLV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPSCPAPEFLG
GPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSR
WQEGNVFSCSVMHEALHNHYTQKSLSLSLGK huM200 COMPLETE LIGHT CHAIN AMINO ACID SEQUENCE
(SEQ ID NO: 32)

EIVLTQSPATLSLSPGERATLSCTASSSVSSNYLHWYQQKPGQAPRLLIYSTSNLASGVPARF
SGSGSGTSYTLTISSLEPEDFAVYYCHQYLRSPPTFGGGTKVEIKRTVAAPSVFIFPPSDEQL
KSGTASVVCLLNNFYPREAKVQWKVDNALQSGNSQESVTEQDSKDSTYSLSSTLTLSKADYEK
HKVYACEVTHQGLSSPVTKSFNRGEC

FIGURE 13

A.
Visualization of Annexin V positive cells by Immunofluorescence
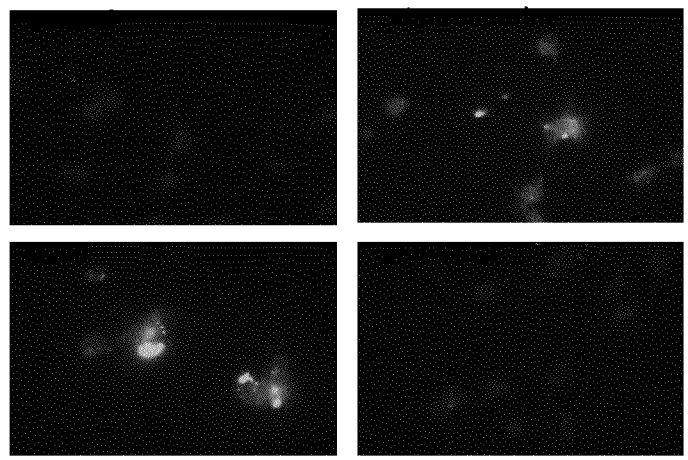
B.
Quantification of Annexin V positive cells by flow cytometry
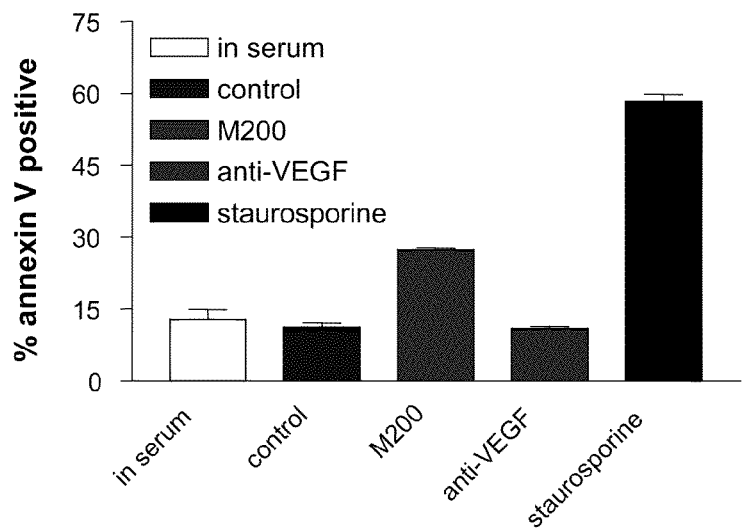
FIG. 16

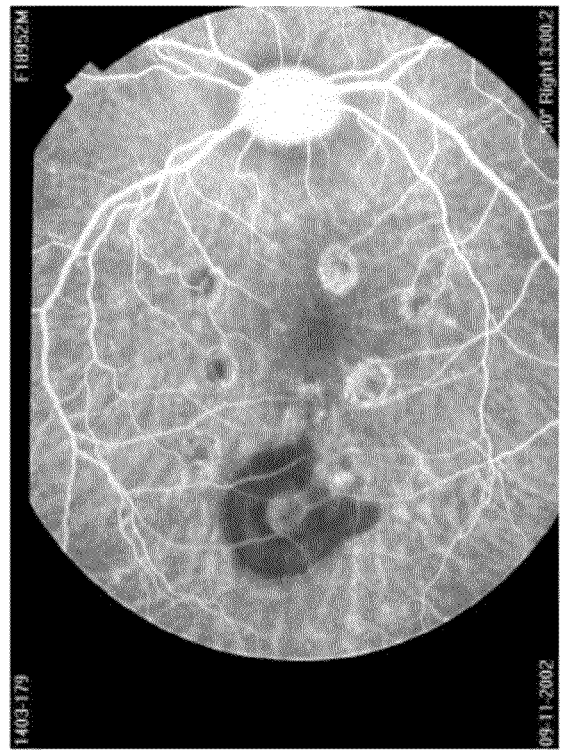
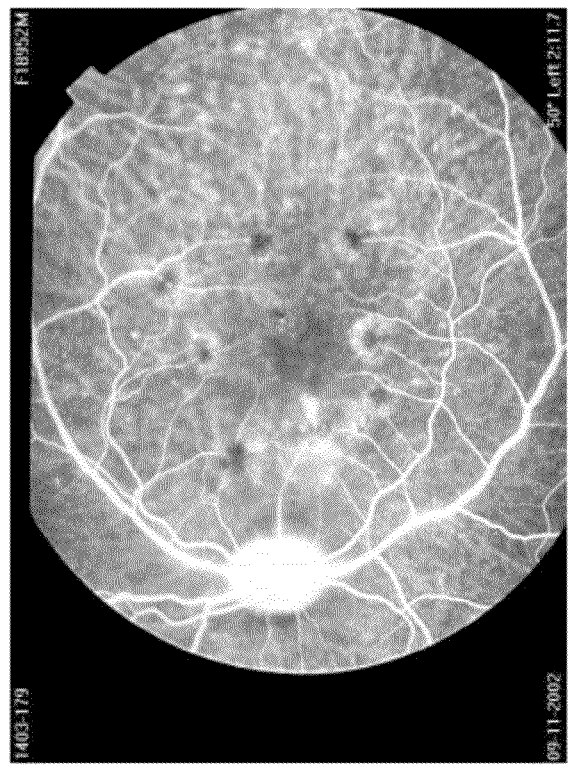
FIG. 20

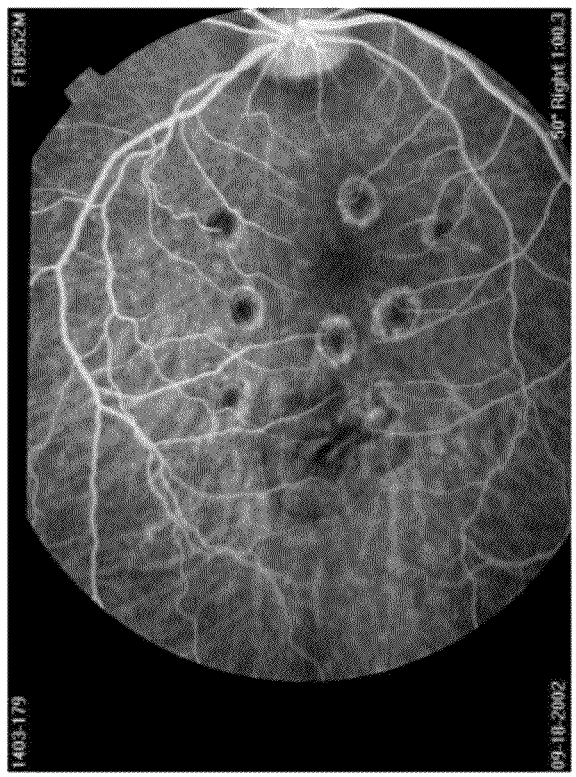
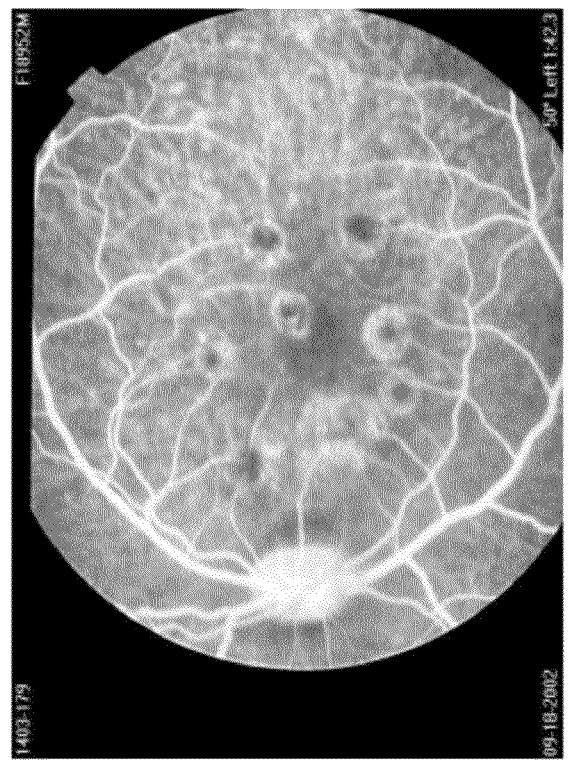
FIG. 21

CHIMERIC AND HUMANIZED ANTIBODIES TO α5β1 INTEGRIN THAT MODULATE ANGIOGENESIS

RELATED APPLICATIONS

This application is a continuation of U.S. application Ser. No. 11/852,147, filed Sep. 7, 2007, which was a continuation of U.S. application Ser. No. 10/724,274, filed Nov. 26, 2003; now U.S. Pat. No. 7,276,589, issued Oct. 2, 2007, which claims priority from U.S. Provisional Application No. 60/429,743, filed Nov. 26, 2002 and U.S. Provisional Application 60/508,149, filed Sep. 30, 2003, each of which is hereby incorporated by reference in its entirety.

FIELD OF THE INVENTION

The present invention provides chimeric and humanized antibodies that specifically recognize α5β1 integrin, and methods for using the antibodies for reducing or inhibiting angiogenesis in a tissue. Also provided are methods of determining therapeutically acceptable doses of the antibodies and pharmaceutical compositions including the same.

BACKGROUND OF THE INVENTION

Angiogenesis is the process whereby new blood vessels are formed. Angiogenesis, also called neovascularization, occurs normally during embryogenesis and development, and occurs in fully developed organisms during wound healing and placental development. In addition, angiogenesis occurs in various pathological conditions including: ocular diseases such as diabetic retinopathy and macular degeneration due to neovascularization; conditions associated with tissue inflammation such as rheumatoid arthritis and inflammatory bowel disease; and cancer, where blood vessel formation in the growing tumor provides oxygen and nutrients to the tumor cells, as well as providing a route via which tumor cells metastasize throughout the body. Since millions of people around the world are afflicted by these diseases, a considerable effort has been made to understand the mechanisms involved in angiogenesis in order to develop methods for detecting and inhibiting such undesirable angiogenesis.

Angiogenesis occurs in response to stimulation by one or more known growth factors, and also may involve other as yet unidentified factors. Endothelial cells, which are the cells that line mature blood vessels, normally do not proliferate. However, in response to an appropriate stimulus, the endothelial cells become activated and begin to proliferate and migrate into unvascularized tissue to form new blood vessels. In some cases, precursor cells are activated to differentiate into endothelial cells, which form new blood vessels.

Blood vessels are surrounded by an extracellular matrix. In addition to stimulation by growth factors, angiogenesis depends on interaction of the endothelial cells with the extracellular matrix, as well as with each other. The activation of endothelial cells by growth factors and the migration into and interaction with the extracellular matrix and with each other is dependent on cell surface receptors expressed by the endothelial cells. These cell surface receptors, which include growth factor receptors and integrins, interact specifically with particular molecules.

In pathological conditions such as age-related macular degeneration and diabetic retinopathy, decreased availability of oxygen to the retina results in a hypoxic condition that stimulates the secretion of angiogenic growth factors such as vascular endothelial growth factors (VEGF). This secretion induces abnormal migration and proliferation of endothelial cells into tissues of the eye. This results in vascularization of ocular tissues and can induce corneal scarring, retinal detachment and fluid accumulation in the choroid, each of which can adversely affect vision and lead to blindness.

Angiogenesis also is associated with the progression and exacerbation of inflammatory diseases, including psoriasis, rheumatoid arthritis, osteoarthritis, and inflammatory bowel diseases such as ulcerative colitis and Crohn's disease. In inflammatory arthritic disease, for example, influx of lymphocytes into the region surrounding the joints stimulates angiogenesis in the synovial lining. This increased vasculature provides a means for greater influx of leukocytes, which facilitates the destruction of cartilage and bone in the joint. Angiogenic vascularization that occurs in inflammatory bowel disease results in similar effects in the bowel.

The growth of capillaries into atherosclerotic plaques in the coronary arteries represents another pathological condition associated with growth factor induced angiogenesis. Excessive blood flow into neovascularized plaques can result in rupture and hemorrhage of the blood-filled plaques, releasing blood clots that can result in coronary thrombosis.

The involvement of angiogenesis in such diverse diseases as cancer, ocular disease and inflammatory diseases has led to an effort to identify methods for specifically inhibiting angiogenesis as a means to treat these diseases. For cancer patients, such methods of treatment can provide a substantial advantage over currently used methods such as chemotherapy, which kill or impair not only the target tumor cells but also normal proliferating cells in the patient, such as blood cells, epithelial cells, and cells lining the intestinal lumen. Such non-specific killing by chemotherapeutic agents results in side effects that are, at best, unpleasant, and can often result in unacceptable patient morbidity, or mortality. In fact, the undesirable side effects associated with cancer therapies often limit the treatment a patient can receive.

BRIEF SUMMARY OF THE INVENTION

The present invention provides therapeutic chimeric and humanized antibodies directed against α5β1 integrin; methods for purification of these antibodies, and methods for their use in treating conditions comprising undesirable tissue angiogenesis.

In one embodiment the invention includes a nucleic acid encoding a polypeptide of a chimeric or humanized anti-α5β1 integrin antibody, having 65%, preferably more than 75%, more preferably 85%, 90%, 95%, 97% or 99% sequence identity to one or more of the amino acid sequences selected from the group consisting of SEQ ID NOS: 1-12, 16, 18, 20, 22, 25-26, 28, 31-32. Most preferably, the nucleic acid encodes a polypeptide of a chimeric or humanized anti-α5β1 integrin antibody comprising an amino acid sequence selected from the group consisting of SEQ ID NOS: 2-6, 8-12, 16, 18, 20, 22, 25-26, 28, 31-32. The peptide encoded by this nucleic acid can be a single-chain antibody or Fab, in addition to a Fab or antibody comprising several peptides bound by disulfide bridges.

The invention also includes a polypeptide having 65%, preferably more than 75%, more preferably 85%, 90%, 95%, 97% or 99% sequence identity to one or more of the amino acid sequences selected from the group consisting of SEQ ID NOS: 1-12, 16, 18, 20, 22, 25-26, 28, 31-32. Most preferably, the nucleic acid encodes a polypeptide comprising one or more of the amino acid sequences selected from the group consisting of SEQ ID NOS: 2-6, 8-12, 16, 18, 20, 22, 25-26, 28, 31-32. These peptides include chimeric, human and humanized antibodies and Fab fragments.

In another embodiment the invention includes chimeric anti-α5β1 integrin antibodies. These antibodies comprise a first polypeptide from a first source comprising an amino acid sequence having a sequence 65%, preferably more than 75%, more preferably 85%, 90%, 95%, 97% or 99% identical to an amino acid sequence selected from the group consisting of SEQ ID NOS: 1, 7, 16, 18, 20, 22; and a second polypeptide from a second source having a sequence 65%, preferably more than 75%, more preferably 85%, 90%, 95%, 97% or 99% identical to a constant region of an antibody of the second source wherein the first and second polypeptides form a protein complex that is immunoreactive with α5β1 integrin. In a preferred embodiment the second source of the constant region is a human IgG. In another preferred embodiment, the constant region is a human IgG4.

In another preferred embodiment, the chimeric antibodies comprise a first polypeptide sequence from a first source comprising one or more amino acid sequences selected from the group consisting of SEQ ID NOS: 1, 7, 16, 18, 20, 22; and a second polypeptide sequence from a second source comprising a constant region sequence of an antibody of the second source wherein the first and second polypeptide sequences form a protein complex that is immunoreactive with α5β1 integrin.

In a most preferred embodiment, the invention includes a chimeric anti-α5β1 integrin antibody comprising the heavy chain amino acid sequence SEQ ID NO: 25 and the light chain amino acid sequence SEQ ID NO: 26.

In an alternative embodiment, the invention includes a nucleic acid encoding a chimeric anti-α5β1 integrin antibody heavy chain variable region comprising SEQ ID NO: 19, and a nucleic acid encoding a chimeric anti-α5β1 integrin antibody heavy chain variable region comprising SEQ ID NO: 21.

In a further preferred embodiment, the invention includes a Fab fragment derived from the chimeric anti-α5β1 integrin antibody comprising heavy chain amino acid sequence SEQ ID NO: 25 and light chain amino acid sequence SEQ ID NO: 26. In a most preferred embodiment, the Fab fragment comprises the heavy chain amino acid sequence SEQ ID NO: 28 and the light chain amino acid sequence SEQ ID NO: 26.

In a further preferred embodiment, the invention includes a humanized antibody derived from the chimeric anti-α5β1 integrin antibody comprising heavy chain amino acid sequence SEQ ID NO: 25 and light chain amino acid sequence SEQ ID NO: 26. In a most preferred embodiment, the humanized antibody comprises the heavy chain amino acid sequence SEQ ID NO: 28 and the light chain amino acid sequence SEQ ID NO: 26.

In another embodiment, the invention includes an expression vector comprising one or more of the nucleic acids selected from the group consisting of SEQ ID NOS: 15, 17, 19, 21, 23, 24, 27, 29, and 30. In a preferred embodiment the expression vector comprises SEQ ID NOS: 19 and 21.

In another embodiment, the invention includes a cell transformed by an expression vector comprising one or more of the nucleic acids selected from the group consisting of SEQ ID NOS: 15, 17, 19, 21, 23, 24, 27, 29, and 30. In a preferred embodiment the expression vector comprises SEQ ID NOS: 19 and 21.

In another embodiment the invention includes pharmaceutical compositions comprising the chimeric or humanized anti-α5β1 integrin antibodies described herein. In some embodiments, these compositions may contain agents that enhance the uptake or localization of the therapeutic component, decrease inflammation, or otherwise provide localized relief.

In one aspect of this embodiment, the pharmaceutical composition comprises a topical cream that is applied directly to the injured tissue. In another aspect, the pharmaceutical is an eye drop solution that is applied directly to the injured eye. In still another aspect is a pharmaceutical that is an injectable that can be applied systemically to treat injured tissue in one or both eyes of an individual or to inhibit neoangiogenesis in tumor tissue.

In another embodiment the invention includes methods of controlling vascularization in injured tissue. These methods comprise applying one or more doses of a chimeric or humanized anti-α5β1 integrin antibody to the injured tissue, where the injury to the tissue can be the result of physical or chemical damage, or disease.

In another embodiment the invention includes a method of administering a therapeutic antibody comprising: providing a pharmaceutical including a therapeutic antibody comprising a variable heavy chain region having a sequence selected from the group consisting of SEQ ID NOS: 2-6, 16, 20 and a variable light chain region independently selected from the group consisting of SEQ ID NOS: 8-12, 18, 22; and applying the therapeutic antibody to an injured tissue. In this embodiment of the invention, the injured tissue responds to injury by increasing its blood flow through neovascularization and the therapeutic antibody inhibits this neovascularization. In one aspect the method involves injecting therapeutic antibodies intravitreally into a diseased or injured eye of an individual who has two afflicted eyes; intravitreal injection of one eye being sufficient to treat both eyes.

In another embodiment the invention includes a process for the purification of anti-α5β1 integrin antibodies. The method comprises absorbing the antibody onto an antibody affinity matrix bound to a substrate and eluting the antibody from the substrate-bound antibody affinity matrix using an eluting solution having a pH of about 3.0 to about 5.5. The process may further comprise recovering the purified antibody. Antibodies amenable to purification using this procedure include those comprising at least two CDR regions selected independently from those present in amino acid SEQ ID NOS: 1-12, 16, 18, 20, and 22. Preferably one of the chosen CDRs is from a $V_L$ chain and the other from a $V_H$ chain.

In some aspects of this purification process the eluting solution has a pH of about 3.3 to about 5.5. In other aspects, the pH of the eluting solution is about 3.5 to about 5.5. Still other aspects comprise an eluting solution with a pH about 3.5 to about 4.2. Further aspects have eluting solutions with a pH in the range of about 4.2 to about 5.5.

Another embodiment of the present invention comprises a method for evaluating physiological effects (e.g. anti-angiogenic properties) modulated by a humanized anti-α5β1 integrin antibody, which includes both antibodies and Fab fragments. This method comprises providing a viable tissue sample capable of vascular regeneration; creating lesions in the viable tissue sufficient to produce choroidal neovascularization; applying one or more doses of a humanized anti-α5β1 integrin antibody to the viable tissue; and monitoring the dosed viable tissue for re-vascularization. In preferred embodiment, the method of evaluation includes eye tissue as the viable tissue. In some embodiments the macula of the eye is used. Also contemplated are methods of evaluating where the eye tissue used is that of a living primate e.g. cynomologous monkey).

In another embodiment, the method of evaluating comprises injecting a chimeric or humanized anti-α5β1 integrin antibody intravitreally. In one aspect of the invention, where two eyes of an individual are injured, injection of the antibodies in one eye results in antibodies contacting injured tissue present in both eyes.

Another aspect of the method for evaluating physiological effects comprises creating lesions by contacting the viable tissue with laser light. This laser light can be from about 300 to about 700 mwatts, and the exposure time is no more than 0.1 seconds, preferably less than 0.05 seconds, and most preferably less than about 0.01 seconds. The lesions should be less than 200 μm, preferably less than 100 μm, more preferably from about 50 to about 100 μm in diameter, and most preferably about 75 to 25 μm in diameter.

Some aspects of the method include a monitoring step comprising periodically photographing the lesions treated by application of one or more doses of a humanized anti-α5β1 integrin antibody. In other aspects, the monitoring step further comprises indirect ophthalmoscopic examination of the posterior chamber of the eye, and biomicroscopic examination of the anterior segment of the eye. In another aspect, the method comprises a monitoring step that includes injecting intravenously a fluorescein dye, and examining the viable tissue by fluorescein angiography.

The method for evaluating physiological effects modulated by a chimeric or humanized anti-α5β1 integrin antibody also includes an aspect wherein the chimeric or humanized anti-α5β1 integrin antibody comprises a variable heavy chain region having a sequence 65%, preferably more than 75%, more preferably 85%, 90%, 95%, 97% or 99% identical to an amino acid sequence selected from the group consisting of SEQ ID NOS: 1-6, 16, 20 and a variable light chain region independently selected and having a sequence 65%, preferably more than 75%, more preferably 85%, 90%, 95%, 97% or 99% identical to an amino acid sequence from the group consisting of SEQ ID NOS: 7-12, 18, 22. Most preferably, the humanized anti-α5β1 integrin antibody comprises a variable heavy chain region having a sequence selected from the group consisting of SEQ ID NOS: 1-6, 16, 20, and a variable light chain region independently selected from the group consisting of SEQ ID NOS: 7-12, 18, 22.

The method for evaluating physiological effects modulated by a chimeric or humanized anti-α5β1 integrin antibody also includes an aspect wherein the chimeric or humanized anti-α5β1 integrin antibody comprises a variable heavy chain region having a sequence selected from the group consisting of SEQ ID NOS: 2-6, 16, 20 and a variable light chain region independently selected from the group consisting of SEQ ID NOS: 8-12, 18, 22.

BRIEF DESCRIPTION OF THE DRAWINGS

FIG. 1 depicts the amino acid sequences (SEQ ID NOS: 1-12) for the variable regions of the heavy ($V_H$) and light chains ($V_L$) of a murine anti-α5β1 integrin antibody (IIA1) and five humanized antibodies derived from the murine original (1.0-5.0)

FIG. 2 depicts an, alignment of the amino acid sequences from FIG. 1 (SEQ ID NOS: 1-12) that highlights sequence substitutions in the five humanized antibodies relative to the murine original (IIA1).

FIG. 3 depicts: (A) IIA1 $V_H$ nucleic acid sequence (SEQ ID NO: 13) and amino acid sequence (SEQ ID NO: 46); (B) IIA1 $V_L$ nucleic acid sequence (SEQ ID NO: 14) and amino acid sequence (SEQ ID NO: 47).

FIG. 4 depicts: (A) Antibody 200-4 $V_H$ nucleic acid sequence (SEQ ID NO: 15) and amino acid sequence (SEQ ID NO: 16); (B) Antibody 200-4 $V_L$ nucleic acid sequence (SEQ ID NO: 17) and amino acid sequence (SEQ ID NO: 18).

FIG. 5 depicts: (A) M200 $V_H$ nucleic acid sequence (SEQ ID NO: 19) and amino acid sequence (SEQ ID NO: 20); (B) M200 $V_L$ nucleic acid sequence (SEQ ID NO: 21) and amino acid sequence (SEQ ID NO: 22).

FIG. 9 depicts the complete M200 heavy chain and light chain DNA sequences (SEQ ID NOS: 23-24).

FIG. 10 depicts the complete M200 heavy chain and light chain amino acid sequences (SEQ ID NOS: 25-26).

FIG. 11 depicts the complete F200 heavy chain DNA and amino acid sequences (SEQ ID NOS: 27-28).

FIG. 12 depicts the complete huM200 heavy chain and light chain DNA sequences (SEQ ID NOS: 29-30).

FIG. 13 depicts the complete huM200 heavy chain and light chain amino acid sequences (SEQ ID NOS: 31-32).

FIG. 16 illustrates results showing: (A), M200 induced cell death visualized by annexin staining; (B) quantification of annexin stained cells by flow cytometry.

FIG. 20 depicts fluorescein angiography images of laser-induced lesions in the left and right eyes of an individual primate at day 13 of treatment with (A) control (left eye) and (B) M200 (right eye).

FIG. 21 depicts fluorescein angiography images of laser-induced lesions in the left and right eyes of an individual primate at day 20 of treatment with (A) control (left eye) and (B) M200 (right eye).

DETAILED DESCRIPTION OF THE INVENTION

I. Definitions

Figure 6:
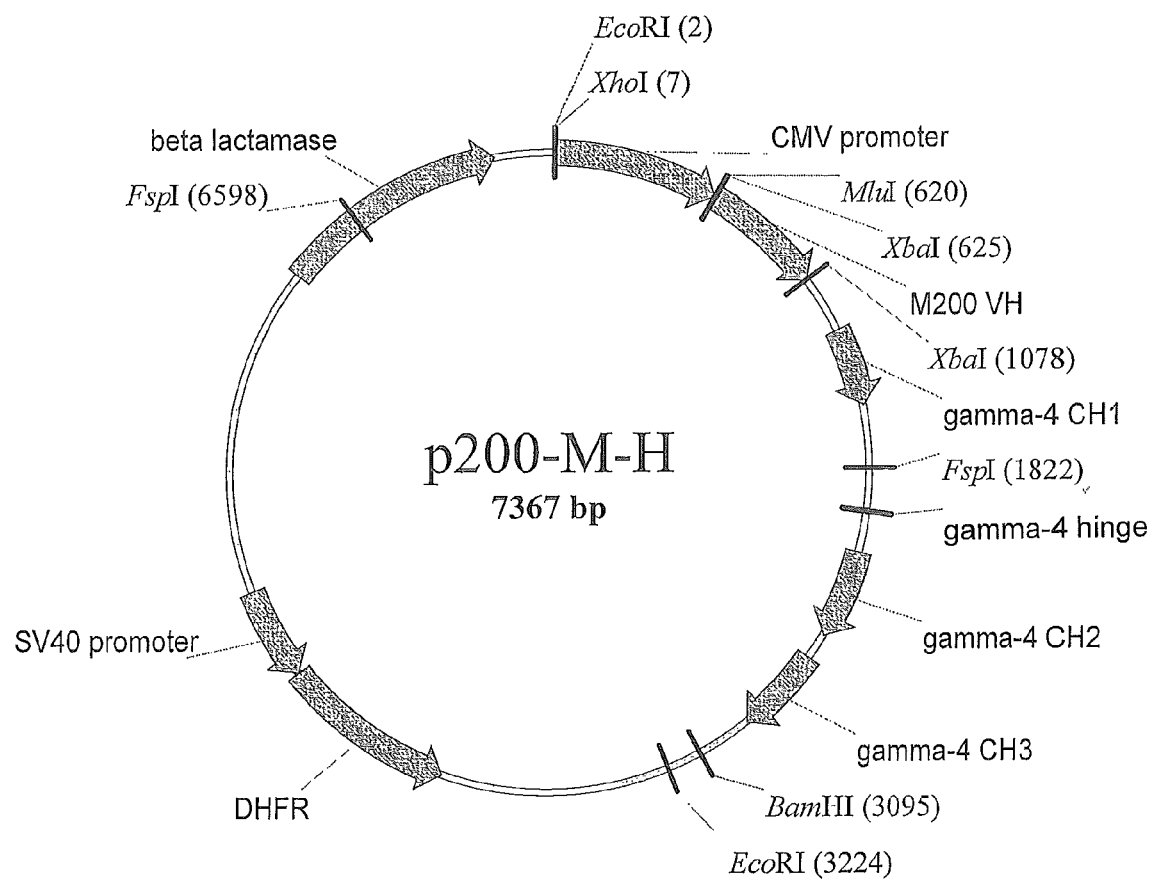
FIG. 6 depicts the p200-M-H plasmid construct for expression of M200 heavy chain.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:*5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" refer to the variable region of an immunoglobulin heavy chain of an antibody, including the heavy chain of an Fv, scFv, or Fab. References to "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fe), typically that of a human immunoglobulin (Jones et al., *Nature* 321:522-525 (1986); Riechmann et al., *Nature* 332: 323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

"pH-sensitive anti-α5β1 integrin antibody" refers to antibodies that specifically recognize α5β1 integrin, and precipitate from solution when subjected to immunopurification using α5β1 integrin as the ligand at neutral or basic pH. pH-sensitive anti-α5β1 integrin antibodies typically comprise two or more CDR sequences chosen independently from any of the $V_H$ or $V_L$ sequences depicted in FIG. 1.

"Angiogenesis" and "neoangiogenesis" refer to the formation of new blood vessels, typically in response to insult, injury or disease. For the purposes of this application, the term "injury," and grammatical variations of the same, includes insult, disease, or other event that results in a tissue response which includes angiogenesis. Angiogenesis also occurs in tumor formation and metastasis, and during embryogenesis, growth and development of higher animals.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Nat'l. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another include e.g.: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, 3H, 14C, 32P, 35S, or 125I.

In some cases, particularly using anti-α5β1 integrin antibodies, the radioisotopes are used as toxic moieties, as described below. The labels may be incorporated into the antibodies at any position. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982). The lifetime of radiolabeled peptides or radiolabeled antibody compositions may extended by the addition of substances that stablize the radiolabeled peptide or antibody and protect it from degradation. Any substance or combination of substances that stablize the radiolabeled peptide or antibody may be used including those substances disclosed in U.S. Pat. No. 5,961,955.

"Antibody affinity matrix" refers to any material capable of preferentially binding an antibody. Antibody affinity matrix materials include polypeptides, polysaccharides, fatty acids, lipids, nucleic acids, including aptamers, or conjugates of these (e.g., glycoproteins, lipoproteins, glycolipids). In certain instances antibody affinity matrix materials can be a macromolecular structure such as a multiprotein complex, a biological membrane or a virus. Other examples of antibody affinity matrix materials are protein A, protein G, lectins, and Fc receptors.

"Protein A" refers to a highly stable surface receptor produced by *Staphylococcus aureus*, which is capable of binding the Fc portion of immunoglobulins, especially IgGs, from a large number of species (Boyle, M. D. P. and K. J. Reis. Bacterial Fc Receptors. Biotechnology 5:697-703 (1987).). One protein A molecule can bind at least 2 molecules of IgG simultaneously (Sjöquist, J., Meloun, B. and Hjelm, H. Protein A isolated from *Staphylococcus aureus* after digestion with lysostaphin. Eur J Biochem 29: 572-578 (1972)).

"Protein G" refers to a cell surface-associated protein from *streptococcus* that binds to IgG with high affinity. It has three highly homologous IgG-binding domains. (See Lian, et al. 1992. Journal of Mol. Biol. 228:1219-1234 and Derrick and Wigley. 1994. Journal of Mol. Biol. 243:906-918.)

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background.

Specific binding to an antibody under such conditions requires an antibody that is selected for its specificity for a particular protein. For example, antibodies raised against a particular protein, polymorphic variants, alleles, orthologs, and conservatively modified variants, or splice variants, or portions thereof, can be selected to obtain only those polyclonal antibodies that are specifically immunoreactive with α5β1 integrin and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, Culture of Animal Cells a Manual of Basic Technique (3rd ed. 1994)).

II. Introduction

The present invention provides chimeric and humanized anti-α5β1 integrin antibodies with improved properties over existing anti-α5β1 integrin antibodies. The present invention also provides pharmaceutical compositions comprising the new antibodies, and improved methods for treating disease states and injuries to tissues that are exacerbated by angiogenesis.

The chimeric and humanized antibodies of the invention have a longer half-life and are less antigenic when administered to a human being than existing forms. The improvement is illustrated diagrammatically in FIG. 2, and involves altering framework and constant regions of murine anti-α5β1 integrin (IIA1) antibodies to "humanize" them.

Humanized antibodies generally have at least three potential advantages for use in human therapy. First, it may interact better with the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

Structurally, humanized antibodies generally have constant and framework (FR) regions that are of human origin, and complementary domain regions (CDRs) that originate from the antibody of the animal in which the anti-α5β1 integrin antibody was raised.

Structurally, chimeric antibodies generally have variable-chain regions originating from the antibody of the animal in which the anti-α5β1 integrin antibody was raised, and constant chain regions of human origin.

Functionally both chimeric and humanized anti-α5β1 integrin antibodies specifically recognize α5β1 integrin, and prevent α5β1 integrin from interacting with its receptor.

Various methods for preparing humanized and chimeric anti-α5β1 integrin antibodies are provided herein. "Humanized" antibodies are generally chimeric or mutant monoclonal antibodies from mouse, rat, hamster, rabbit or other species, bearing human constant and/or variable region domains or specific changes. Techniques for generating "humanized" and "chimeric" anti-α5β1 integrin antibodies are well known to those of skill in the art and may be found in literature reference and patents cited herein.

III. Preparation of Recombinant Chimeric and Humanized Anti-α5β1 Integrin Antibodies, and Fab Fragments Derived Therefrom Antibodies of the present invention are prepared by immunizing an animal with α5β1 integrin, or a peptide derived therefrom to induce anti-α5β1 integrin antibody production. Lymphoid tissue expressing the antibodies is then isolated and the nucleic acids encoding the heavy and light chains of the anti-α5β1 integrin antibodies are purified. The purified nucleic acids are then recombinantly manipulated (according to methods well-known in the art) to create nucleic acids encoding chimeric, humanized, single-chain, Fab or Fab$_2$ antibodies that specifically recognize α5β1 integrin.

The recombinantly manipulated nucleic acids are then used to create anti-α5β1 integrin antibody-producing cells. These cells produce monoclonal antibodies that inhibit, or prevent, α5β1 integrin from binding to its receptor, which results in inhibition of angiogenesis in susceptible tissue.

A. Production of Cells Producing, and Nucleic Acids Encoding, Anti-α5β1 Integrin Antibodies In order to prepare recombinant chimeric and humanized anti-α5β1 integrin antibodies, the nucleic acid encoding non-human anti-α5β1 integrin antibodies must first be isolated. This is typically done by immunizing an animal, for example a mouse, with prepared α5β1 integrin or an antigenic peptide derived therefrom. Typically mice are immunized twice intraperitoneally with approximately 50 micrograms of protein antibody per mouse. Sera from immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymed Corp., San Francisco, Calif. Mice whose sera contain detectable active antibodies according to the invention can be sacrificed three days later and their spleens removed for fusion and hybridoma production. Positive supernatants of such hybridomas can be identified using the assays common to those of skill in the art, for example, Western blot analysis.

The nucleic acids encoding the desired antibody chains can then be isolated by, for example, using hybridoma mRNA or splenic mRNA as a template for PCR amplification of the heavy and light chain genes [Huse, et al., Science 246:1276 (1989)]. Nucleic acids for producing both antibodies and intrabodies can be derived from murine monoclonal hybridomas using this technique [Richardson J. H., et al., Proc Natl Acad Sci USA 92:3137-3141 (1995); Biocca S., et al., Biochem and Biophys Res Comm, 197:422-427 (1993) Mhashilkar, A. M., et al., EMBO J. 14:1542-1551 (1995)]. These hybridomas provide a reliable source of well-characterized reagents for the construction of antibodies and are particularly useful once their epitope reactivity and affinity has been characterized. Isolation of nucleic acids from isolated cells is discussed further in Clackson, T., et al., Nature 352:624-628 (1991) (spleen) and Portolano, S., et al., supra; Barbas, C. F., et al., supra; Marks, J. D., et al., supra; Barbas, C. F., et al., Proc Natl Acad Sci USA 88:7978-7982 (1991) (human peripheral blood lymphocytes).

B. Creating Recombinant Antibodies

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods of generating humanized antibodies are well-known in the art and fully described elsewhere. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Mol. Immunol., 28:489-498 (1991); Studnicka et al., Prot. Eng.

7:805-814 (1994); Roguska et al., Proc. Natl. Acad. Sci. 91:969-973 (1994), and chain shuffling (U.S. Pat. No. 5,565,332), all of which are hereby incorporated by reference in their entireties.

A number of methods have been described to produce recombinant chimeric antibodies. Controlled rearrangement of antibody domains joined through protein disulfide bonds to form chimeric antibodies can be utilized (Konieczny et al., Haematologia, 14(1):95-99, 1981). Recombinant DNA technology can also be used to construct gene fusions between DNA sequences encoding mouse antibody variable light and heavy chain domains and human antibody light and heavy chain constant domains. See e.g., Morrison et al., Proc. Natl. Acad. Sci. USA, 81(21): 6851-6855, 1984; Morrison, Science 229:1202-1207 (1985); Oi et al., BioTechniques 4:214-221 (1986); Gillies et al., J. Immunol. Methods 125:191-202 (1989); U.S. Pat. Nos. 5,807,715; 4,816,567; and 4,816,397, which are incorporated herein by reference in their entireties.

DNA sequences encoding the antigen binding portions or complementarity determining regions (CDR's) of murine monoclonal antibodies can be grafted by molecular means into the DNA sequences encoding the frameworks of human antibody heavy and light chains (Jones et al., Nature, 321 (6069):522-525, 1986.; Riechmann et al., Nature, 332(6162): 323-327, 1988.). The expressed recombinant products are called "reshaped" or humanized antibodies, and comprise the framework of a human antibody light or heavy chain and the antigen recognition portions, CDR's, of a murine monoclonal antibody.

Another method for producing humanized antibodies is described in U.S. Pat. No. 5,639,641, incorporated herein by reference. The method provides, via resurfacing, humanized rodent antibodies that have improved therapeutic efficacy due to the presentation of a human surface in the variable region. In the method: (1) position alignments of a pool of antibody heavy and light chain variable regions is generated to give a set of heavy and light chain variable region framework surface exposed positions, wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity determining regions of the rodent antibody; and (5) the humanized rodent antibody having binding specificity is produced.

A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to the CDR's, amino acids from the donor immunoglobulin framework that are capable of interacting with the CDR's to effect binding affinity, such as one or more amino acids that are immediately adjacent to a CDR in the donor immunoglobulin or those within about 3 Å, as predicted by molecular modeling. The heavy and light chains may each be designed by using any one, any combination, or all of the various position criteria described in U.S. Pat. Nos. 5,693,762; 5,693,761; 5,585,089; and 5,530,101. When combined into an intact antibody, the humanized immunoglobulins are substantially non-antibodyic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries also described in detail herein. In a general sense, the method utilizes sequences from the antigen binding site of an antibody or population of antibodies directed against an antigen of interest. Thus for a single rodent antibody, sequences comprising part of the antigen binding site of the antibody may be combined with diverse repertoires of sequences of human antibodies that can, in combination, create a complete antigen binding site.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. This process has therefore been termed "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. Sequence differences between the rodent component of the selected antibody with human sequences could be minimized by replacing those residues that differ with the residues of human sequences, for example, by site directed mutagenesis of individual residues, or by CDR grafting of entire loops. However, antibodies with entirely human sequences can also be created. EIS therefore offers a method for making partly human or entirely human antibodies that bind to the same epitope as animal or partly human antibodies respectively. In EIS, repertoires of antibody fragments can be displayed on the surface of filamentous phase and the genes encoding fragments with antigen binding activities selected by binding of the phage to antigen.

Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, each incorporated herein by reference.

Techniques described for the production of single chain antibodies (U.S. Pat. No. 4,946,778) can be adapted to produce single chain humanized antibodies to α5β1 integrin.

C. Expressing Recombinant Chimeric or Humanized Antibodies

The resultant antibody can be expressed through one or more vectors comprising nucleic acids encoding the antibody. Preferably the nucleic acid segments encoding the heavy and light chains of the antibody are in a single transcriptional unit, with translation of one of the coding nucleic acids under the control of an IRES sequence. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as *orthopox* or avipox vectors, herpesvirus vectors such as a herpes simplex I virus (HSV) vector [Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990)], Adenovirus Vectors [LeGal LaSalle et al., Science, 259:988 (1993); Davidson, et al., Nat. Genet. 3:219 (1993); Yang, et al., J. Virol. 69:2004 (1995)] and Adeno-associated Virus Vectors [Kaplitt, M. G. et al., Nat. Genet. 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofecton, cell microinjection, and viral vectors.

The vector can be employed to target essentially any desired target cell, such as a glioma. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

D. Isolation and Characterization of Recombinant Antibodies

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to α5β1 integrin protein or peptide, and selection of antibody display libraries in phage or similar vectors (for instance, through use of immobilized or labeled α5β1 integrin protein or peptide).

E. Affinity Purification

Affinity purification of an antibody pool or sera provides a practitioner with a more uniform reagent. Methods for enriching anti-α5β1 integrin antibodies using antibody affinity matrices to form an affinity column are well known in the art and available commercially (AntibodyShop, c/o Statens Serum Institut, Artillerivej 5, Bldg. P2, DK-2300 Copenhagen S). Briefly, an antibody affinity matrix is attached to an affinity support (see e.g.; CNBR Sepharose (R), Pharmacia Biotech). A mixture comprising antibodies is then passed over the affinity matrix, to which the antibodies bind. Bound antibodies are released by techniques common to those familiar with the art, yielding a concentrated antibody pool. The enriched antibody pool can then be used for further immunological studies, some of which are described herein by way of example. Although the antibody affinity matrices used to isolate the antibodies of the present invention are not designed to specifically recognize the anti-α5β1 integrin antibodies of the present invention, this does not limit the utility of the affinity matrices in purifying the antibodies, as the antibodies are expressed as recombinant proteins in systems that are monoclonal in their nature.

Isolated anti-α5β1 integrin antibodies can be used in a competitive binding immunoassay as described above to compare a second protein, thought to be perhaps a variant of α5β1 integrin. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of α5β1 integrin required to inhibit 50% of binding, then the second protein is said to specifically bind to the antibodies generated to the α5β1 integrin.

F. pH-Sensitive Antibody Purification.

Some antibodies of the present invention displayed a propensity to precipitate when affinity purified at neutral or basic pH. To address this issue, another aspect of the invention relates to a process for purification of pH-sensitive antibodies, including the antibodies comprising to the amino acid sequences indicated in FIGS. 1-5, 10, 11 and 13 and chimeric antibodies that include the mouse variable region or have 80% or more sequence identity with the mouse variable region, or having 80% or more sequence identity to the CDR regions of the antibodies included in FIGS. 1-5. The process comprises generally conducting an affinity chromatography for the antibody using a chromatographic column, e.g. an ion exchange column, that contains bound Antibody affinity matrix, followed by elution of the antibody at a pH of from about 3.0 to about 5.5, preferably from about 3.3 to about 5.5, and most preferably either from about 3.5 to about 4.2 or from about 4.2 to about 5.5. Lower pH values within this range are more suitable for small-scale purification while a pH of about 4.2 or higher is considered more suitable for larger scale operations. Operation of the purification process within this range produces a product with little or no aggregation, most preferably with essentially no aggregation.

Affinity chromatography is one means known in the art for isolating or purifying a substance, such as an antibody or other biologically active macromolecule. This is accomplished in general by passing a solution containing the antibody through a chromatographic column that contains one or more ligands that specifically bind to the antibody immobilized on the column. Such groups can extract the antibody from the solution through ligand-affinity reactions. Once that is accomplished, the antibody may be recovered by elution from the column.

This aspect of the invention therefore comprises a method for the purification of anti-α5β1 integrin antibodies using an antibody affinity matrix bound to a substrate, wherein the improvement comprises eluting the antibodies from the substrate-bound antibody affinity matrix using an eluting solution having a pH of from about 3.0 to about 5.5.

More specifically, this aspect of the invention comprises a method for the purification of anti-α5β1 integrin antibodies comprising: (a) absorbing the antibody onto antibody affinity matrix bound to a substrate; and (b) eluting the antibody from the substrate-bound antibody affinity matrix using an eluting solution having a pH of from about 3.0 to about 5.5. In some embodiments, the process also includes the step of (c) recovering the purified antibody.

However, when antibody is to be further purified or treated, then a specific recovery step may not be necessary at this point.

The purification process involves the absorption of the antibodies onto antibody affinity matrix bound to a substrate. Various forms of antibody affinity matrix may be used. The only requirement is that the antibody affinity matrix molecule possesses the ability to bind the antibody that is to be purified. For example, antibody affinity matrix isolated from natural sources, antibody affinity matrix produced by recombinant DNA techniques, modified forms of antibody affinity matrices, or fragments of these materials which retain binding ability for the antibody in question may be employed. Exemplary materials for use as antibody affinity matrices include polypeptides, polysaccharides, fatty acids, lipids, nucleic acid aptamers, glycoproteins, lipoproteins, glycolipids, multiprotein complexes, a biological membrane, viruses, protein A, protein G, lectins, and Fc receptors.

The antibody affinity matrix is attached to a solid phase or support by a general interaction (for example, by non-specific, ion exchange bonding, by hydrophobic/hydrophilic interactions), or by a specific interaction (for example, antigen-antibody interaction), or by covalent bonding between the ligand and the solid phase. Alternately, an intermediate compound or spacer can be attached to the solid phase and the antibody affinity matrix can then be immobilized on the solid phase by attaching the affinity matrix to the spacer. The spacer can itself be a ligand (i.e., a second ligand) that has a specific binding affinity for the free antibody affinity matrix.

The antibody affinity matrix can be attached to various substrates or supports. Typically, ion exchange or coupling (e.g., CNBr-activated) resins are used for this purpose. The antibodies may be adsorbed onto the substrate-bound antibody affinity matrix using various procedures. Preferably, a column procedure is employed, and the antibodies are adsorbed to the column using a buffer solution prepared with an appropriate buffer. Typical buffers and operating conditions are well known in the art.

The antibodies may be eluted from the substrate-bound antibody affinity matrix using conventional procedures, e.g. eluting the antibodies from the column using a buffer solution. To minimize precipitation, pH-sensitive anti-α5β1 integrin antibodies are preferably eluted with a buffer solution comprising 0.1 M glycine at pH 3.5. To minimize degradation and/or denaturation, the temperature of the buffer solution is preferably kept below 10° C., more preferably at or below 4° C. For the same reasons, the period during which the antibodies are exposed to acidic pH should also be minimized. This is accomplished, for example, by adding a predetermined amount of a basic solution to the eluted antibody solution. Preferably this basic solution is a buffered solution, more preferably a volatile basic buffered solution, most preferably an ammonia solution.

The elution of antibodies from the substrate-bound antibody affinity matrix may be monitored by various methods well-known in the art. For example, if column procedures are employed, fractions may be collected from the columns, and the presence of protein determined by measuring the absorption of the fractions. If antibodies of known specificity are being purified, the presence of the antibodies in fractions collected from the columns may be measured by immunoassay techniques, for example, radioimmunoassay (RIA) or enzyme immunoassay (EIA).

The process of the present invention may be performed at any convenient temperature which does not substantially degrade the antibody being purified, or detrimentally affect the antibody affinity matrix bound to a substrate. Preferably, the temperature employed is room temperature. The antibodies eluted from the antibody affinity matrix column may be recovered, if desired, using various methods known in the art.

G. Avidity Testing

Avidity testing allows one skilled in the art to identify antibodies specifically recognizing one or more epitopes of α5β1 integrin. Antibodies are defined to be specifically binding if: 1) they exhibit a threshold level of binding activity, and/or 2) they do not significantly cross-react with related polypeptide molecules. First, antibodies herein specifically bind if they bind to a α5β1 integrin polypeptide, peptide or epitope with a binding affinity ($K_a$) of $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (Scatchard, Ann. NY Acad. Sci. 51: 660-72, 1949), or by surface plasmon resonance using BIAcore.

Second, antibodies specifically bind if they do not significantly cross-react with related polypeptides. Antibodies do not significantly cross-react with related polypeptide molecules, for example, if they detect α5β1 integrin polypeptide but not known related polypeptides using a standard Western blot analysis (Ausubel et al., ibid.). Examples of known related polypeptides are orthologs, proteins from the same species that are members of the integrin family of proteins, the polypeptides shown in alignment FIG. 1, mutant α5β1 integrin polypeptides, and the like. Moreover, antibodies may be "screened against" known related polypeptides to isolate a population that specifically binds to the α5β1 integrin. For example, antibodies raised to human α5β1 integrin polypeptides are adsorbed to related polypeptides adhered to insoluble matrix; antibodies specific to human α5β1 integrin polypeptides will flow through the matrix under the proper buffer conditions. Such screening allows isolation of polyclonal and monoclonal antibodies non-crossreactive to closely related polypeptides (Antibodies: A Laboratory Manual, Harlow and Lane (eds.), Cold Spring Harbor Laboratory Press, 1988; Current Protocols in Immunology, Cooligan, et al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff et al., Adv. in Immunol. 43: 1-98, 1988; Monoclonal Antibodies: Principles and Practice, Goding, J. W. (eds.), Academic Press Ltd., 1996; Benjamin et al., Ann. Rev. Immunol. 2: 67-101, 1984). Representative examples of such assays include: concurrent immunoelectrophoresis, radioimmuno-assay, radioimmuno-precipitation, enzyme-linked immuno-sorbent assay (ELISA), dot blot or Western blot assay, inhibition or competition assay, and sandwich assay. For a review of immunological and immunoassay procedures, see *Basic and Clinical Immunology* (Stites & Terr eds., 7$^{th}$ ed. 1991).

IV. Methods for Measuring Efficacy in Modulating Angiogenesis

The present invention provides methods for evaluating physiological effects modulated by a humanized anti-α5β1 integrin antibody. As a threshold issue, these methods allow screening of compositions comprising the antibodies of the present invention to determine safe, effective therapeutic dosages. During treatment, some of these methods are applicable to monitoring progress, and modulating dosage to provide optimal clinical effect.

The methods comprise providing a viable tissue that is compatible to analysis or treatment; i.e., a tissue that when injured, including immortalization, undergoes undesirable choroidal neovascularization events, which if inhibited or prevented would improve the prognosis of the patient and/or healing of the injured tissue. Typical tissues suitable for treatment or study include tumors and eye tissue, particularly the macula of the eye. The term "tumor" is used broadly herein to mean any new, pathological tissue growth. For purposes of the present invention, a tumor is characterized, in part, by angiogenesis. A tumor can be benign, for example, a hemangioma, glioma, teratoma, and the like, or can be malignant, for example, a carcinoma, sarcoma, glioblastoma, astrocytoma, neuroblastoma, retinoblastoma, and the like. The term "tumor" is used generally to refer to a benign or malignant tumor, and the term "cancer" is used generally to refer to a malignant tumor, which may or may not be metastatic. Malignant tumors that can be diagnosed using a method of the invention include, for example, carcinomas such as lung cancer, breast cancer, prostate cancer, cervical cancer, pancreatic cancer, colon cancer and ovarian cancer; and sarcomas such as osteosarcoma and Kaposi's sarcoma, provided the tumor is characterized, at least in part, by angiogenesis associated with α5β1 expression by the newly forming blood vessels For study, these tissues can be isolated by procedures known and sources readily available to those of skill in the art.

When using a viable tissue for testing the efficacy of the therapeutic antibodies of the present invention, the tissue must first be injured to create lesions and promote choroidal neovascularization. Injury may be accomplished by any suitable means, including mechanical, chemical, or biological means. Exemplary mechanical means of injury include cutting, piercing or clamping. Chemical means include applying agents to the tissue that cause necrosis, apoptosis, or loss of cell to cell contact. Biological means include treatment with infectious agents, such as viruses, bacteria or prions. A preferred method of creating lesions is through the use of a laser. Any laser capable of injuring the tissue may be used, with $CO_2$ gas lasers being a preferred type, a most preferred type being a OcuLight GL (532 nm) Laser Photo-coagulator with a IRIS Medical® Portable Slit Lamp Adaptor. Other laser sources are also suitable provided they can produce laser light from about 300 to about 700 mwatts, and lesions less than 200 μm, preferably less than 100 μm, more preferably from about 50 to about 100 μm in diameter, and most preferably about 75 to 25 μm in diameter. Typically the laser light is applied to the tissue for a fraction of a second. Normally less than 0.5 second, more preferably less than 0.1 second, most preferably less than 0.05 second.

The antibody applied is a chimeric or humanized anti-α5β1 integrin antibody. Preferably, this antibody comprises a variable heavy chain region having a sequence 65%, preferably more than 75%, more preferably 85%, 90%, 95%, 97% or 99% identical to an amino acid sequence selected from the group consisting of SEQ ID NOS.: 1-6, 16 and 20 and a variable light chain region independently selected and having a sequence 65%, preferably more than 75%, more preferably 85%, 90%, 95%, 97% or 99% identical to an amino acid sequence from the group consisting of SEQ ID NOS.: 7-12, 18 and 22. Most preferably, the chimeric or humanized anti-α5β1 integrin antibody comprises a variable heavy chain region having a sequence selected from the group consisting of SEQ ID NOS.: 2-6, 16, 20, 25, 28 and 31 and a variable light chain region independently selected from the group consisting of SEQ ID NOS.: 8-12, 18, 22, 26 and 32.

Antibodies of the present invention can be administered by various routes, for example, intravenously, orally, or directly into the region to be treated, for example, directly into a neoplastic tumor; via eye drops, where the pathological condition involves the eye; or intrasynovially, where the condition involves a joint.

The amount of therapeutic antibody that is administered to an individual will depend, in part, on whether the agent is administered for a diagnostic purpose or for a therapeutic purpose. Methods for determining an effective amount of an agent to administer for a diagnostic or a therapeutic procedure are well known in the art and include phase I, phase II and phase III clinical trials. Using the methods of the present invention, effective amounts can be determined by, for example, titrating dosages to individual test subjects and charting progress as a function of neoangiogenic inhibition.

The total amount of the pharmaceutical that can be administered to a subject as a single dose, either as a bolus or by infusion over a relatively short period of time, or can be administered using a fractionated treatment protocol, in which the multiple doses are administered over a more prolonged period of time. As noted above, one skilled in the art would know that the concentration of a particular agent required to provide an effective amount to a region or regions of angiogenesis associated with α5β1 integrin expression in an individual depends on many factors including the age and general health of the subject, as well as the route of administration, the number of treatments to be administered, and the nature of the pharmaceutical. In view of these factors, the skilled artisan would adjust the particular dose so as to obtain an effective amount for efficaciously interfering with the specific binding of α5β1 integrin with its ligand, thereby allowing for reducing or inhibiting of angiogenesis.

Monitoring of clinically relevant progress is another aspect of the present invention. Monitoring may be carried out by any suitable method known in the art. Preferred methods include microscopy, Nuclear Magnetic Resonance and X-ray. In the case of eye tissue, indirect ophthalmoscopic examination of the posterior chamber of the eye, and biomicroscopic examination of the anterior segment of the eye can be used. A preferred method of monitoring the extent of choroidal neovascularization is by intravenously a fluorescein dye, and examining the viable tissue by fluorescein angiography.

A preferred method of screening the effectiveness of anti-α5β1 integrin antibodies in inhibiting or preventing neo angiogenesis is by creating lesions in the retina of an animal, applying anti-α5β1 integrin antibodies to the lesions, and then monitoring the progression of neoangiogenesis in the damaged tissue relative to suitable control experiments. This approach is discussed in detail in Example 6, below. These studies have led to the surprising finding that application of anti-α5β1 integrin antibodies to one eye of an individual results in treatment of lesions present in both eyes of the individual. It is suggested that newly-formed blood vessels in the injured tissue are "leaky" and results in antibodies applied to one eye entering the systemic blood, which carries them to the other eye. This result holds regardless of whether whole antibodies or Fab fragments are used in the treatment. These results indicate a novel method of treating eye lesions by administering therapeutic anti-α5β1 integrin antibodies of the present invention systemically by, for example, intravenous injection.

V. Therapeutic Uses

An additional embodiment of the invention includes pharmaceutical compositions comprising the therapeutic antibodies described herein. These compositions may contain agents that enhance the uptake or localization of the therapeutic component, decrease inflammation, or otherwise provide localized relief.

The antibodies of the present invention that are useful in reducing or inhibiting angiogenesis associated with α5β1 integrin expression, or a pharmaceutical composition containing the antibodies, can be used for treating any pathological condition that is characterized, at least in part, by angiogenesis. One skilled in the art would know that the agent can be administered by various routes including, for example, orally, or parenterally, including intravenously, intramuscularly, subcutaneously, intraorbitally, intracapsularly, intrasynovially, intraperitoneally, intracisternally or by passive or facilitated absorption through the skin using, for example, a skin patch or transdermal iontophoresis. Furthermore, the antibodies can be administered by injection, intubation, via a suppository, orally or topically, the latter of which can be passive, for example, by direct application of an ointment or powder containing the antibodies, or active, for example, using a nasal spray or inhalant. The antibodies can also be administered as a topical spray, if desirable, in which case one component of the composition is an appropriate propellant. The pharmaceutical composition also can be incorporated, if desired, into liposomes, microspheres or other polymer matrices (Gregoriadis, Liposome Technology, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

Angiogenesis associated with α5β1 integrin expression can occur locally, for example, in the retina of an individual suffering from diabetic retinopathy, or can occur more systemically, for example, in an individual suffering from rheumatoid arthritis or a metastatic malignant neoplasm. Since regions of angiogenesis can be localized or can more systemically dispersed, one skilled in the art would select a particular route and method of administration of the therapeutic antibodies of the present invention based, in part, on this factor.

For example, in an individual suffering from diabetic retinopathy, where angiogenesis associated with α5β1 integrin expression is localized to the retina, the agent may be formulated in a pharmaceutical composition convenient for use as eye drops, which can be administered directly to the eye. In comparison, in an individual suffering from a metastatic carcinoma, the agent in a pharmaceutical composition that can be administered intravenously, orally or by another method that distributes the agent systemically. Thus, antibodies of the present invention can be administered by various routes, for example, intravenously, orally, or directly into the region to be treated, for example, directly into a neoplastic tumor; via eye drops, where the pathological condition involves the eye; or intrasynovially, where the condition involves a joint.

A therapeutic antibody is administered in an effective amount, which is an amount sufficient to interfere with the specific binding of α5β1 integrin to its specific ligand in an individual. Generally, an agent antagonist is administered in a dose of about 0.0001 to 100 mg/kg body weight, though these will vary somewhat with the application. Based on the results of efficacy trials discussed above, the artisan would be able to determine an effective dosage range for a given treatment. Estimates of an amount to be administered can be adjusted accordingly, for example, where the agent is to be administered locally.

A preferred method of administering the antibodies of the present invention is by way of injection, either intradermally, intravenously or directly into the joint or tissue that has suffered an injury. For example, when retinal tissue has been damaged, therapeutic antibodies of the present invention can be injected intravitreally into an affected eye. A surprising result of the present invention is that treatment applied to one eye leads to clinically beneficial effects in both eyes (assuming both eyes are injured). It appears that newly formed blood vessels are "leaky," allowing antibodies applied to the first eye to pass into the blood stream where they are transported to the second eye. When applied to the eye in this manner, the dose is preferably less than 5 µM, more preferably between 0.5 and 2 µM, and most preferably between 0.1 and 1.0 µM. Where indicated, treatment can take the form of multiple doses, given over an area or period of time. Dosage in a multiple format may all be identical, or can be independently determined and applied. This result has also led to an additional method of treating lesions with associated neoangiogenesis comprising systemic application of an effective amount of a therapeutic antibody (for example by intravenous injection) wherein neoangiogenesis of an injured tissue is inhibited or prevented.

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

Example 1

Construction of M200 Chimera from Murine IIA1 Anti-α5β1 Integrin

This example describes construction of the chimeric antibody M200.

A. Starting DNA Sequences of IIA1 and 200-4 VH and VL Domains

The variable heavy ($V_H$) and light ($V_L$) domains of the mouse anti-human α5β1 integrin antibody, IIA1 (Pharmingen, San Diego Calif.) were cloned from the IIA1 hybridoma cDNA and sequenced as part of the initial construction of the 200-4 antibody. FIG. 3 shows the cDNA sequences of the IIA1 $V_H$ (SEQ ID NO: 13) and $V_L$ (SEQ ID NO: 14) domains.

During the construction of the 200-4 mouse/human chimeric IgG4 antibody from IIA1, silent XhoI restriction sites (CTCGAG) (SEQ ID NO: 33) were introduced into the framework 4 regions of both IIA1 $V_H$ and $V_L$. The 200-4 $V_H$ (SEQ ID NO: 15) and $V_L$ (SEQ ID NO: 17) DNA sequences containing these silent XhoI sites, as found in expression constructs DEF38 IIA1/human G4 chimera and NEF5 IIA1/K chimera, are shown in FIG. 4. These 200-4 $V_H$ and $V_L$ sequences were used as the starting point for all subsequent recombinant DNA manipulations.

B. Design of M200 VH and VL Mini-Exons

The 200-4 $V_H$ and $V_L$ domains in expression plasmids DEF38 IIA1/human G4 chimera and NEF5 IIA1/K chimera are directly fused to their adjacent constant domains through silent XhoI sites, with no intervening introns. In order to make these variable domains compatible with the desired antibody expression vectors based on the genomic DNA, it was necessary to design 'mini-exons' which recreate functional donor splice sites at the 3' ends of the variable coding region. Sequence comparisons revealed that the $V_H$ and $V_L$ regions of IIA1 utilized the murine JH4 and JK1 segments, respectively; therefore the mini-exons were designed to recreate natural murine JH4 and JK1 donor splice sites following the last amino acid in the $V_H$ and $V_L$ domains. In addition, the XhoI sites were removed, restoring the framework 4 sequences as found in the original IIA1 hybridoma. The mini-exons were flanked with restriction sites: 5' and 3' XbaI sites (TCTAGA) (SEQ ID NO: 34) for the VH mini-exon, and 5' MluI (ACGCGT) (SEQ ID NO: 35) and 3' XbaI (TCTAGA) (SEQ ID NO: 34) for the VL mini-exon.

Recombinant antibody variable domains occasionally contain undesired alternative mRNA splice sites, which can then give rise to alternately spliced mRNA species. Such sites could, in theory, exist in the murine variable domain but only become active in the context of a heterogeneous expression cell and/or new acceptor sites from chimeric constant regions. Taking advantage of codon degeneracy to remove potential alternative splice sites while leaving the encoded amino acid sequence unchanged may eliminate such undesired alternative splicing. To detect any potential alternative splice sites in the M200 $V_H$ and $V_L$ mini-exons, the initial designs were analyzed with a splice site prediction program from the Center for Biological Sequence Analysis from the Technical University of Denmark (www.cbs.dtu.dk/services/NetGene2/). For both 200-M mini-exons, the correct donor splice sites were identified; however, potential alternative donor splice sites were detected in CDR3 of the $V_H$ mini-exon and CDR1 of the $V_L$ mini-exon. To eliminate the possibility of these splice sites being used, single silent base pair changes were made to the mini-exon designs. In the case of the $V_H$ design, a silent GGT to GGA codon change at glycine 100 (Kabat numbering) was made; for the $V_L$ design, a silent GTA to GTC codon change at valine 29 was made. In both cases these silent changes eliminated the potential secondary splicing donor signal in the V-genes.

Final designs for the M200 $V_H$ and $V_L$ mini-exons (SEQ ID NOS: 19, 21), containing the flanking restriction sites, murine donor splice sites, with the 200-4 XhoI sites removed, and with the potential alternative donor splice sites eliminated are shown in FIG. 5.

C. Construction of M200 $V_H$ Mini-Exon and Plasmid p200-M-H

The designed mini-exon for M200 $V_H$ as shown in FIG. 5A was constructed by PCR-based mutagenesis using 200-4 expression plasmid DEF38 IIA1/human G4 chimera as the starting point. Briefly, the 200-4 $V_H$ region was amplified from DEF38 IIA1/human G4 chimera using primers #110 (5'-TTTTCTAGACCACCATGGCTGTC-CTGGGGCTGCTT-3') (SEQ ID NO: 36), which anneals to the 5' end of the 200-4 $V_H$ signal sequence and appends a Kozak sequence and XbaI site, and primer #104 (5'-TTTTCTAGAGGTTGTGAGGAC TCACCTGAG-GAGACGGTGACTGAGGT-3') (SEQ ID NO: 37) which anneals to the 3' end of the 200-4 $V_H$ and appends an XbaI site. The 469 bp PCR fragment was cloned into pCR4Blunt-TOPO vector (Invitrogen) and confirmed by DNA sequencing to generate plasmid p200M-VH-2.1. This intermediate plasmid was then used in a second PCR mutagenesis reaction to remove the potential aberrant splice site in CDR3 and to add a murine JH4 donor splice site at the 3' end of the $V_H$ coding region. Two complementary primers, #111 (5'-TGGAACT-TACTACGGAATGACTA CGACGGGG-3') (SEQ ID NO: 38) and #112 (5'-CCCCGTCGTAGTCATTCCGTAG-TAAGTTCCA-3') (SEQ ID NO: 39) were designed to direct a GGT to GGA codon change at glycine 100 (Kabat numbering) in CDR3 of the M200 $V_H$. Primers #110 and #112 were used in a PCR reaction to generate a 395 bp fragment from the 5' end of the M200 VH mini-exon, and a separate PCR reaction with primers #111 and #113 (5'-TTTTCTAGAGGC-CATTCTTACCTGAGGAGACGGTGACTGAGGT-3') (SEQ ID NO: 40) generated a 101 bp fragment from the 3' end of the M200 $V_H$ mini-exon. The two PCR products were gel purified on 1.5% low melting point agarose, combined, and joined in a final PCR reaction using primers #110 and #113. The final 465 bp PCR product was purified, digested with XbaI, and cloned into the XbaI-digested and shrimp alkaline phosphatase-treated vector pHuHCg4.D. The final plasmid, p200-M-H (FIG. 6) was subjected to DNA sequencing to ensure the correct sequence for the 200-M $V_H$ mini-exon between the XbaI sites and to verify the correct orientation of the XbaI-XbaI insert.

D. Construction of M200 $V_L$ Mini-Exon and Plasmid P200-M-L

Figure 7:
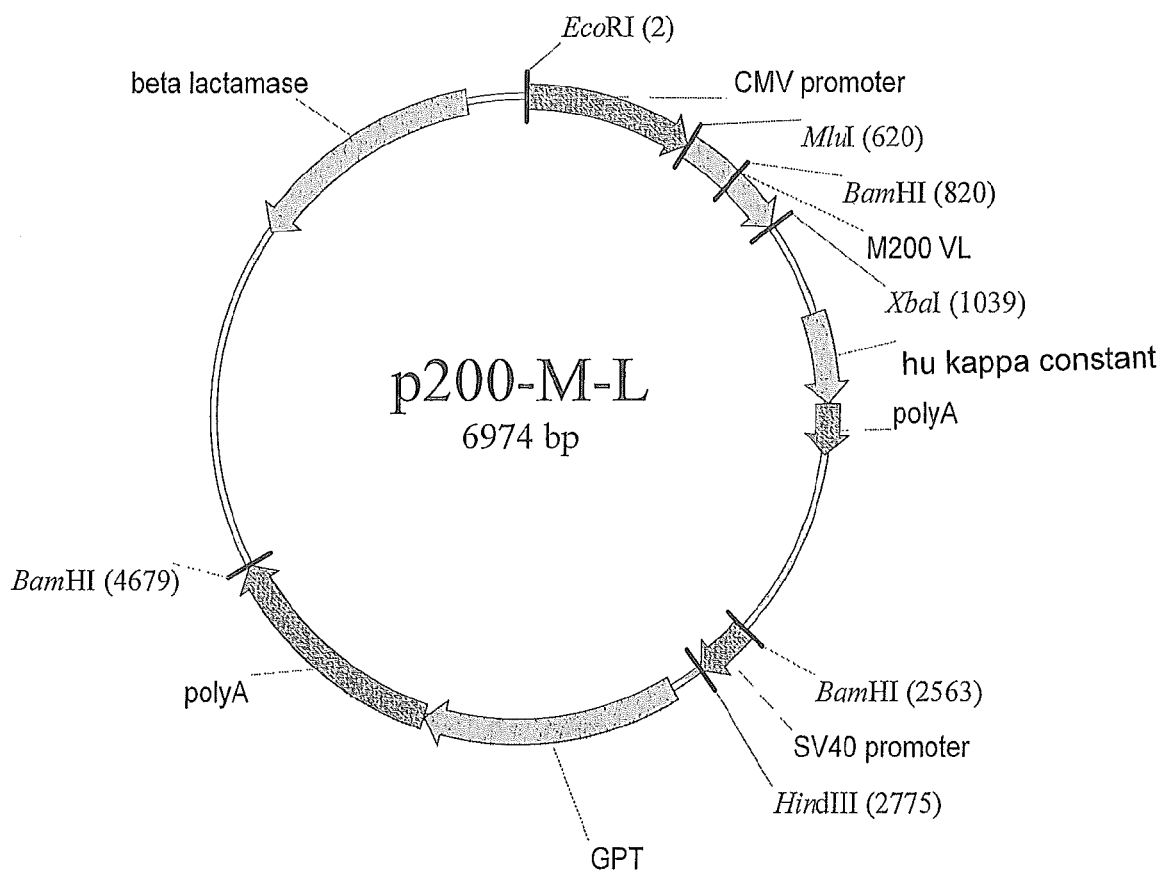
FIG. 7 depicts the p200-M-L plasmid construct for expression of M200 light chain.

The designed mini-exon for M200 $V_L$ as shown in FIG. 5B was constructed by PCR-based mutagenesis using 200-4 expression plasmid NEF5 IIA1/K as the starting point. The $V_L$ region was amplified from NEF5-IIA1-K using primers #101 (5'-TTTACGCGTCC ACCATGGATTTTCAGGTG-CAGATT-3') (SEQ ID NO: 41) which anneals to the 5' end of the signal sequence and appends a Kozak sequence and MluI site, and primer #102 (5'-TTTTCTAGATTAGGAAAG TGCACTTACGTTTGATTTCCAGCTTGGTGCC-3') (SEQ ID NO: 42) which anneals to the 3' end of the 200-4 $V_L$ and appends an XbaI site. The 432 bp PCR fragment was cloned into pCR4Blunt-TOPO vector (Invitrogen) and confirmed by DNA sequencing to generate plasmid p200M-VL-3.3. This intermediate plasmid was then used in a second PCR mutagenesis reaction to remove the potential aberrant splice site in CDR1 and to add a murine JK1 donor splice site at the 3' end of the $V_L$ coding region. Two complementary primers, #114 (5'-TGCCAGTTCAAGTGTCAGTTCCAAT-TACTTG-3') (SEQ ID NO: 43) and #115 (5'-CAAGTAAT-TGGAACTGACACTTGA ACTGGCA-3') (SEQ ID NO: 44) were designed to direct a GTA to GTC codon change at valine 29 (Kabat numbering) in CDR1 of the $V_L$ domain. Primers #101 and #115 were used in a PCR reaction to generate a 182 bp fragment from the 5' end of the $V_L$ mini-exon, and a separate PCR reaction with primers #114 and #116 (5'-TTTTCTAGACTTTGGATTCTACTTAC GTTTGATTTC-CAGCTTGGTGCC-3') (SEQ ID NO: 45) generated a 280 bp fragment from the 3' end of the $V_L$ mini-exon. The two PCR products were gel purified on 1.5% low melting point agarose, combined, and joined in a final PCR reaction using primers #101 and #116. The final 431 bp PCR product was purified, digested with MluI and XbaL and cloned into MluI- and XbaI-digested light chain expression vector pHuCkappa.rgpt.dE. The final plasmid, p200-M-L (FIG. 7) was subjected to DNA sequencing to ensure the correct sequence for the VL mini-exon between the MluI and XbaI sites.

Figure 8:
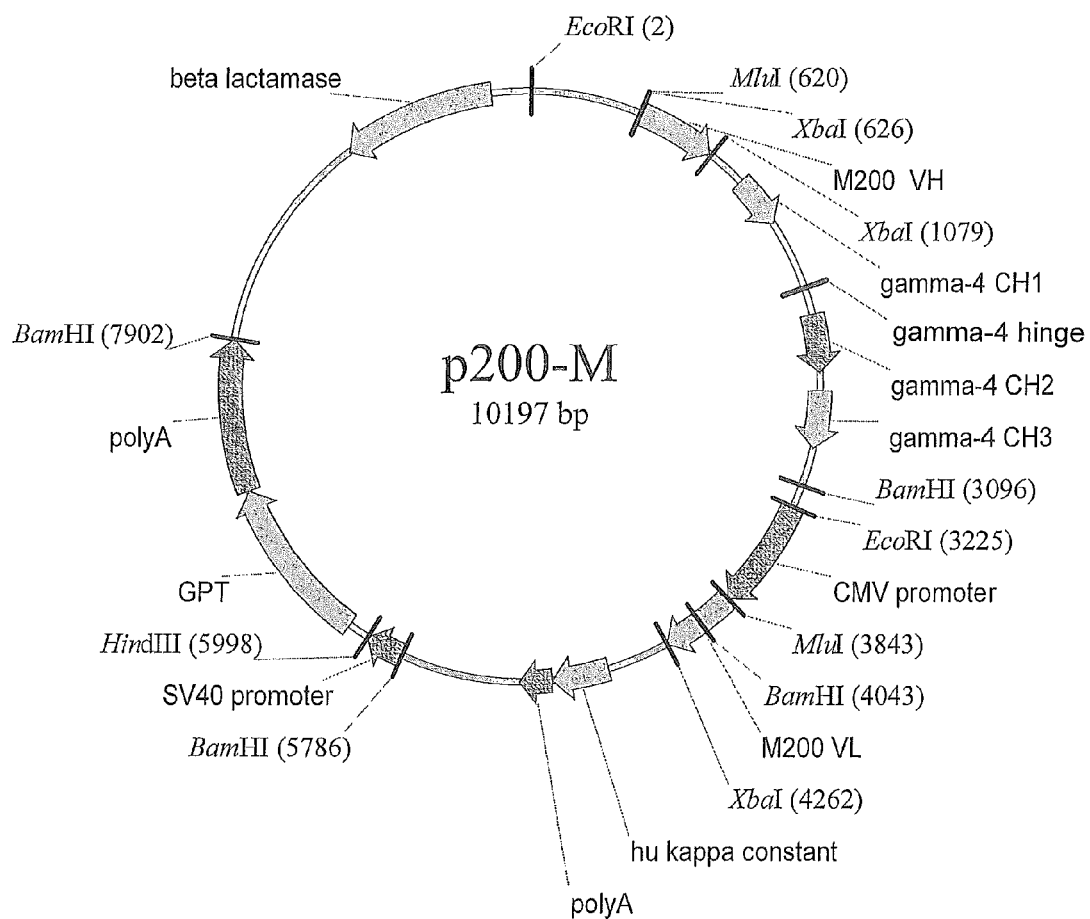
FIG. 8 depicts the single plasmid p200-M for expression of M200 heavy and light chains.

E. Combination of Plasmids p200-M-H and P200-M-L to Make Final Expression Plasmid p200-M To express M200 from a single plasmid, p200-M-H and p200-M-L were digested with EcoRI, and the EcoRI fragment carrying the entire IgG4 heavy chain gene from p200-M-H was ligated into EcoRI-linearized p200-M-L to generate plasmid p200-M (FIG. 8). A large scale endotoxin-free plasmid preparation of p200-M was prepared from 2.5 liters of *E. coli* culture using the Endotoxin-Free Plasmid Maxi-prep Kit (Qiagen). The plasmid structure was verified by restriction enzyme mapping with enzymes BamHI, XbaI, and FspI. The entire coding region for M200 $V_H$, $V_L$, Cκ, and Cγ4 were verified by DNA sequencing. The DNA sequences for the complete M200 heavy (SEQ ID NO: 23) and M200 light (SEQ ID NO: 24) chains are shown in FIG. 9. The corresponding amino acid sequences for the complete M200 heavy (SEQ ID NO: 25) and M200 light (SEQ ID NO: 26) chains are shown in FIG. 10.

Example 2

Generation of Fab Fragment F200 from M200

This example describes making Fab fragment F200.

Fab fragments are generated from M200 IgG starting material by enzymatic digest. The starting IgG is buffer exchanged into 20 mM sodium phosphate, 20 mM N-acetyl cysteine pH 7.0. Soluble papain enzyme is added, and the mixture is rotated at 37° C. for 4 hours. After digestion the mixture is passed over a protein A column to remove Fc fragments and undigested IgG are removed. Sodium tetrathionate is added to 10 mM and incubated for 30 minutes at room temperature. Finally, this preparation is buffer exchanged into 20 mM sodium phosphate, 100 mM sodium chloride, pH 7.4, to yield the F200 solution.

Because it is a Fab fragment, the F200 light chain DNA and amino acid sequences are the same as the M200 light chain. The complete F200 heavy chain DNA (SEQ ID NO: 27) and amino acid (SEQ ID NO: 28) sequences are shown in FIG. 11.

Example 3

In Vitro Inhibition of Endothelial Proliferation by M200

This example describes the effect of the M200 antibody on endothelial proliferation. M200 is a highly specific functional blocking monoclonal antibody against α5β1 integrin.

Figure 14:
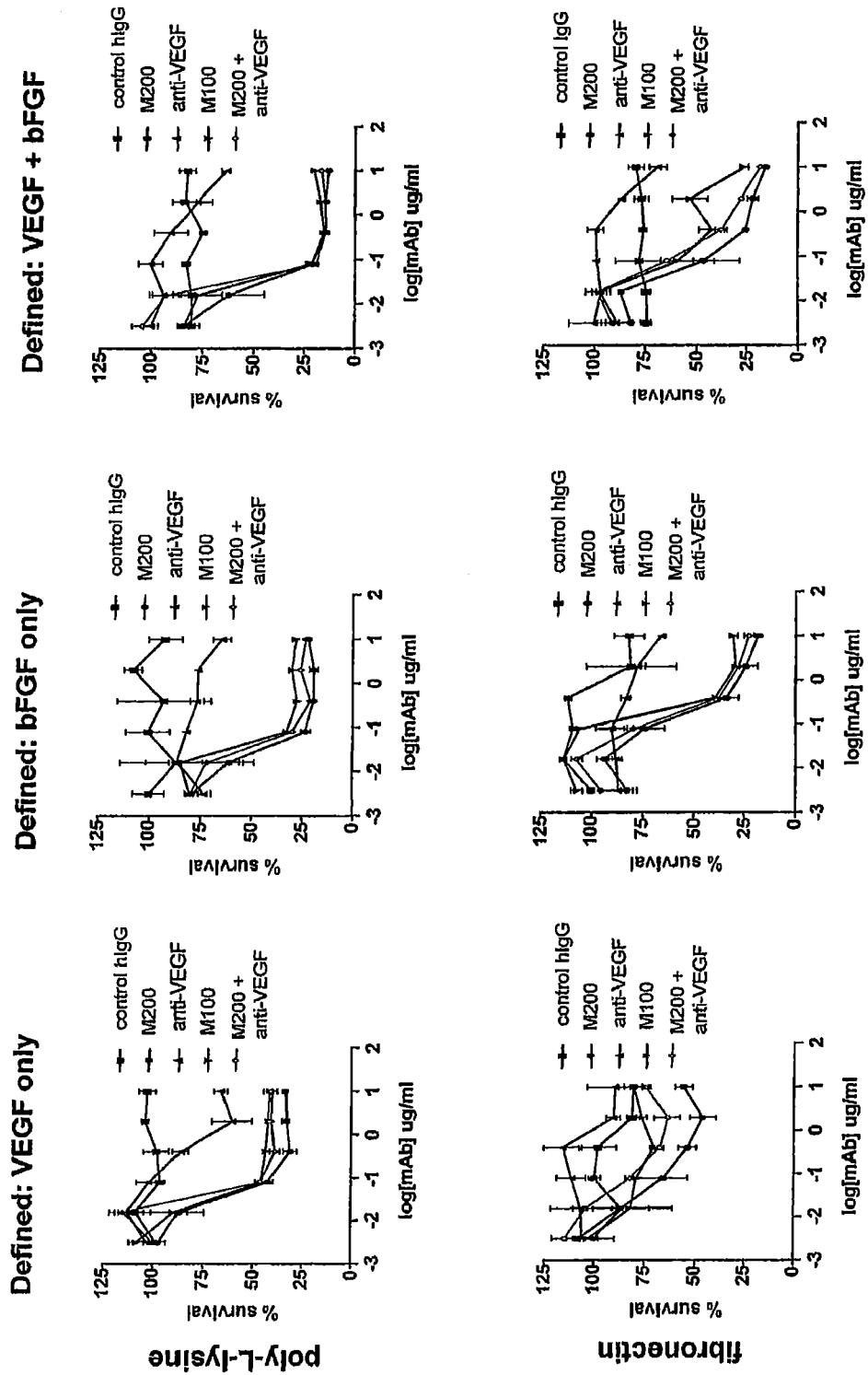
FIG. 14 illustrates results of M200 is a potent inhibitor of endothelial cell growth, encompassing the anti-proliferative properties of an anti-VEGF mAb, HuMV833.

HUVEC were seeded in 96-well plates at a density of 5000 cells/well in the presence of various antibodies (M100, M200, anti-VEGF or control IgG) at the concentrations shown FIG. 14. Plates were pre-treated with either 10 μg/mL fibronectin or 0.1% poly-L-lysine (PLL) and blocked with 2% heat denatured BSA. Cells were grown in defined, serum-free medium containing approximately 2 ng/ml VEGF, bFGF or both. Four days after plating, total cell viability was assessed by using the tetrazolium salt, MTT (3-(4,5-dimethylthiazol-2-yl)-2,5-diphenyl-tetrazoliumbromide+++) assay (see e.g. Wasserman & Twentyman, "Use of a colorimetric microtiter (MTT) assay in determining the radiosensitivity of cells from murine solid tumors," Int. J. Radiat. Oncol. Biol. Phys. 15(3): 699-702 (1988); Romijn, J C, Verkoelen, C F, Schroeder, F H, "Application of the MTT assay to human prostate cancer cell lines in vitro: establishment of test conditions and assessment of hormone-stimulated growth and drug-induced cytostatic and cytotoxic effects," Prostate 12(1): 99-110 (1988)). Data were subtracted for background and normalized to a control devoid of antibody. Each data point was collected in triplicate and the data shown is representative of three individual experiments.

As shown in FIG. 14, HUVEC growth was inhibited by M200 in a dose dependent manner on both PLL and fibronectin (0.40 nM; max inhibition of 80%), whereas the control IgG had no effect. Furthermore, M100 (the mouse antibody from which M200 was derived) shows an identical ability to inhibit cell growth.

Importantly, as shown in FIG. 14, the high-affinity, function blocking anti-VEGF mAb, HuMV833 ($K_D$=5.84×10$^{-11}$ nM), exerted significantly less inhibition of HUVEC growth under all conditions tested (45 nM; max inhibition of 40%). Challenging the cells with M200 and HuMV833 together resulted in no increased inhibitory response.

Figure 15:
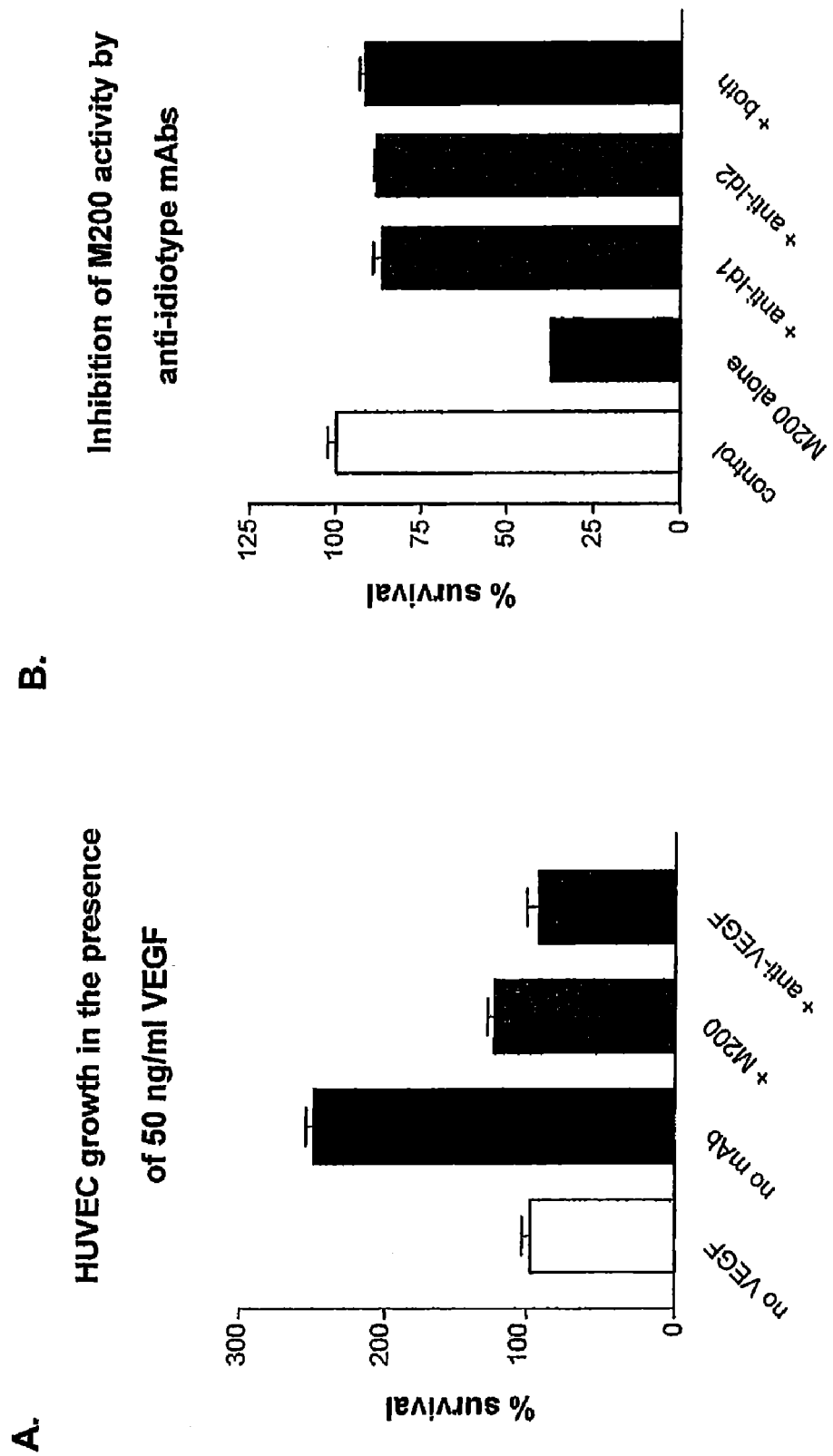
FIG. 15 illustrates results showing that M200 inhibits VEGF induced cell growth and inhibition of the M200 activity by anti-idiotype mAbs.

For the data shown in FIG. 15A, a higher concentration of VEGF (50 ng/ml) was included in the HUVEC proliferation assay on fibronectin as described above. As shown in FIG. 15A, HUVEC proliferation on fibronectin stimulated by VEGF is inhibited by M200 to a similar extent as by HuMV833. Thus, M200-mediated cytostatic effects were evident even at elevated, growth-stimulatory levels of VEGF (50 ng/ml).

Two high affinity antibodies were raised against the M200 idiotype region and determined to block binding of M200 to α5β1 integrin. The two anti-idiotype mAbs (10 μg/ml) were included in the HUVEC proliferation assay described above and assessed for an effect on M200-dependent inhibition of HUVEC growth. Both mAbs are able to inhibit the capacity of a M200 (1 μg/ml) to inhibit HUVEC proliferation. As shown in 15B, the inhibitory activity of M200 was completely reversed by the anti-idiotype mAbs to M200.

Taken together, these results suggest that M200 inhibits HUVEC proliferation through a mechanism overlapping that of the anti-VEGF antibody HuMV833 yet also distinct in some aspects.

Example 4

M200 Effect on Endothelial Cell Survival

This example describes the effect of M200 antibody on endothelial cell survival.

Antibodies against certain integrins are capable of inducing cell death in vitro and in vivo. Recently, a function blocking α5β1 mAb was shown to promote apoptosis in cultured human endothelial cells as measured by annexin V staining, caspase-3 cleavage and DNA fragmentation (Kim, et al., 2002).

Similar annexin V staining was carried out on HUVEC grown exposed to M200 or HuMV833. HUVEC grown in serum-free medium (containing VEGF and bFGF, except where indicated) were grown in the presence of M200 (10 μg/ml), HuMV833 (10 μg/ml) or staurosporine (5 μM; positive control). Cell death was assessed by staining with Annexin V-alexa488 (green), and Hoechst 33258 (blue), followed by fluorescence microscopy (fluorescence microscopy images shown in FIG. 16A). In parallel, cell death was followed by flow cytometry 16 hours after plating (FIG. 16B).

As shown in FIGS. 16A and 16B, cells challenged with M200 displayed increased annexin V staining whereas those challenged with HuMV833 did not. Thus, M200, in contrast to HuMV833, appears to promote cell death in endothelial cells.

In addition, the effect of M200 was compared for senescent versus proliferating cells. HUVEC were plated and allowed to proliferate in the presence of serum and growth factors (middle panel), grown to confluency (left panel) or deprived of serum and growth factors after log phase growth (right panel). In each case, cells were left untreated (control) or incubated with M200 (10 μg/ml) or staurosporine (5 μM) for 16 hours and stained with Annexin V-alexa488.

Figure 17:
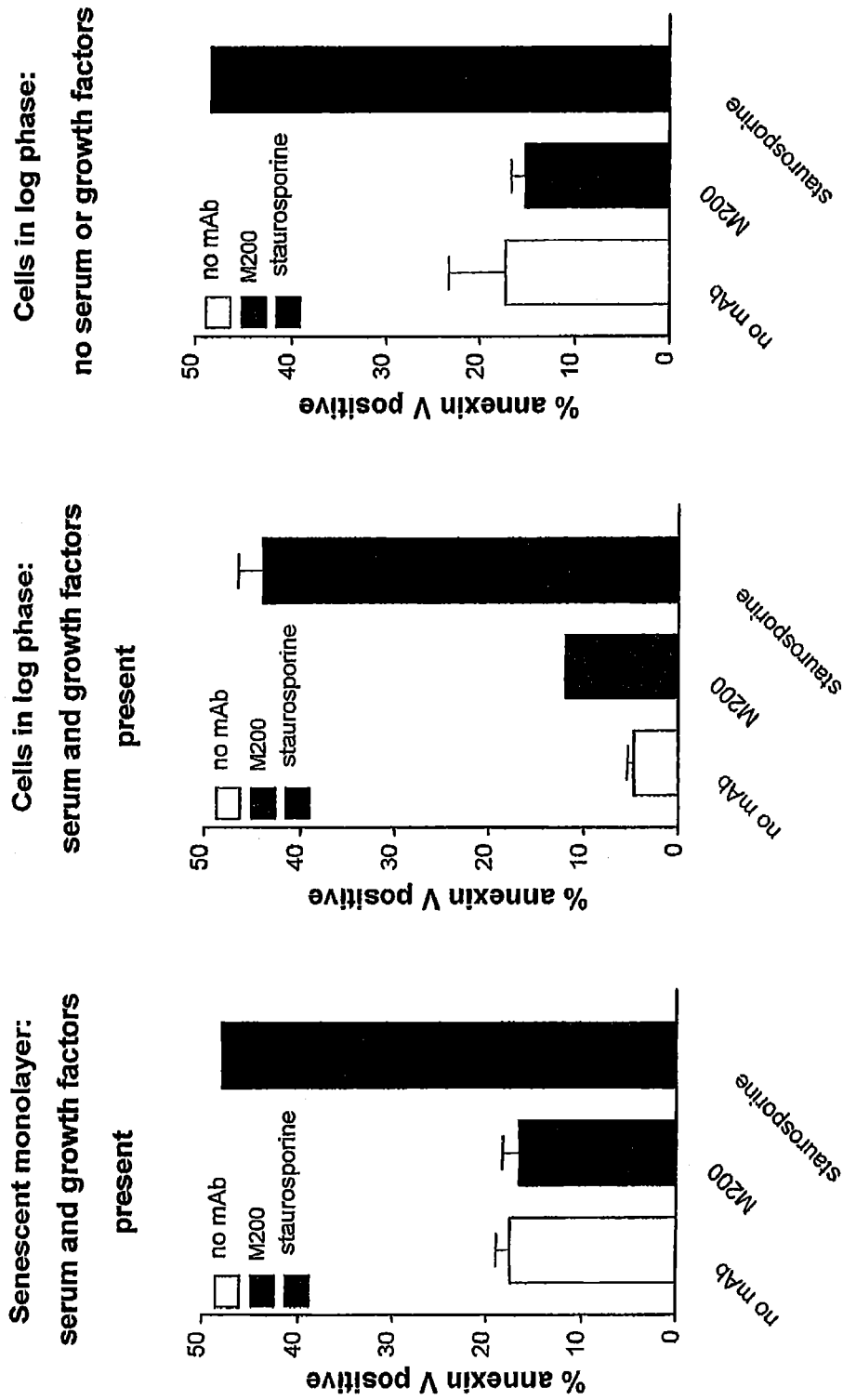
FIG. 17 illustrates results showing M200 causes increased cell death in proliferating versus senescent HUVEC.

As shown in FIG. 17, M200 induced cell death in dividing HUVEC, but not HUVEC brought to senescence by either contact inhibition or growth factor withdrawal. These results suggest that M200 selectively promotes cell death in proliferating endothelial cells.

Example 5

Inhibition of In Vitro Tube Formation F200

Figure 18:
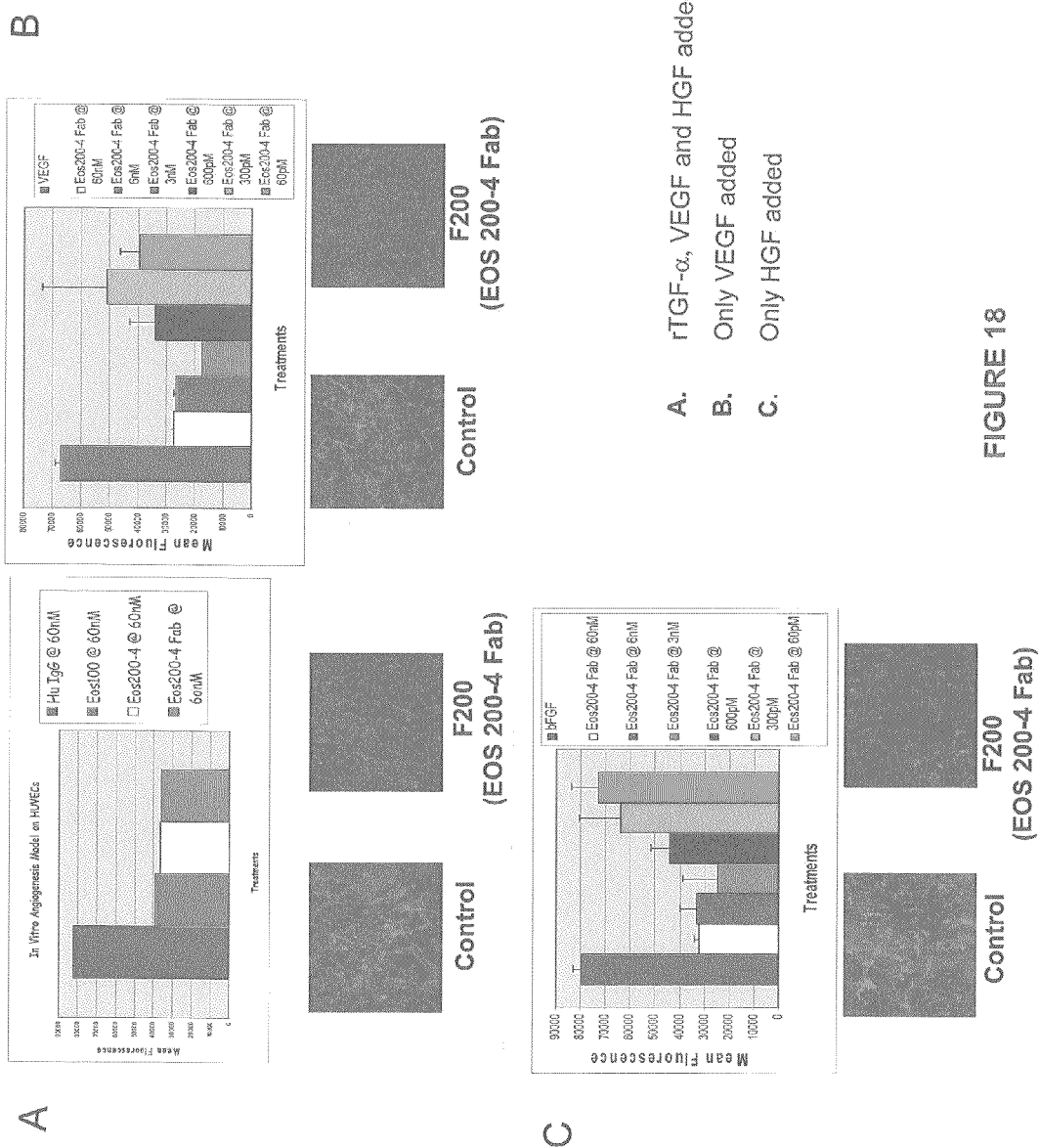
FIG. 18 depicts results of in vitro tube formation assay for inhibition of angiogenesis by F200.

This example describes a tube formation assay demonstrating in vitro inhibition angiogenesis by F200. HUVECs were mixed as a single cell suspension into a fibrin clot (prepared from fibrinogen and a-thrombin) together with human serum and a mixture of growth factors (assay in FIG. 18A included media supplemented with 0.01 mg/ml rTGF-α and 0.1 mg/ml of both VEGF and HGF; assay in FIG. 18B included media supplemented with 0.1 mg/ml VEGF alone; and assay in FIG. 18C included media supplemented with 0.1 mg/ml bFGF alone). Test antibody was added to the media at the indicated concentrations. Over a period of 96 hours, the single cell HUVECs begin to migrate, make contact with other cells and the matrix, form cords and finally 3-dimensional tube-like structures. The extent of tube formation was quantified after 6 days by fixation with 4% formaldehyde and stained with Alexa488~phalloidin. As shown by the images and graphs of mean fluorescence depicted in FIG. 18, tube formation was significantly inhibited by the presence of F200. Tube formation inhibition was observed in the presence of the growth factors, VEGF, HGF and a mixture of these two with rTGFα.

Example 6

In Vivo Inhibition of CNV in Primate Eyes by M200 and F200

This example describes the effect of M200 and F200 Fab on vascular development after laser insult to the maculae of primate eyes. Background literature describing studies of choroidal neovascularization in animal models include: S. Ryan, "The Development of an Experimental Model of Subretinal Neovascularization in Disciform Macular Degeneration," *Transactions of the American Ophthalmological Society* 77: 707-745 (1979); S. J. Ryan, "Subretinal Neovascularization: Natural History of an Experimental Model," *Archives of Ophthalmology* 100: 1804-1809 (1982); M. J. Tolentino et al., "Angiography of Fluoresceinated Anti-Vascular Endothelial Growth Factor Antibody and Dextrans in Experimental Choroidal Neovascularization," *Archives of Ophthalmology* 118: 78-84 (2000).

A. Experimental Design

A total of 8 monkeys were assigned to treatment groups as shown in the table below.

| Group | N | Test Article (left eye) | Test Article (right eye) |
|---|---|---|---|
| 1 | 2 | Untreated | Buffer (50 μl) |
| 2 | 2 | M200 (1 μM; 50 μL) | M200 (1 μM; 50 μL) |
| 3 | 2 | F200 (1 μM; 50 μL) | F200 (1 μM; 50 μL) |
| 4 | 1 | Control (Rituxan 1 μM; 50 μL) | M200 (1 μM; 50 μL) |
| 5 | 1 | Control (Rituxan 1 μM; 50 μL) | F200 (1 μM; 50 μL) |

M200 and F200 were administered in a carrier buffer solution. Rituxan was used as the control dose. Choroidal neovascularization (CNV) was induced on Day 1 bp laser treatment to the maculae of both eyes of each animal as described below. All animals were dosed with M200, F200, or Control as indicated in the table once weekly for 4 weeks. The first day of dosing was designated Day 1. The animals were evaluated for changes in clinical signs, body weight, and other parameters, using standard techniques. All animals were euthanized on Day 28.

B. Laser Induction of Choroidal Neovascularization (CNV)

The animals were fasted overnight prior to laser treatment and dosing. The animals were sedated with ketamine HCl (intramuscular, to effect) followed by a combination of intravenous ketamine and diazepam (to effect) for the laser treatment and dosing procedure.

Choroidal neovascularization (CNV) was induced by laser treatment to the maculae of both eyes. Lesions were placed in the macula in a standard 9-spot grid pattern with a laser [OcuLight GL (532 nm) Laser Photo-coagulator with an IRIS Medical® Portable Slit Lamp Adaptor]. Laser spots in the right eye mirror placement in the left eye. The approximate laser parameters were as follows: spot size: 50-100 μm; laser power: 300-700 milliwatts; exposure time: 0.1 seconds. Parameters for each animal were recorded on the day of laser treatment. Photographs were taken using a TRC-50EX Retina Camera and/or SL-4ED Slit Lamp, with digital CCD camera.

C. Dosing

An intravitreal injection of immunoglobulin (test) or control article was performed in each eye. Injection on Day 1 occurs immediately following laser treatment. Prior to dose administration, a mydriatic (1% tropicamide) was instilled in each eye. Eyes were rinsed with a dilute antiseptic solution (5% Betadine solution or equivalent), the antiseptic was rinsed off with 0.9% sterile saline solution (or equivalent) and two drops of a topical anesthetic (proparacaine or equivalent) was instilled in the eye. A lid speculum was inserted to keep the lids open during the procedure and the globe was retracted. The needle of the dose syringe was passed through the sclera and pars plana approximately 4 mm posterior to the limbus. The needle was directed posterior to the lens into the mid-vitreous. Test article was slowly injected into the vitreous. Forceps were used to grasp the conjunctiva surrounding the syringe prior to needle withdrawal. The conjunctiva was held with the forceps during and briefly following needle withdrawal. The lid speculum was then removed. Immediately following dosing, the eyes were examined with an indirect ophthalmoscope to identify any visible post-dosing problems. A topical antibiotic (TOBREX® or equivalent) can be dispensed onto each eye to prevent infection immediately following dosing and one day after dosing. The animals were returned to their cages when sufficiently recovered from the anesthetic.

Dosing was done on a weekly basis following the schedule in the table below:

| Group No. | Number of Animals (M/F) | Test Article (left eye) | Dose Level | Test Article (right eye) | Dose Level | Dose Volume (μL/eye) |
|---|---|---|---|---|---|---|
| 1 | 1/1 | none | NA | Buffer | 0 | 50 |
| 2 | 1/1 | M200 | 300 μg | M200 | 300 μg | 50 |
| 3 | 1/1 | F200 | 100 μg | F200 | 100 μg | 50 |
| 4 | 1/0 | Control | 100 μg | M200 | 300 μg | 50 |
| 5 | 1/0 | Control | 100 μg | F200 | 100 μg | 50 |

The gram amount dose levels indicated were for each eye. Assuming an average eye volume of 2 ml, the dose per eye was ~150 m/ml M200 and ~50 μg/ml F200. In both cases, the molar concentration of M200 or F200 was 1 μM.

D. Monitoring Inhibition of Angiogenesis

Indirect ophthalmoscopy was used to examine the posterior chamber, and biomicroscopy was used to exam the anterior segment of the eye. The eyes were scored using standard procedures (Robert B. Hackett, and T. O. McDonald, *Dermatotoxicology*, 5th Edition, Eds. F. B. Marzulli and H. I. Maibach, Hemisphere Publishing Corp., Washington, D.C., 1996).

Fluorescein angiography was performed prior to lesion formation and 5, 12, 19 and 26 days subsequent to lesions and initial treatment. A combination of ketamine and diazepam (approximately 10 mg/kg ketamine and 0.5 mg/kg diazepam, intravenously) can be given to maintain sedation. Lid speculums were used to retract the eyelids. Prior to administration of fluorescein dye, each animal was placed in an ophthalmology chair that will maintain the position of the head during photography. Photographs were taken, using a fundus camera (TRC-50EX Retina Camera). Images captured using the TOPCON IMAGEnet™ system. Fluorescein dye (10% fluorescein sodium, approximately 0.1 mL/kg) was injected via a cephalic or saphenous vein. Color and black-and-white photographs were taken at several time points following dye injection, including the arterial phase, early arteriovenous phase and several late arteriovenous phases in order to monitor leakage of fluorescein associated with CNV lesions. The unchanged images can be transferred to compact discs for storage and shipment.

In addition, the eyes may be photographed (TRC-50EX Retina Camera and/or SL-4ED Slit Lamp, with digital CCD camera). The animals may be lightly sedated with ketamine HCl prior to this procedure, and a few drops of a mydriatic solution (typically 1% tropicamide) were instilled into each eye to facilitate the examination.

E. Results

Figure 19:
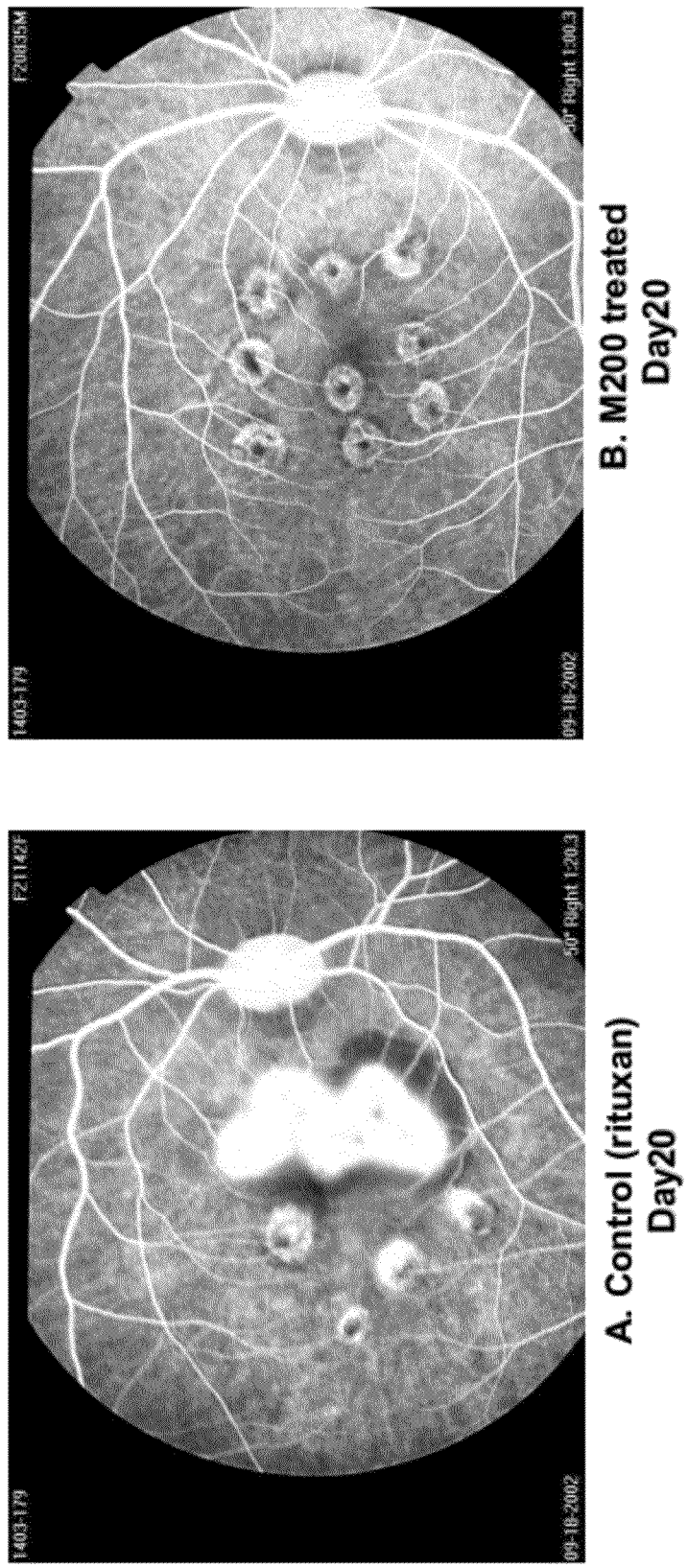
FIG. 19 depicts fluorescein angiography images of laser-induced lesions in primate eyes at day 20 of treatment with (A) control (rituxan) and (B) M200.
Figure 22:
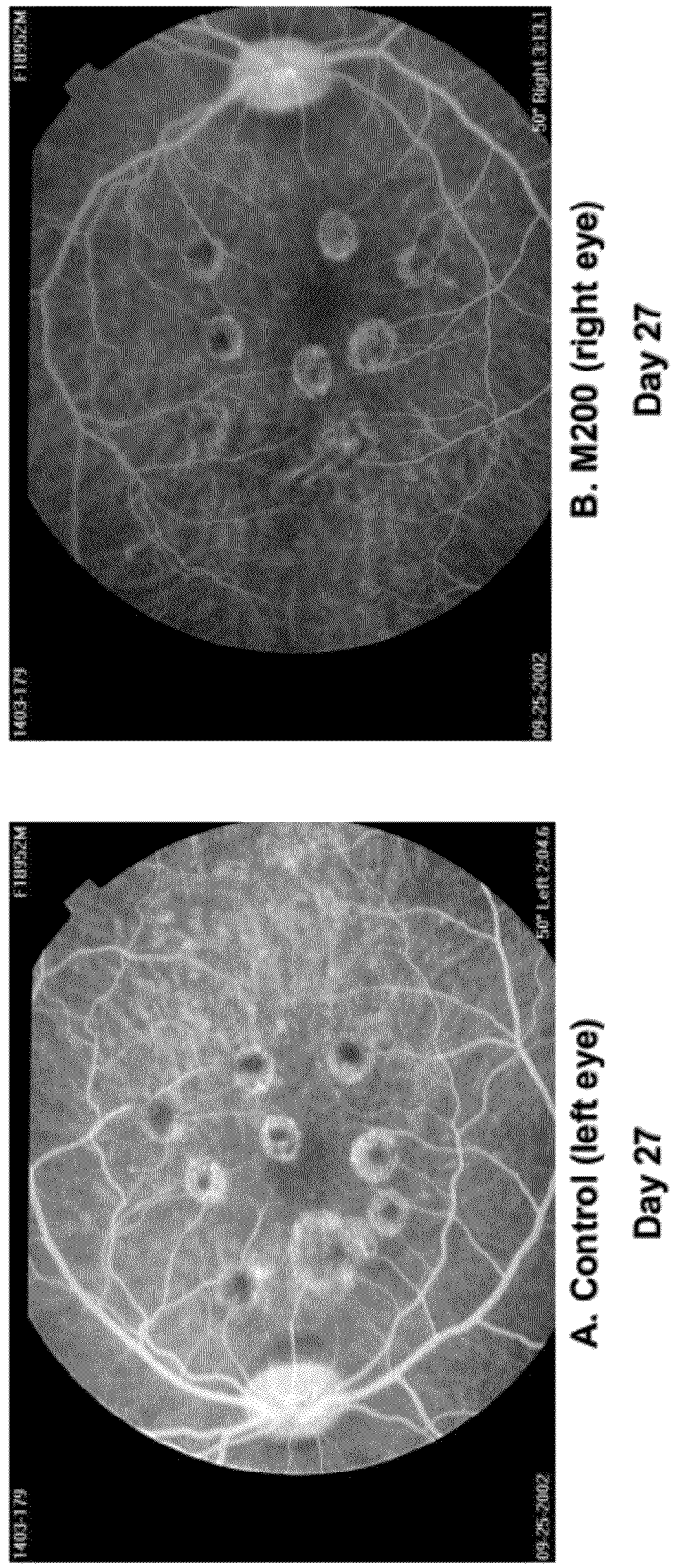
FIG. 22 depicts fluorescein angiography images of laser-induced lesions in the left and right eyes of an individual primate at day 27 of treatment with (A) control (left eye) and (B) M200 (right eye).
Figure 23:
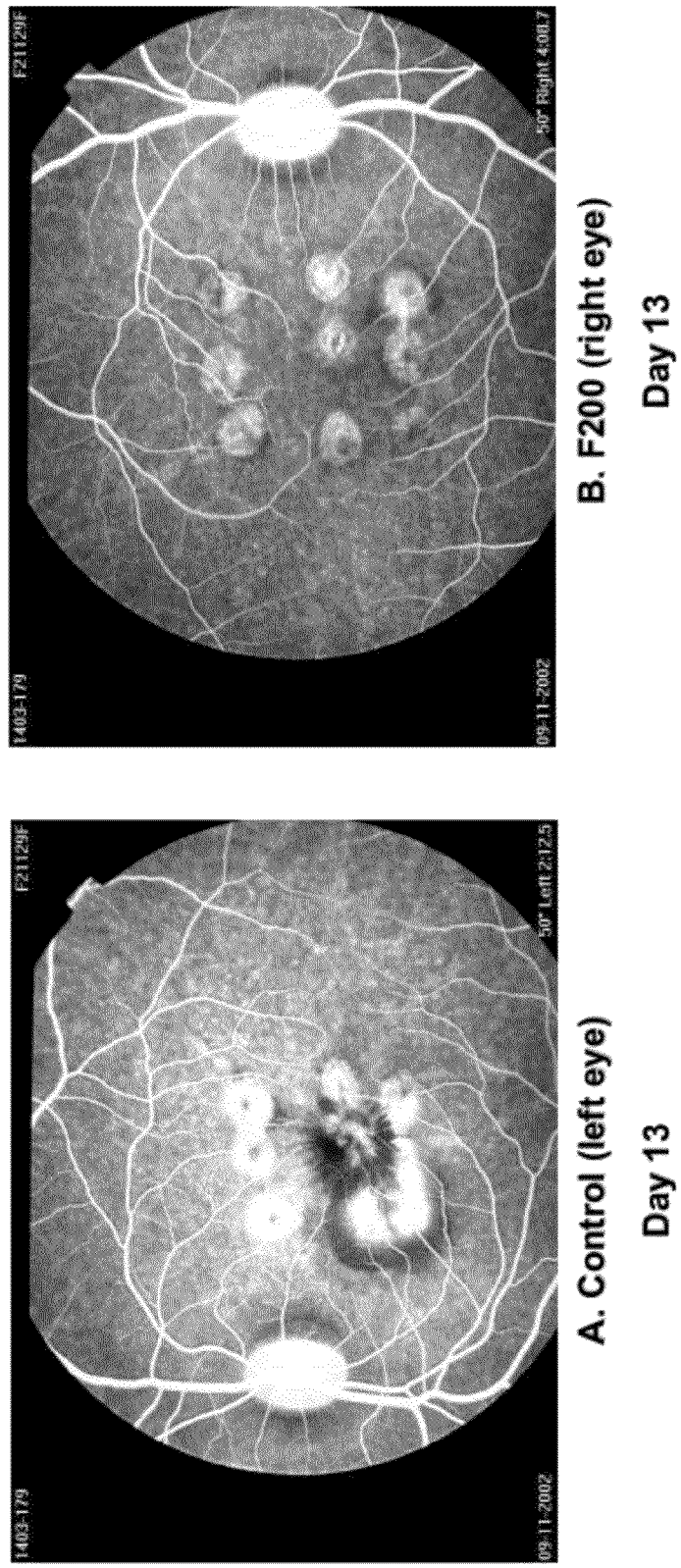
FIG. 23 depicts fluorescein angiography images of laser-induced lesions in the left and right eyes of an individual primate at day 13 of treatment with (A) control (left eye) and (B) F200 (right eye).
Figure 24:
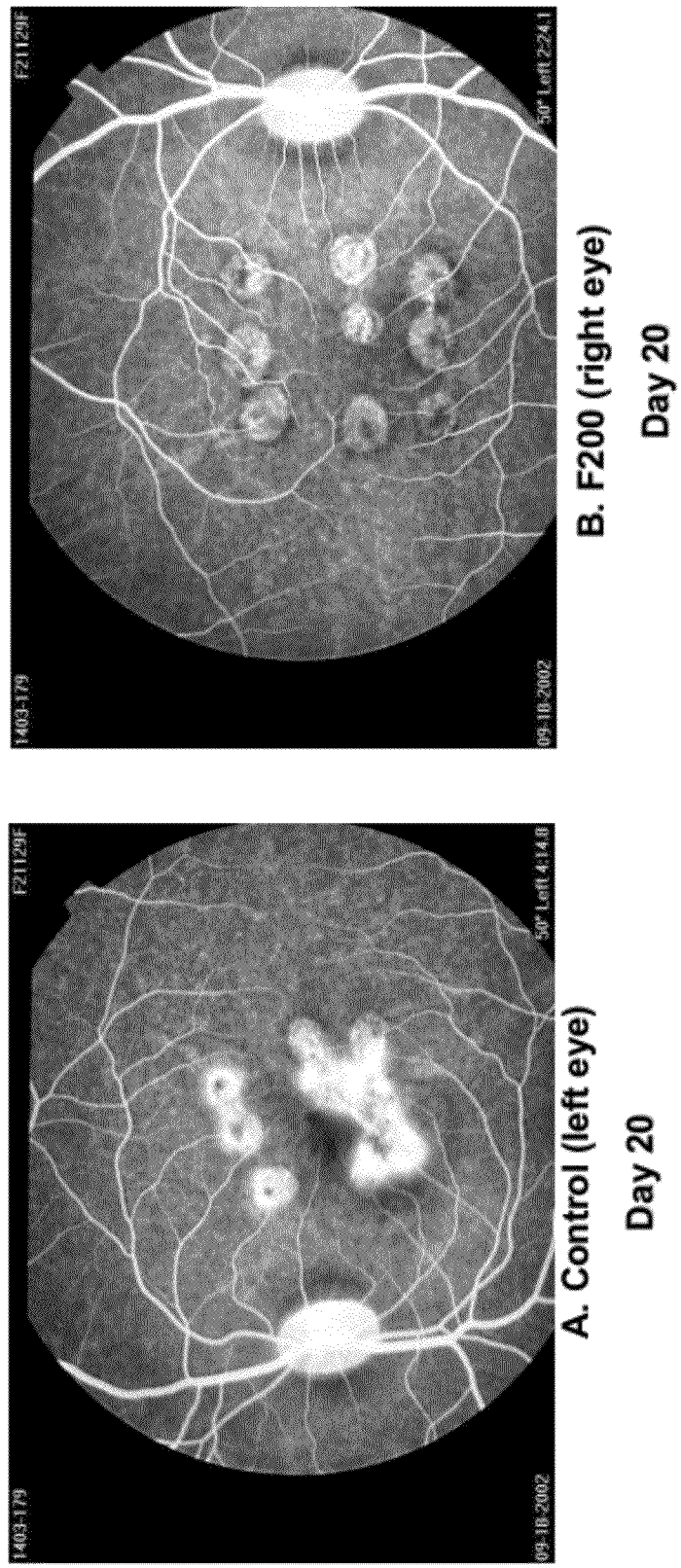
FIG. 24 depicts fluorescein angiography images of laser-induced lesions in the left and right eyes of an individual primate at day 20 of treatment with (A) control (left eye) and (B) F200 (right eye).
Figure 25:
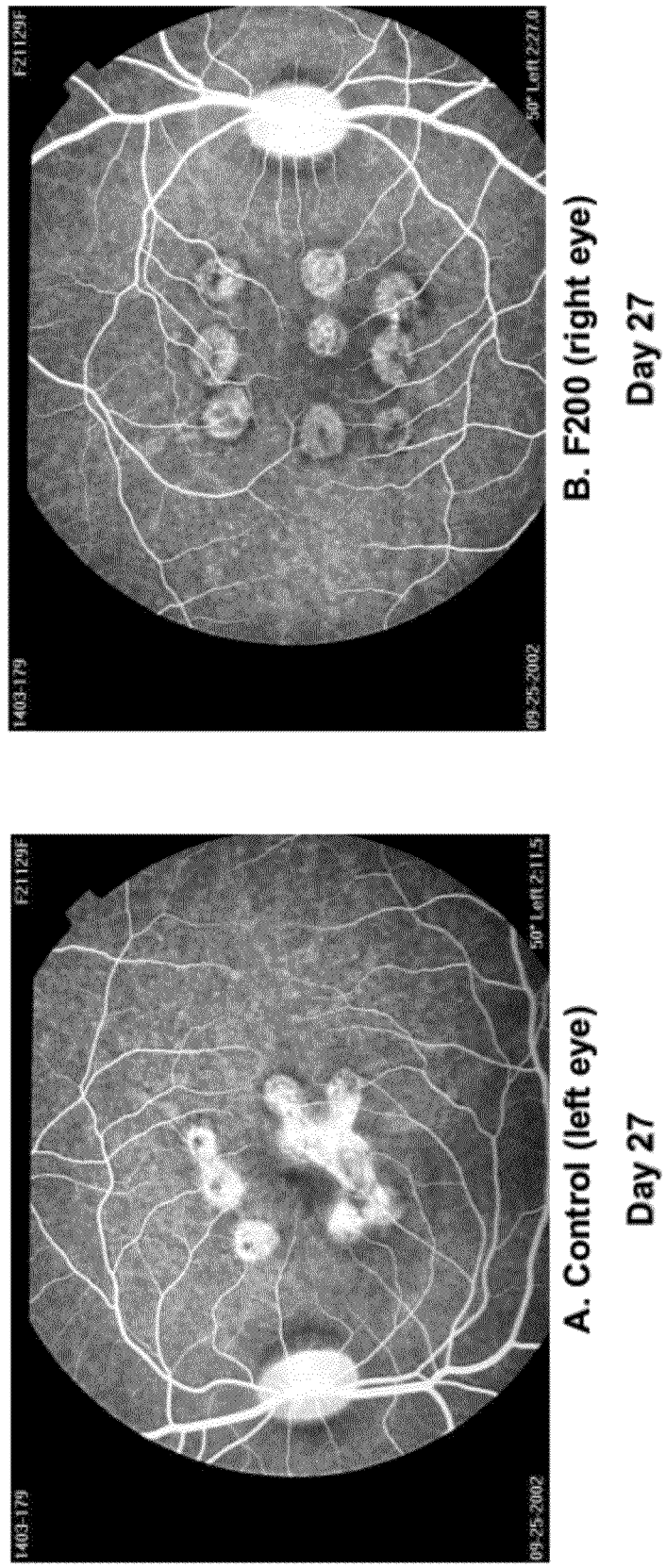
FIG. 25 depicts fluorescein angiography images of laser-induced lesions in the left and right eyes of an individual primate at day 27 of treatment with (A) control (left eye) and (B) F200 (right eye).

Analysis of fluorescein angiography images generated using these groups clearly indicates presence of CNV at day 13 and day 20. CNV persisted until day 28 in control groups (e.g. Groups 1, 4 (left eye) and 5 (left eye)). In contrast, the CNV was significantly reduced in M200 and F200-treated eyes (e.g. Groups 2, 3, 4 (right eye) and 5 (right eye)). As shown in FIG. 19, at day 20, an M200 treated eye was showed little indication of CNV relative to an eye treated only with control.

FIGS. 20-25 show the effect of M200 and F200 on CNV in an individual monkey's right eye versus the effect of control in the same monkey's left eye at days 13, 20 and 27. Significant reduction of CNV is observable in the individual's eyes treated with either M200 or F200 relative to the untreated eyes. The relative reduction in CNV appears to be greater in the individuals treated with F200. However it is believed that this apparent difference is due to leakage of the M200 through the bloodstream into the untreated left eye of the individuals. That is, M200 treatment in the individual's right eye also inhibits CNV in the left eye resulting in less apparent difference between the two eyes. In contrast, M200 does not leak over to the untreated eye resulting in a much greater difference in CNV inhibition between the individual's two eyes.

Example 7

Binding Affinity of M200, F200 and Humanized Variants

A. Kinetic Analyses by Surface Plasmon Resonance

Affinities between AAB1/B2Fc and IIA1, M200 or F200 were analyzed using BIAcore 3000 and 2000 (BIAcore, Sweden). IIA1, M200 or F200 was immobilized on the Pioneer F1 chip using standard amine coupling kit (BIAcore). Surface plasmon resonance was measured at a flow rate of 50 ul/min at 24° C. Injection of AAB1/B2Fc (association phase) occurs over 180 seconds. Dissociation was subsequently monitored over 3 hours. Kinetics of binding were calculated from data acquired at five different concentrations of analyte (320 nM, 160 nM, 80 nM, 40 nM, 20 nM), using the BIAevaluation program. Double-referencing was applied to eliminate responses from reference surface and buffer only control. $K_D$ was obtained by simultaneously fitting the association and dissociation phases of the sensorgram from the analyte concentration series. For M200 $K_D$ was determined to be 0.367±0.132 nM. For F200 $K_D$ was determined to be 0.332±0.065 nM.

B. HuM200 Affinity by Competition ELISA Assay

ELISA binding competition assays may be carried out to determine the binding affinity of the HuM200 relative to IIA1 and M200.

Wells of 96-well ELISA plates (Nunc-Immuno MaxiSorp plate, NalgeNunc, Naperville, Ill.) were coated with 100 μl of 1.0 μg/ml recombinant soluble recombinant human α5β1 integrin-Fc fusion protein in 0.2 M sodium carbonate-bicarbonate buffer (pH 9.4) overnight at 4° C. After washing with Wash Buffer (PBS containing 0.1% Tween 20), wells were blocked with 200 μl of Superblock Blocking Buffer (Pierce) for 30 min and then washed with Wash Buffer. A mixture of biotinylated murine IIA1 (0.1 μg/test) and competitor antibody (duplicates of serial 3-fold dilutions of competitor antibodies starting at 5 mg/ml) in ELISA Buffer (PBS containing 1% BSA and 0.1% Tween 20) was applied to ELISA plates in a final volume of 100 μl per well. ELISA plates were incubated for 1 hr at room temperature and the wells were washed with Wash Buffer. Then, 100 μl of 1/1,000-diluted HRP-conjugated streptavidin (Pierce, Rockford, Ill.) in ELISA Buffer was applied to each well. After incubating for 0.5 hr at room temperature and washing with Wash Buffer, 100 μl of TMB substrate was added to each well. Absorbance was read at 450 nm using a VERSAmax microplate reader (Molecular Devices, Menlo Park, Calif.). Final competitor concentration in the reaction was plotted versus absorbance at 450 nm.

HuM200 comprises the heavy and light chain amino acid sequences shown in FIG. 13 (SEQ ID NOS: 31 and 32). HuM200 (also referred to as HuM200-G4) includes a constant region from an IgG4. A second humanized version of M200, HuM200-g2 m3G includes the same variable domains as HuM200 but includes a constant region of IgG2.

Figure 26:
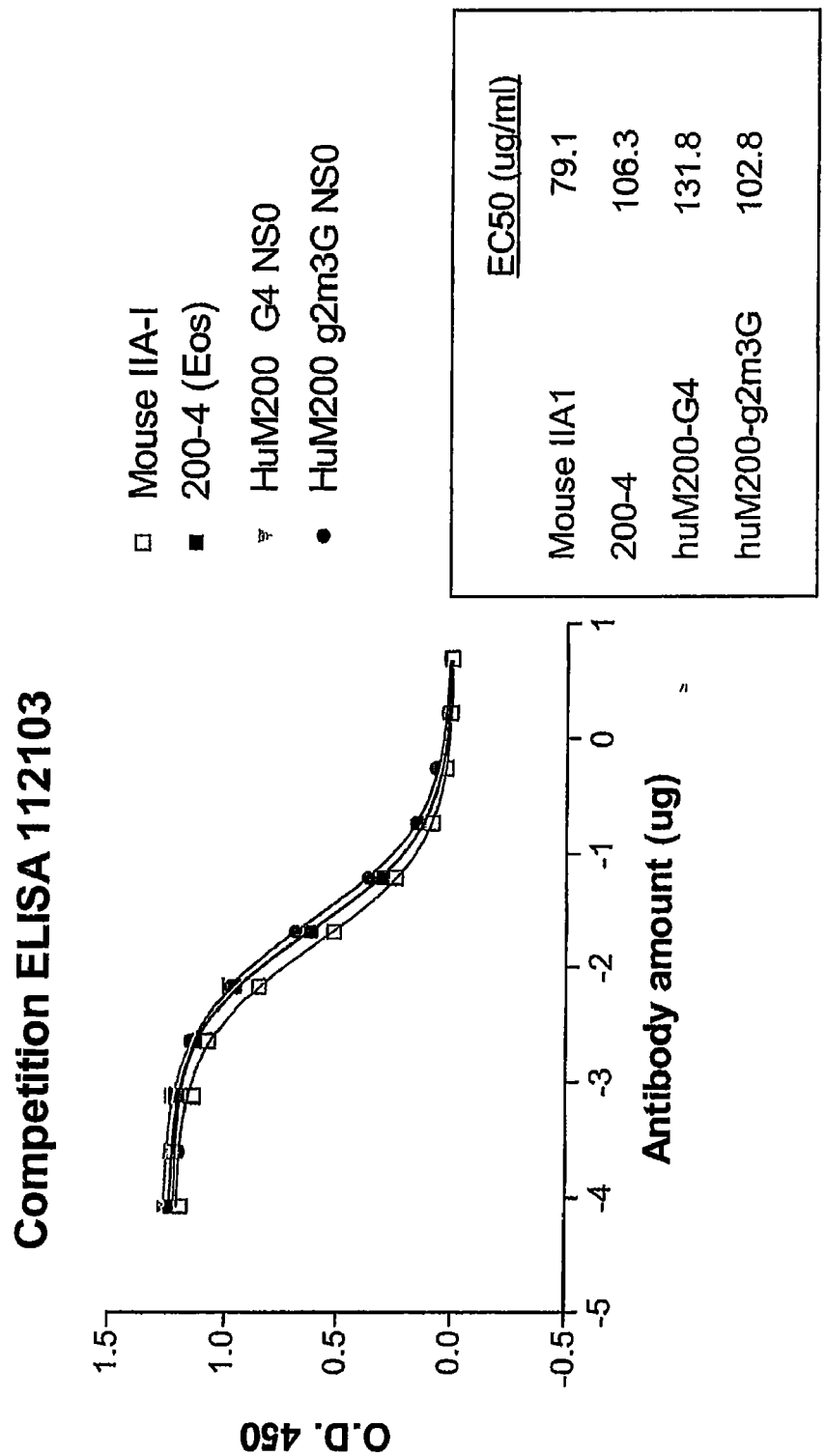
FIG. 26 depicts results of a competition ELISA binding assay comparing binding affinities of mouse antibody IIA1, chimeric antibody M200 (200-4 EOS), and two humanized versions of M200: huM200-G4 and huM200-g2 m3G.

As shown in FIG. 26, the two versions of the humanized M200 antibody, HuM200-G4 and HuM200-g2 m3G exhibit a binding affinity curve nearly identical to M200. In addition, HuM200-G4 and HuM200-g2 m3G have IC$_{50}$ values of 131.8 µg/ml and 102.8 µg/ml, respectively. These values are comparable to that observed for M200 (106.3 µg/ml), and slightly higher than IIA1 (79.1 µg/ml).

What is claimed is:

1. A method of treatment of an angiogenesis-associated ocular disease comprising applying one or more doses of a chimeric or humanized anti-α5β1 integrin antibody to an eye, wherein the anti-α5β1 integrin antibody comprises a heavy chain variable region selected from the group consisting of the amino acid sequences of SEQ ID NOs:25, 28, and 31, a light chain variable region consisting of the amino acid sequences of SEQ ID NOs:26 and 32, and a human IgG constant region.

2. The method of claim 1, wherein the source of the constant region is human IgG4 or IgG2.

3. The method of claim 1, wherein the ocular disease is selected from the group consisting of macular degeneration, diabetic retinopathy, or choroidal neovascularization.

4. The method of claim 1, wherein the anti-α5β1 integrin antibody comprises:

a) a heavy chain variable region consisting of the amino acid sequence of SEQ ID NO:25 and a light chain variable region consisting of the amino acid sequence of SEQ ID NO:26;

b) a heavy chain variable region consisting of the amino acid sequence of SEQ ID NO:28 and a light chain variable region consisting of the amino acid sequence of SEQ ID NO:26; or, c) a heavy chain variable region consisting of the amino acid sequence of SEQ ID NO:31 and a light chain variable region consisting of the amino acid sequence of SEQ ID NO:32.

5. The method of claim 1, wherein applying comprises intravitreal injection.

6. The method of claim 1, wherein applying comprises intravenous injection.

* * * * *

SEQUENCE LISTING

```
<160> NUMBER OF SEQ ID NOS: 47

<210> SEQ ID NO 1
<211> LENGTH: 124
<212> TYPE: PRT
<213> ORGANISM: mus musculus

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Ser Val Thr Val Ser Ser
        115                 120

<210> SEQ ID NO 2
<211> LENGTH: 124
<212> TYPE: PRT
<213> ORGANISM: Artificial Sequence Sequence
<220> FEATURE:
<223> OTHER INFORMATION: humanized antibody

<400> SEQUENCE: 2

Gln Val Gln Leu Val Glu Ser Gly Pro Gly Leu Val Gln Pro Gly Gly
1               5                   10                  15

Ser Leu Arg Ile Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Ser Lys Asp Asn Ser Lys Ser Thr Val Tyr Leu
65                  70                  75                  80

Gln Met Asn Ser Leu Arg Ala Glu Asp Thr Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
        115                 120

<210> SEQ ID NO 3
<211> LENGTH: 124
<212> TYPE: PRT
<213> ORGANISM: Artificial Sequence Sequence
<220> FEATURE:
<223> OTHER INFORMATION: humanized antibody
```

<400> SEQUENCE: 3

Glu Val Gln Leu Val Glu Ser Gly Gly Gly Leu Val Gln Pro Gly Gly
1               5                   10                  15

Ser Leu Arg Ile Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
            115                 120

<210> SEQ ID NO 4
<211> LENGTH: 124
<212> TYPE: PRT
<213> ORGANISM: Artificial Sequence
<220> FEATURE:
<223> OTHER INFORMATION: humanized antibody

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Val
        35                  40                  45

Ser Val Ile Trp Ser Asp Gly Ser Ser Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
            115                 120

<210> SEQ ID NO 5
<211> LENGTH: 124
<212> TYPE: PRT
<213> ORGANISM: Artificial Sequence
<220> FEATURE:
<223> OTHER INFORMATION: humanized antibody

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

```
Val Val Ile Trp Ser Asp Gly Ser Ser Thr Tyr Asn Ser Ala Leu Lys
        50                  55                  60

Ser Arg Met Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
            115                 120

<210> SEQ ID NO 6
<211> LENGTH: 124
<212> TYPE: PRT
<213> ORGANISM: Artificial Sequence
<220> FEATURE:
<223> OTHER INFORMATION: humanized antibody

<400> SEQUENCE: 6

Gln Val Gln Leu Val Glu Ser Gly Gly Gly Leu Val Gln Pro Gly Gly
1               5                   10                  15

Ser Leu Arg Ile Ser Cys Ala Ile Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Ser Thr Tyr Asn Ser Ala Leu Lys
        50                  55                  60

Ser Arg Met Thr Ile Ser Lys Asp Asn Ser Lys Ser Thr Val Tyr Leu
65                  70                  75                  80

Gln Met Asn Ser Leu Arg Ala Glu Asp Thr Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Leu Val Thr Val Ser Ser
            115                 120

<210> SEQ ID NO 7
<211> LENGTH: 109
<212> TYPE: PRT
<213> ORGANISM: mus musculus

<400> SEQUENCE: 7

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Asn
            20                  25                  30

Tyr Leu His Trp Tyr Gln Gln Lys Pro Gly Ser Ala Pro Asn Leu Trp
        35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr Leu Arg Ser Pro
                85                  90                  95

Pro Thr Phe Gly Gly Gly Thr Lys Leu Glu Ile Lys Arg
            100                 105

<210> SEQ ID NO 8
```

<211> LENGTH: 109
<212> TYPE: PRT
<213> ORGANISM: Artificial Sequence
<220> FEATURE:
<223> OTHER INFORMATION: humanized antibody

<400> SEQUENCE: 8

Asp Ile Gln Leu Thr Gln Ser Pro Ser Ser Met Ser Ala Ser Leu Gly
1               5                   10                  15

Asp Arg Val Thr Met Thr Cys Thr Ala Ser Ser Val Ser Ser Asn
            20                  25                  30

Tyr Leu His Trp Tyr Gln Gln Lys Pro Gly Lys Ala Pro Asn Leu Trp
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Met Gln
65                  70                  75                  80

Pro Glu Asp Phe Ala Thr Tyr Tyr Cys His Gln Tyr Leu Arg Ser Pro
                85                  90                  95

Pro Thr Phe Gly Gln Gly Thr Lys Leu Glu Ile Lys Arg
            100                 105

<210> SEQ ID NO 9
<211> LENGTH: 109
<212> TYPE: PRT
<213> ORGANISM: Artificial Sequence
<220> FEATURE:
<223> OTHER INFORMATION: humanized antibody

<400> SEQUENCE: 9

Asp Ile Gln Leu Thr Gln Ser Pro Ser Ser Leu Ser Ala Ser Val Gly
1               5                   10                  15

Asp Arg Val Thr Met Thr Cys Thr Ala Ser Ser Val Ser Ser Asn
            20                  25                  30

Tyr Leu His Trp Tyr Gln Gln Lys Pro Gly Lys Ala Pro Lys Leu Trp
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Met Gln
65                  70                  75                  80

Pro Glu Asp Phe Ala Thr Tyr Tyr Cys His Gln Tyr Leu Arg Ser Pro
                85                  90                  95

Pro Thr Phe Gly Gln Gly Thr Lys Leu Glu Ile Lys Arg
            100                 105

<210> SEQ ID NO 10
<211> LENGTH: 109
<212> TYPE: PRT
<213> ORGANISM: Artificial Sequence
<220> FEATURE:
<223> OTHER INFORMATION: humanized antibody

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Val Ser Ser Asn
            20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser

```
                50                  55                  60
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys His Gln Tyr Leu Arg Ser Pro
                 85                  90                  95

Pro Thr Phe Gly Gln Gly Thr Lys Val Glu Ile Lys Arg
            100                 105

<210> SEQ ID NO 11
<211> LENGTH: 109
<212> TYPE: PRT
<213> ORGANISM: Artificial Sequence
<220> FEATURE:
<223> OTHER INFORMATION: humanized antibody

<400> SEQUENCE: 11

Asp Ile Gln Leu Thr Gln Ser Pro Ser Ser Leu Ser Ala Ser Val Gly
 1               5                  10                  15

Asp Arg Val Thr Ile Thr Cys Thr Ala Ser Ser Ser Val Ser Ser Asn
                20                  25                  30

Tyr Leu His Trp Tyr Gln Gln Lys Pro Gly Lys Ala Pro Lys Leu Trp
            35                  40                  45

Ile Tyr Ser Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Tyr Leu Arg Ser Pro
                 85                  90                  95

Pro Thr Phe Gly Gln Gly Thr Lys Val Glu Ile Lys Arg
            100                 105

<210> SEQ ID NO 12
<211> LENGTH: 109
<212> TYPE: PRT
<213> ORGANISM: Artificial Sequence
<220> FEATURE:
<223> OTHER INFORMATION: humanized antibody

<400> SEQUENCE: 12

Asp Ile Gln Leu Thr Gln Ser Pro Ser Ser Leu Ser Ala Ser Val Gly
 1               5                  10                  15

Asp Arg Val Thr Met Thr Cys Thr Ala Ser Ser Ser Val Ser Ser Asn
                20                  25                  30

Tyr Leu His Trp Tyr Gln Gln Lys Pro Gly Lys Ala Pro Lys Leu Trp
            35                  40                  45

Ile Tyr Ser Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Tyr Leu Arg Ser Pro
                 85                  90                  95

Pro Thr Phe Gly Gln Gly Thr Lys Val Glu Ile Lys Arg
            100                 105

<210> SEQ ID NO 13
<211> LENGTH: 429
<212> TYPE: DNA
<213> ORGANISM: mus musculus

<400> SEQUENCE: 13
```

```
atggctgtcc tggggctgct tctctgcctg gtgactttcc caagctgtgt cctgtcccag      60
gtgcagctga aggagtcagg acctggcctg gtggcgccct cacagagcct gtccatcaca     120
tgcaccatct cagggttctc attaaccgac tatggtgttc actgggttcg ccagcctcca     180
ggaaagggtc tggagtggct ggtagtgatt tggagtgatg aagctcaac  ctataattca     240 gctctcaaat ccagaatgac catcaggaag acaactcca  agagccaagt tttcttaata     300
atgaacagtc tccaaactga tgactcagcc atgtactact gtgccagaca tggaacttac     360
tacggtatga ctacgacggg ggatgctttg gactactggg gtcaaggaac ctcagtcacc     420
gtctcctca                                                             429

<210> SEQ ID NO 14
<211> LENGTH: 390
<212> TYPE: DNA
<213> ORGANISM: mus musculus

<400> SEQUENCE: 14 atggatttc  aggtgcagat tttcagcttc ctgctaatca gtgcctcagt cataatgtcc      60
agaggacaaa ttgttctcac ccagtctcca gcaatcatgt ctgcatctct aggggaacgg     120
gtcaccatga cctgcactgc cagttcaagt gtaagttcca attacttgca ctggtaccag     180
cagaagccag atccgcccc  caatctctgg atttatagca catccaacct ggcttctgga     240
gtcccagctc gtttcagtgg cagtgggtct gggacctctt actctctcac aatcagcagc     300
atggaggctg aagatgctgc cacttattac tgccaccagt atcttcgttc cccaccgacg     360
ttcggtggag gcaccaagct ggaaatcaaa                                      390

<210> SEQ ID NO 15
<211> LENGTH: 429
<212> TYPE: DNA
<213> ORGANISM: Artificial Sequence
<220> FEATURE:
<223> OTHER INFORMATION: chimeric antibody

<400> SEQUENCE: 15
atggctgtcc tggggctgct tctctgcctg gtgactttcc caagctgtgt cctgtcccag      60
gtgcagctga aggagtcagg acctggcctg gtggcgccct cacagagcct gtccatcaca     120
tgcaccatct cagggttctc attaaccgac tatggtgttc actgggttcg ccagcctcca     180
ggaaagggtc tggagtggct ggtagtgatt tggagtgatg aagctcaac  ctataattca     240 gctctcaaat ccagaatgac catcaggaag acaactcca  agagccaagt tttcttaata     300
atgaacagtc tccaaactga tgactcagcc atgtactact gtgccagaca tggaacttac     360
tacggtatga ctacgacggg ggatgctttg gactactggg gtcaaggaac ctcagtcacc     420
gtctcgagc                                                             429

<210> SEQ ID NO 16
<211> LENGTH: 143
<212> TYPE: PRT
<213> ORGANISM: Artificial Sequence
<220> FEATURE:
<223> OTHER INFORMATION: chimeric antibody

<400> SEQUENCE: 16

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30
```

Pro Ser Gln Ser Leu Ser Ile Thr Cys Thr Ile Ser Gly Phe Ser Leu
                35                  40                  45

Thr Asp Tyr Gly Val His Trp Val Arg Gln Pro Pro Gly Lys Gly Leu
 50                  55                  60

Glu Trp Leu Val Val Ile Trp Ser Asp Gly Ser Ser Thr Tyr Asn Ser
65                  70                  75                  80

Ala Leu Lys Ser Arg Met Thr Ile Arg Lys Asp Asn Ser Lys Ser Gln
                85                  90                  95

Val Phe Leu Ile Met Asn Ser Leu Gln Thr Asp Asp Ser Ala Met Tyr
            100                 105                 110

Tyr Cys Ala Arg His Gly Thr Tyr Tyr Gly Met Thr Thr Thr Gly Asp
        115                 120                 125

Ala Leu Asp Tyr Trp Gly Gln Gly Thr Ser Val Thr Val Ser Ser
    130                 135                 140

<210> SEQ ID NO 17
<211> LENGTH: 390
<212> TYPE: DNA
<213> ORGANISM: Artificial Sequence
<220> FEATURE:
<223> OTHER INFORMATION: chimeric antibody

<400> SEQUENCE: 17 atggatttc aggtgcagat tttcagcttc ctgctaatca gtgcctcagt cataatgtcc      60
agaggacaaa ttgttctcac ccagtctcca gcaatcatgt ctgcatctct aggggaacgg    120
gtcaccatga cctgcactgc cagttcaagt gtaagttcca attacttgca ctggtaccag    180
cagaagccag gatccgcccc caatctctgg atttatagca catccaacct ggcttctgga    240
gtcccagctc gtttcagtgg cagtgggtct gggacctctt actctctcac aatcagcagc    300
atggaggctg aagatgctgc cacttattac tgccaccagt atcttcgttc cccaccgacg    360
ttcggtggag gcaccaagct cgagatcaaa                                     390

<210> SEQ ID NO 18
<211> LENGTH: 130
<212> TYPE: PRT
<213> ORGANISM: Artificial Sequence
<220> FEATURE:
<223> OTHER INFORMATION: chimeric antibody

<400> SEQUENCE: 18

Met Asp Phe Gln Val Gln Ile Phe Ser Phe Leu Leu Ile Ser Ala Ser
1                5                  10                  15

Val Ile Met Ser Arg Gly Gln Ile Val Leu Thr Gln Ser Pro Ala Ile
                20                  25                  30

Met Ser Ala Ser Leu Gly Glu Arg Val Thr Met Thr Cys Thr Ala Ser
            35                  40                  45

Ser Ser Val Ser Ser Asn Tyr Leu His Trp Tyr Gln Gln Lys Pro Gly
        50                  55                  60

Ser Ala Pro Asn Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr Leu Arg Ser Pro Pro Thr Phe Gly Gly Gly Thr Lys Leu Glu
        115                 120                 125

Ile Lys
    130

<210> SEQ ID NO 19
<211> LENGTH: 459
<212> TYPE: DNA
<213> ORGANISM: Artificial Sequence
<220> FEATURE:
<223> OTHER INFORMATION: chimeric antibody

<400> SEQUENCE: 19

```
tctagaccac catggctgtc ctggggctgc ttctctgcct ggtgactttc ccaagctgtg      60
tcctgtccca ggtgcagctg aaggagtcag gacctggcct ggtggcgccc tcacagagcc     120
tgtccatcac atgcaccatc tcaggttct cattaaccga ctatggtgtt cactgggttc     180
gccagcctcc aggaaagggt ctggagtggc tggtagtgat tggagtgat ggaagctcaa      240
cctataattc agctctcaaa tccagaatga ccatcaggaa ggacaactcc aagagccaag     300
ttttcttaat aatgaacagt ctccaaactg atgactcagc catgtactac tgtgccagac     360
atggaactta ctacggaatg actacgacgg gggatgcttt ggactactgg ggtcaaggaa     420
cctcagtcac cgtctcctca ggtaagaatg gcctctaga                            459
```

<210> SEQ ID NO 20
<211> LENGTH: 143
<212> TYPE: PRT
<213> ORGANISM: Artificial Sequence
<220> FEATURE:
<223> OTHER INFORMATION: chimeric antibody

<400> SEQUENCE: 20

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Ile Ser Gly Phe Ser Leu
        35                  40                  45

Thr Asp Tyr Gly Val His Trp Val Arg Gln Pro Pro Gly Lys Gly Leu
    50                  55                  60

Glu Trp Leu Val Val Ile Trp Ser Asp Gly Ser Ser Thr Tyr Asn Ser
65                  70                  75                  80

Ala Leu Lys Ser Arg Met Thr Ile Arg Lys Asp Asn Ser Lys Ser Gln
                85                  90                  95

Val Phe Leu Ile Met Asn Ser Leu Gln Thr Asp Asp Ser Ala Met Tyr
            100                 105                 110

Tyr Cys Ala Arg His Gly Thr Tyr Tyr Gly Met Thr Thr Thr Gly Asp
        115                 120                 125

Ala Leu Asp Tyr Trp Gly Gln Gly Thr Ser Val Thr Val Ser Ser
    130                 135                 140

<210> SEQ ID NO 21
<211> LENGTH: 425
<212> TYPE: DNA
<213> ORGANISM: Artificial Sequence
<220> FEATURE:
<223> OTHER INFORMATION: chimeric antibody

<400> SEQUENCE: 21

```
acgcgtccac catggatttt caggtgcaga ttttcagctt cctgctaatc agtgcctcag      60
tcataatgtc cagaggacaa attgttctca cccagtctcc agcaatcatg tctgcatctc     120
```

```
tagggggaacg ggtcaccatg acctgcactg ccagttcaag tgtcagttcc aattacttgc    180
actggtacca gcagaagcca ggatccgccc ccaatctctg gatttatagc acatccaacc    240
tggcttctgg agtcccagct cgtttcagtg gcagtgggtc tgggacctct tactctctca    300
caatcagcag catggaggct gaagatgctg ccacttatta ctgccaccag tatcttcgtt    360
ccccaccgac gttcggtgga ggcaccaagc tggaaatcaa acgtaagtag aatccaaagt    420
ctaga                                                                425
```

```
<210> SEQ ID NO 22
<211> LENGTH: 130
<212> TYPE: PRT
<213> ORGANISM: Artificial Sequence
<220> FEATURE:
<223> OTHER INFORMATION: chimeric antibody

<400> SEQUENCE: 22

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Asn Tyr Leu His Trp Tyr Gln Gln Lys Pro Gly
    50                  55                  60

Ser Ala Pro Asn Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr Leu Arg Ser Pro Pro Thr Phe Gly Gly Gly Thr Lys Leu Glu
        115                 120                 125

Ile Lys
    130
```

```
<210> SEQ ID NO 23
<211> LENGTH: 1353
<212> TYPE: DNA
<213> ORGANISM: Artificial Sequence
<220> FEATURE:
<223> OTHER INFORMATION: chimeric antibody

<400> SEQUENCE: 23
caggtgcagc tgaaggagtc aggacctggc ctggtggcgc cctcacagag cctgtccatc    60
acatgcacca tctcagggtt ctcattaacc gactatggtt tcactgggt tcgccagcct    120 ccaggaaagg gtctggagtg gctggtagtg atttggagtg atggaagctc aacctataat    180
tcagctctca atccagaat gaccatcagg aaggacaact ccaagagcca gttttctta    240 ataatgaaca gtctccaaac tgatgactca gccatgtact actgtgccag acatggaact    300
tactacggaa tgactacgac gggggatgct ttggactact ggggtcaagg aacctcagtc    360
accgtctcct cagcttccac caagggccca tccgtcttcc cctggcgcc ctgctccagg    420 agcacctccg agagcacagc cgccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ccgtgccctc cagcagcttg    600
ggcacgaaga cctacacctg caacgtagat cacaagccca gcaacaccaa ggtggacaag    660
```

```
agagttgagt ccaaatatgg tcccccatgc ccatcatgcc cagcacctga gttcctgggg      720
ggaccatcag tcttcctgtt ccccccaaaa cccaaggaca ctctcatgat ctcccggacc      780
cctgaggtca cgtgcgtggt ggtggacgtg agccaggaag accccgaggt ccagttcaac      840
tggtacgtgg atggcgtgga ggtgcataat gccaagacaa agccgcggga ggagcagttc      900
aacagcacgt accgtgtggt cagcgtcctc accgtcctgc accaggactg gctgaacggc      960
aaggagtaca agtgcaaggt ctccaacaaa ggcctcccgt cctccatcga gaaaaccatc     1020
tccaaagcca agggcagccc cgagagccag gtgtacaccc tgcccccatc ccaggag       1080 gagatgacca agaaccaggt cagcctgacc tgcctggtca aaggcttcta ccccagcgac     1140
atcgccgtgg agtgggagag caatgggcag ccggagaaca actacaagac cacgcctccc     1200
gtgctggact ccgacggctc cttcttcctc tacagcaggc taaccgtgga caagagcagg     1260
tggcaggagg ggaatgtctt ctcatgctcc gtgatgcatg aggctctgca caaccactac     1320
acacagaaga gcctctccct gtctctgggt aaa                                  1353
```

<210> SEQ ID NO 24
<211> LENGTH: 645
<212> TYPE: DNA
<213> ORGANISM: Artificial Sequence
<220> FEATURE:
<223> OTHER INFORMATION: chimeric antibody

<400> SEQUENCE: 24

```
caaattgttc tcacccagtc tccagcaatc atgtctgcat ctctagggga cgggtcacc       60 atgacctgca ctgccagttc aagtgtaagt tccaattact tgcactggta ccagcagaag     120
ccaggatccg cccccaatct ctggatttat agcacatcca acctggcttc tggagtccca     180
gctcgtttca gtggcagtgg gtctgggacc tcttactctc tcacaatcag cagcatggag     240
gctgaagatg ctgccactta ttactgccac cagtatcttc gttccccacc gacgttcggt     300
ggaggcacca agctggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgt                    645
```

<210> SEQ ID NO 25
<211> LENGTH: 451
<212> TYPE: PRT
<213> ORGANISM: Artificial Sequence
<220> FEATURE:
<223> OTHER INFORMATION: chimeric antibody

<400> SEQUENCE: 25

```
Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
```

```
                65                  70                  75                  80
Ile Met Asn Ser Leu Gln Thr Asp Asp Ser Ala Met Tyr Tyr Cys Ala
                    85                  90                  95

Arg His Gly Thr Tyr Tyr Gly Met Thr Thr Thr Gly Asp Ala Leu Asp
                100                 105                 110

Tyr Trp Gly Gln Gly Thr Ser Val Thr Val Ser Ser Ala Ser Thr Lys
            115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
            435                 440                 445

Leu Gly Lys
    450

<210> SEQ ID NO 26
<211> LENGTH: 215
<212> TYPE: PRT
<213> ORGANISM: Artificial Sequence
<220> FEATURE:
```

<223> OTHER INFORMATION: chimeric antibody

<400> SEQUENCE: 26

```
Gln Ile Val Leu Thr Gln Ser Pro Ala Ile Met Ser Ala Ser Leu Gly
1               5                   10                  15
Glu Arg Val Thr Met Thr Cys Thr Ala Ser Ser Val Ser Ser Asn
            20                  25                  30
Tyr Leu His Trp Tyr Gln Gln Lys Pro Gly Ser Ala Pro Asn Leu Trp
            35                  40                  45
Ile Tyr Ser Thr Ser Asn Leu Ala Ser Gly Val Pro Ala Arg Phe Ser
        50                  55                  60
Gly Ser Gly Ser Gly Thr Ser Tyr Ser Leu Thr Ile Ser Ser Met Glu
65                  70                  75                  80
Ala Glu Asp Ala Ala Thr Tyr Tyr Cys His Gln Tyr Leu Arg Ser Pro
                85                  90                  95
Pro Thr Phe Gly Gly Gly Thr Lys Leu Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 27
<211> LENGTH: 696
<212> TYPE: DNA
<213> ORGANISM: Artificial Sequence
<220> FEATURE:
<223> OTHER INFORMATION: chimeric antibody

<400> SEQUENCE: 27

```
caggtgcagc tgaaggagtc aggacctggc ctggtggcgc cctcacagag cctgtccatc        60
acatgcacca tctcagggtt ctcattaacc gactatggtg ttcactgggt tcgccagcct       120
ccaggaaagg gtctggagtg gctggtagtg atttggagtg atggaagctc aacctataat       180
tcagctctca atccagaat gaccatcagg aaggacaact ccaagagcca agtttttctta       240
ataatgaaca gtctccaaac tgatgactca gccatgtact actgtgccag acatggaact       300
tactacggaa tgactacgac gggggatgct ttggactact ggggtcaagg aacctcagtc       360
accgtctcct cagcttccac caagggccca tccgtcttcc cctggcgcc ctgctccagg        420
agcacctccg agagcacagc cgccctgggc tgcctggtca aggactactt ccccgaaccg       480
gtgacggtgt cgtggaactc aggcgccctg accagcggcg tgcacacctt cccggctgtc       540
ctacagtcct caggactcta ctccctcagc agcgtggtga ccgtgccctc agcagcttg         600
ggcacgaaga cctacacctg caacgtagat cacaagccca gcaacaccaa ggtggacaag       660
agagttgagt ccaaatatgg tcccccatgc ccatca                                 696
```

```
<210> SEQ ID NO 28
<211> LENGTH: 232
<212> TYPE: PRT
<213> ORGANISM: Artificial Sequence
<220> FEATURE:
<223> OTHER INFORMATION: chimeric antibody

<400> SEQUENCE: 28

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Gly Asp Ala Leu Asp
            100                 105                 110

Tyr Trp Gly Gln Gly Thr Ser Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser
225                 230

<210> SEQ ID NO 29
<211> LENGTH: 1353
<212> TYPE: DNA
<213> ORGANISM: Artificial Sequence
<220> FEATURE:
<223> OTHER INFORMATION: chimeric antibody

<400> SEQUENCE: 29
gaggtgcagc tggtggagtc aggaggaggc ctggtgcagc cggaggaag  cctgagactg      60 tcatgcgccg cctcaggggtt ctcattaacc gactatggtg ttcactgggt tcgccaggcc    120
ccaggaaagg gtctggagtg gctggtggtg atttggagtg atggaagctc aacctataat    180
tcagctctca atccagaat gaccatctca aggacaacg ccaagaacac cgtgtactta      240
cagatgaaca gtctcagagc tgaggacacc gccgtgtact actgtgccag acatggaact    300
tactacggaa tgactacgac gggggatgct ttggactact ggggtcaagg aaccctggtc    360
accgtctcct cagcttccac caagggccca tccgtcttcc cctggcgcc ctgctccagg     420 agcacctccg agagcacagc cgccctgggc tgcctggtca aggactactt ccccgaaccg    480
```

```
gtgacggtgt cgtggaactc aggcgccctg accagcggcg tgcacacctt cccggctgtc    540
ctacagtcct caggactcta ctccctcagc agcgtggtga ccgtgccctc agcagcttg     600 ggcacgaaga cctacacctg caacgtagat cacaagccca gcaacaccaa ggtggacaag    660
agagttgagt ccaaatatgg tcccccatgc ccatcatgcc cagcacctga gttcctgggg    720
ggaccatcag tcttcctgtt cccccccaaaa cccaaggaca ctctcatgat ctcccggacc   780
cctgaggtca cgtgcgtggt ggtggacgtg agccaggaag accccgaggt ccagttcaac    840
tggtacgtgg atggcgtgga ggtgcataat gccaagacaa agccgcggga ggagcagttc    900
aacagcacgt accgtgtggt cagcgtcctc accgtcctgc accaggactg gctgaacggc    960
aaggagtaca agtgcaaggt ctccaacaaa ggcctcccgt cctccatcga aaaaccatc    1020 tccaaagcca agggcagcc ccgagagcca caggtgtaca ccctgccccc atcccaggag   1080
gagatgacca gaaccaggt cagcctgacc tgcctggtca aaggcttcta ccccagcgac   1140
atcgccgtgg agtgggagag caatgggcag ccggagaaca actacaagac cacgcctccc   1200
gtgctggact ccgacggctc cttcttcctc tacagcaggc taaccgtgga caagagcagg   1260
tggcaggagg ggaatgtctt ctcatgctcc gtgatgcatg aggctctgca caaccactac   1320
acacagaaga gcctctccct gtctctgggt aaa                                 1353
```

<210> SEQ ID NO 30
<211> LENGTH: 645
<212> TYPE: DNA
<213> ORGANISM: Artificial Sequence
<220> FEATURE:
<223> OTHER INFORMATION: chimeric antibody

<400> SEQUENCE: 30

```
gaaattgttc tcacccagtc tccagcaacc ctctctctct ctccggggga cgggctacc     60 ctctcctgca ctgccagttc aagtgtcagt tccaattact tgcactggta ccagcagaag    120
ccaggacagg ccccccgtct cctcatttat agcacatcca acctggcttc tggagtccca    180
gctcgtttca gtggcagtgg gtctgggacc tcttacaccc tcacaatcag cagcctcgag    240
ccagaagatt tcgccgtcta ttactgccac cagtatcttc gttccccacc gacgttcggt    300
ggaggcacca aggtcgaaat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacagggag agtgt                     645
```

<210> SEQ ID NO 31
<211> LENGTH: 451
<212> TYPE: PRT
<213> ORGANISM: Artificial Sequence
<220> FEATURE:
<223> OTHER INFORMATION: chimeric antibody

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
```

-continued

```
                35                  40                  45
Val Val Ile Trp Ser Asp Gly Ser Ser Thr Tyr Asn Ser Ala Leu Lys
 50                  55                  60

Ser Arg Met Thr Ile Ser Lys Asp Asn Ala Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg His Gly Thr Tyr Tyr Gly Met Thr Thr Gly Asp Ala Leu Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450
```

-continued

```
<210> SEQ ID NO 32
<211> LENGTH: 215
<212> TYPE: PRT
<213> ORGANISM: Artificial Sequence
<220> FEATURE:
<223> OTHER INFORMATION: chimeric antibody

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Val Ser Ser Asn
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Thr Leu Thr Ile Ser Ser Leu Glu
65                  70                  75                  80

Pro Glu Asp Phe Ala Val Tyr Tyr Cys His Gln Tyr Leu Arg Ser Pro
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 33
<211> LENGTH: 6
<212> TYPE: DNA
<213> ORGANISM: Artificial Sequence
<220> FEATURE:
<223> OTHER INFORMATION: oligonucleotide

<400> SEQUENCE: 33 ctcgag                                                              6

<210> SEQ ID NO 34
<211> LENGTH: 6
<212> TYPE: DNA
<213> ORGANISM: Artificial Sequence
<220> FEATURE:
<223> OTHER INFORMATION: oligonucleotide

<400> SEQUENCE: 34 tctaga                                                              6

<210> SEQ ID NO 35
<211> LENGTH: 6
<212> TYPE: DNA
```

```
<213> ORGANISM: Artificial Sequence
<220> FEATURE:
<223> OTHER INFORMATION: oligonucleotide

<400> SEQUENCE: 35 acgcgt                                                                      6

<210> SEQ ID NO 36
<211> LENGTH: 35
<212> TYPE: DNA
<213> ORGANISM: Artificial Sequence
<220> FEATURE:
<223> OTHER INFORMATION: oligonucleotide

<400> SEQUENCE: 36
ttttctagac caccatggct gtcctggggc tgctt                                      35

<210> SEQ ID NO 37
<211> LENGTH: 47
<212> TYPE: DNA
<213> ORGANISM: Artificial Sequence
<220> FEATURE:
<223> OTHER INFORMATION: oligonucleotide

<400> SEQUENCE: 37
ttttctagag gttgtgagga ctcacctgag gagacggtga ctgaggt                         47

<210> SEQ ID NO 38
<211> LENGTH: 31
<212> TYPE: DNA
<213> ORGANISM: Artificial Sequence
<220> FEATURE:
<223> OTHER INFORMATION: oligonucleotide

<400> SEQUENCE: 38
tggaacttac tacggaatga ctacgacggg g                                          31

<210> SEQ ID NO 39
<211> LENGTH: 31
<212> TYPE: DNA
<213> ORGANISM: Artificial Sequence
<220> FEATURE:
<223> OTHER INFORMATION: oligonucleotide

<400> SEQUENCE: 39
ccccgtcgta gtcattccgt agtaagttcc a                                          31

<210> SEQ ID NO 40
<211> LENGTH: 43
<212> TYPE: DNA
<213> ORGANISM: Artificial Sequence
<220> FEATURE:
<223> OTHER INFORMATION: oligonucleotide

<400> SEQUENCE: 40
ttttctagag gccattctta cctgaggaga cggtgactga ggt                             43

<210> SEQ ID NO 41
<211> LENGTH: 35
<212> TYPE: DNA
<213> ORGANISM: Artificial Sequence
<220> FEATURE:
<223> OTHER INFORMATION: oligonucleotide

<400> SEQUENCE: 41
tttacgcgtc caccatggat tttcaggtgc agatt                                      35
```

```
<210> SEQ ID NO 42
<211> LENGTH: 49
<212> TYPE: DNA
<213> ORGANISM: Artificial Sequence
<220> FEATURE:
<223> OTHER INFORMATION: oligonucleotide

<400> SEQUENCE: 42
ttttctagat taggaaagtg cacttacgtt tgatttccag cttggtgcc          49

<210> SEQ ID NO 43
<211> LENGTH: 31
<212> TYPE: DNA
<213> ORGANISM: Artificial Sequence
<220> FEATURE:
<223> OTHER INFORMATION: oligonucleotide

<400> SEQUENCE: 43
tgccagttca agtgtcagtt ccaattactt g                             31

<210> SEQ ID NO 44
<211> LENGTH: 31
<212> TYPE: DNA
<213> ORGANISM: Artificial Sequence
<220> FEATURE:
<223> OTHER INFORMATION: oligonucleotide

<400> SEQUENCE: 44
caagtaattg gaactgacac ttgaactggc a                             31

<210> SEQ ID NO 45
<211> LENGTH: 48
<212> TYPE: DNA
<213> ORGANISM: Artificial Sequence
<220> FEATURE:
<223> OTHER INFORMATION: oligonucleotide

<400> SEQUENCE: 45
ttttctagac tttggattct acttacgttt gatttccagc ttggtgcc           48

<210> SEQ ID NO 46
<211> LENGTH: 143
<212> TYPE: PRT
<213> ORGANISM: mus musculus

<400> SEQUENCE: 46

Met Ala Val Leu Gly Leu Leu Cys Leu Val Thr Phe Pro Ser Cys
 1               5                  10                  15

Val Leu Ser Gln Val Gln Leu Lys Glu Ser Gly Pro Gly Leu Val Ala
                20                  25                  30

Pro Ser Gln Ser Leu Ser Ile Thr Cys Thr Ile Ser Gly Phe Ser Leu
        35                  40                  45

Thr Asp Tyr Gly Val His Trp Val Arg Gln Pro Pro Gly Lys Gly Leu
    50                  55                  60

Glu Trp Leu Val Val Ile Trp Ser Asp Gly Ser Ser Thr Tyr Asn Ser
65                  70                  75                  80

Ala Leu Lys Ser Arg Met Thr Ile Arg Lys Asp Asn Ser Lys Ser Gln
                85                  90                  95

Val Phe Leu Ile Met Asn Ser Leu Gln Thr Asp Asp Ser Ala Met Tyr
            100                 105                 110

Tyr Cys Ala Arg His Gly Thr Tyr Tyr Gly Met Thr Thr Thr Gly Asp
        115                 120                 125
```

-continued

```
Ala Leu Asp Tyr Trp Gly Gln Gly Thr Ser Val Thr Val Ser Ser
    130                 135                 140

<210> SEQ ID NO 47
<211> LENGTH: 130
<212> TYPE: PRT
<213> ORGANISM: mus musculus

<400> SEQUENCE: 47

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
            35                  40                  45

Ser Ser Val Ser Ser Asn Tyr Leu His Trp Tyr Gln Gln Lys Pro Gly
        50                  55                  60

Ser Ala Pro Asn Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr Leu Arg Ser Pro Pro Thr Phe Gly Gly Gly Thr Lys Leu Glu
            115                 120                 125

Ile Lys
    130
```